US008828356B2

(12) United States Patent
Gordon et al.

(10) Patent No.: US 8,828,356 B2
(45) Date of Patent: *Sep. 9, 2014

(54) FARNESYLTRANSFERASE INHIBITORS FOR TREATMENT OF LAMINOPATHIES, CELLULAR AGING AND ATHEROSCLEROSIS

(71) Applicants: The United States of America as represented by the Secretary of the Department of Health and Human Services, Washington, DC (US); Progeria Research Foundation, Inc., Peabody, MA (US); The Regents of the University of Michigan, Ann Arbor, MI (US); The University of North Carolina at Chapel Hill, Chapel Hill, NC (US)

(72) Inventors: Leslie B. Gordon, Foxboro, MA (US); Francis S. Collins, Rockville, MD (US); Thomas Glover, Ypsilanti, MI (US); Michael W. Glynn, Darien, CT (US); Brian C. Capell, Philadelphia, PA (US); Adrienne D. Cox, Chapel Hill, NC (US); Channing J. Der, Chapel Hill, NC (US)

(73) Assignees: Progeria Research Foundation, Inc., Peabody, MA (US); The United States of America as represented by the Secretary of the Department of Health and Human Services, Washington, DC (US); The University of North Carolina at Chapel Hill, Chapel Hill, NC (US); The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,052

(22) Filed: Apr. 4, 2013

(65) Prior Publication Data
US 2013/0203799 A1     Aug. 8, 2013

Related U.S. Application Data

(60) Continuation of application No. 13/567,432, filed on Aug. 6, 2012, now Pat. No. 8,691,501, which is a division of application No. 12/905,838, filed on Oct. 15, 2010, now Pat. No. 8,257,915, which is a division of application No. 11/828,117, filed on Jul. 25, 2007, now Pat. No. 7,838,531, which is a continuation-in-part of application No. PCT/US2006/002977, filed on Jan. 27, 2006, and a continuation-in-part of application No. 10/943,400, filed on Sep. 17, 2004, now Pat. No. 7,297,492, which is a continuation of application No. PCT/US03/33058, filed on Oct. 17, 2003.

(60) Provisional application No. 60/648,307, filed on Jan. 28, 2005, provisional application No. 60/707,192, filed on Aug. 9, 2005, provisional application No. 60/463,084, filed on Apr. 14, 2003, provisional application No. 60/419,541, filed on Oct. 18, 2002.

(51) Int. Cl.
*A61K 49/00* (2006.01)
*C12Q 1/48* (2006.01)

(52) U.S. Cl.
USPC .............................................. 424/9.2; 435/15

(58) Field of Classification Search
USPC .............................................. 424/9.2; 435/15
See application file for complete search history.

(56) References Cited

U.S. PATENT DOCUMENTS 6,060,038 A    5/2000 Burns et al.
6,342,487 B1   1/2002 Riou et al.

(Continued)

FOREIGN PATENT DOCUMENTS

WO    WO 97/30053    8/1997
WO    WO 01/64218    9/2001

(Continued)

OTHER PUBLICATIONS

Eskins et al. Phase I and Pharmacokinetic Study of the Oral Farnesyl Transferase Inhibitor SCH66336 Given Twice Daily to Patients With Advanced Solid Tumors; Journal of Clinical Oncology, vol. 19 (2001) pp. 1167-1175.*

(Continued)

*Primary Examiner* — Susan Hanley
*Assistant Examiner* — Paul Martin
(74) *Attorney, Agent, or Firm* — Klarquist Sparkman, LLP

(57) ABSTRACT

Although it can be farnesylated, the mutant lamin A protein expressed in Hutchinson Gilford Progeria Syndrome (HGPS) cannot be defarnesylated because the characteristic mutation causes deletion of a cleavage site necessary for binding the protease ZMPSTE24 and effecting defarnesylation. The result is an aberrant farnesylated protein (called "progerin") that alters normal lamin A function as a dominant negative, as well as assuming its own aberrant function through its association with the nuclear membrane. The retention of farnesylation, and potentially other abnormal properties of progerin and other abnormal lamin gene protein products, produces disease. Farnesyltransferase inhibitors (FTIs) (both direct effectors and indirect inhibitors) will inhibit the formation of progerin, cause a decrease in lamin A protein, and/or an increase prelamin A protein. Decreasing the amount of aberrant protein improves cellular effects caused by and progerin expression. Similarly, treatment with FTIs should improve disease status in progeria and other laminopathies. In addition, elements of atherosclerosis and aging in non-laminopathy individuals will improve after treatment with farnesyltransferase inhibitors.

14 Claims, 15 Drawing Sheets

(56) References Cited

U.S. PATENT DOCUMENTS

| | | |
|---|---|---|
| 6,737,410 B1 | 5/2004 | Doherty et al. |
| 2002/0044941 A1 | 4/2002 | Rosen et al. |
| 2002/0098495 A1 | 7/2002 | Burmer et al. |
| 2003/0119864 A1 | 6/2003 | Gordon et al. |
| 2003/0125326 A1 | 7/2003 | Rybak |
| 2004/0110769 A1 | 6/2004 | End |

FOREIGN PATENT DOCUMENTS

| | | |
|---|---|---|
| WO | WO 02/04662 | 1/2002 |
| WO | WO 2004/035753 | 4/2004 |
| WO | WO 2006/081444 | 8/2006 |
| WO | WO 2006/128180 | 11/2006 |

OTHER PUBLICATIONS

Adelfalk et al., Nuclear deformation characterizes Werner Syndrome cells, *Cell Biol. Int.*, 29:1032-1037, 2005.

Adjei et al. "A phase I trial of the farnesyl transferase inhibitor SCH66336: evidence for biological and clinical activity," *Cancer Research* 60 (7): 1871-1877, 2000.

Adjei et al. "Phase II study of the farnesyl transferase inhibitor R115777 in patients with advanced non-small-cell lung cancer," *J Clinical Oncology* 21 (9): 1760-1766, 2003.

Adjei et al., "Comparison of Potential Markers of Farnesyltransferase Inhibition," *Clinical Cancer Res.*, 6:2318-2325, Jun. 2000.

Alsina et al. "Farnesyltransferase inhibitor tipifarnib is well tolerated, induces stabilization of disease, and inhibits farnesylation and oncogenic/tumor survival pathways in patients with advanced multiple myeloma," *Blood* 103(9): 3271-3277, May 2004.

Amtmann et al., "Restoration of the Responsiveness to Growth Factors in Senescent Cells by an Embryonic Cell Extract," *Experimental Cell Research*, 189:202-207, 1990.

Ayral-Kaloustian and Salaski, "Protein Farnesyltransferase Inhibitors," *Current Medical Chemistry* 9 (10): 1003-1032, 2002.

Basso et al. "Farnesyl transferase inhibitors," *Journal of Lipid Research* 47: 15-31, 2006.

Beck et al. "Isoprenylation is Required for the Processing of the Lamin A Precursor," *Journal of Cell Biology* 110: 1489-1499, May 1990.

Bonne et al., "Clinical and Molecular Genetic Spectrum of Autosomal Dominant Emery-Dreifuss Muscular Dystrophy due to Mutations of the Lamin A/C Gene," *Annals of Neurology* 48(2):170-180, Aug. 2000.

Bonne et al., "Mutations in the gene encoding lamin A/C cause autosomal dominant Emery-Dreifuss muscular dystrophy," *Nature Genetics* 21(3): 285-288, Mar. 1999.

Burke and Stewart, "Life at the Edge: The Nuclear Envelope and Human Disease," *Molecular Cell Biology—Nature Reviews* 3:575-585, Aug. 2002.

Cao and Hegele, "*LMNA* is mutated in Hutchinson-Gilford progeria (MIM 176670) but not in Wiedemann-Rautenstrauch progeroid syndrome (MIM 264090)," *J. Hum. Genet.* 48:271-274, 2003.

Cao et al. "A lamin A protein isoform overexpressed in Hutchinson-Gilford progeria syndrome interferes with mitosis in progeria and normal cells," *PNAS* 104(12): 4949-4954, Mar. 2007.

Capell et al., "Inhibiting farnesylation of progerin prevents the characteristic nuclear blebbing of Hutchinson-Gilford progeria syndrome," *PNAS* 102(36): 12879-12884, Sep. 2005.

Chen et al. "LMNA mutations in atypical Werner's syndrome," *Lancet* 362 (9382): 440-445, 2003.

Cohen et al., "Inhibitors of Prenylation of Ras and Other G-proteins and Their Application as Therapeutics," *Biochem. Pharm.*, 60:1061-1068, 2000.

Colige et al., "Abnormal Gene Expression in Skin Fibroblasts From a Hutchinson-Gilford Patient," *Laboratory Investigation*, 64(6):799-806, 1991.

Cox and Der, "Farnesyltransferase inhibitors: promises and realities," *Curr. Opin. Pharm.* 2:388-393, 2002.

De Sandre-Giovannoli et al., "Homozygous Defects in LMNA, Encoding Lamin A/C Nuclear-Envelope Proteins, Cause Autosomal Recessive Axonal Neuropathy in Human (Charcot-Marie-Tooth Disorder Type 2) and Mouse," *Am. J. Hum. Genet.* 70(3): 726-736, 2002.

De Sandre-Giovannoli, et al., "Lamin A Truncation in Hutchinson-Gilford Progeria," *Science* 300(4):2055, Jun. 27, 2003.

Delahunt et al., "Progeria kidney has abnormal mesangial collagen distribution," *Pediatr. Nephrol.* 15:279-285, 2000.

Eriksson et al., "Recurrent *de novo* point mutations in lamin A cause Hutchinson-Gilford Progeria Syndrome," *Nature* 423:293-298, May 15, 2003.

Faivre et al., "Can Hutchinson-Gilford Progeria Syndrome be a Neonatal Condition?" *Letter to the Editor—Am. J. Med. Genet.* 87:450-452, 1999.

Fisher et al., "cDNA sequencing of nuclear lamins A and C reveals primary and secondary structural homology to intermediate filament proteins," *Proc. Natl. Acad. Sci. USA* 83:6450-6454, Sep. 1986.

Fong et al. "A protein farnesyltransferase inhibitor ameliorates disease in a mouse model of progeria," *Science* 311(5767); 1621-1623, Published Online Feb. 2006.

Fong et al. "Prelamin A and lamin A appear to be dispensable in the nuclear lamina," *J. Clin. Invest.* 116(3): 743-752, Mar. 2006.

Fong et al., "Heterozygosity for *LMNA* deficiency eliminates the progeria-like phenotypes in Zmpste24-deficient mice," *Proc. Natl. Sci. Acad. USA* 101(52)18111-18116, Dec. 28, 2004.

Garcia et al., "Peptidomimetic Inhibitors of Ras Farnesylation and Function in Whole Cells," *J. Biol. Chem.*, 268(25):18415-18418, 1993.

Genschel et al., "Mutations in the LMNA Gene Encoding Lamin A/C," *Human Mutation* 16(6): 451-459, 2000.

Glynn et al. "Incomplete processing of mutant lamin A in Hutchinson-Gilford progeria leads to nuclear abnormalities, which are reversed by farnesyltransferase inhibition," *Human Molecular Genetics* 14(20): 2959-2969, 2005.

Goldman et al., "Accumulation of mutant lamin A causes progressive changes in nuclear architecture in Hutchinson-Gilford progeria syndrome," *Proc. Natl. Acad. Sci. USA* 101(24):8963-8968, Jun. 15, 2004.

Gordon et al., "Clinical trial of a farnesyltransferase inhibitor in children with Hutchinson-Gilford progeria syndrome," *Proc. Natl. Acad. Sci. USA* 109(41):16666-16671, 2012.

Ha et al., "Cardiovascular Findings of Hutchinson-Gilford Syndrome—A Doppler and two-dimensional Echocardiographic study—," *Yonsei Med. J.* 34(4):352-355, 1993.

Hegele et al., "Common Genomic Variation in LMNA Modulates Indexes of Obesity in Inuit," *J Clinical Endocrinology and Metabolism* 86(6): 2747-2751, 2001.

Hegele, "Premature Atherosclerosis Associated with Monogenic Insulin Resistance," *Circulation* 103(18): 2225-2229, 2001.

Henig, "Racing with Sam," *The New York Times Magazine*, 46-51, Jan. 30, 2005.

Hoeffel et al., "Mandibulo-acral dysplasia," *Skeletal Radiol.* 29:668-671, 2000.

Hoover et al., "Overcoming STI571 resistance with the farnesyl transferase inhibitor SCH66336," *Blood*, 100(3):1068-1071, Aug. 1, 2002.

Huang et al. "Correction of cellular phenotypes of Hutchinson-Gilford Progeria cells by RNA interference," *Hum. Genet.* 118(3-4): 444-450, Published Online Oct. 2005.

Hutchinson, "Lamins: Building Blocks or Regulators of Gene Expression?" *Molecular Cell Biology* 3(11):848-858, Nov. 2002.

Ikeda and Shimada, Pleiotropic Effects of Statins on the Vascular Tissue, *Current Drug Targets—Cardiovascular & Haematological Disorders*, 1(1):51-58, 2001.

Jansen and Romiti, "Progeria Infantum (Hutchinson-Gilford Syndrome) Associated with Scleroderma-Like Lesions and Acro-Osteolysis: A Case Report and Brief Review of the Literature," *Pediatric Dermatology* 17(4):282-285, 2000.

Lutz et al., "Nucleoplasmic localization of prelamin A: Implications for prenylation-dependent lamin A assembly into the nuclear lamina," *Proc. Natl. Acad. Sci. USA* 89:3000-3004, Apr. 1992.

Ly et al., "Mitotic Misregulation and Human Aging," *Science* 287:2486, 2000.

(56) References Cited

OTHER PUBLICATIONS

Machiels et al., "An Alternative Splicing Product of the Lamin A/C Gene Lacks Exon 10," *J Biological Chemistry* 271(16): 9249-9253, 1996.

Mallampalli et al. "Inhibiting farnesylation reverses the nuclear morphology defect in a HeLa cell model for Hutchinson-Gilford progeria syndrome," *PNAS* 102(40): 14416-14421, Published Online Sep. 2005, 10.1073.

Maske et al., "A carboxyl-terminal interaction of lamin B1 is dependent on the CAAX endoprotease Rce1 and carboxymethylation," *J. Cell Biol.*, 162(7):1223-1232, Sep. 29, 2003.

McKeon et al., "Homologies in both primary and secondary structure between nuclear envelope and intermediate filament proteins," *Nature* 319:463-468, Feb. 6, 1986.

Mégnin-Chanet et al., "The farnesyl transferase inhibitor RPR-130401 does not alter radiation susceptibility in human tumor cells with a K-Ras mutation in spite of large changes in ploidy and lamin B distribution," *BMC Pharm.* 2:2, E-pub Feb. 6, 2002.

Morris, G.E., "The Role of the Nuclear Envelope in Emery-Dreifuss Muscular Dystrophy," *Trends in Molecular Medicine*, 7(12):572-577, 2001.

Mounkes et al., "The A-Type Lamins Nuclear Structural Proteins as a Focus for Muscular Dystrophy and Cardiovascular Diseases," *TCM*, 11(7): 280-285, 2001.

Nalbone et al., "Statins: Maid-of-all-work in Cardiovascular Diseases!" *Archives Des Maladies Du Coeur Et Des Vaisseaux*, 96(3):207-213, Mar. 2003.

Novelli et al., "Mandibuloacral Dysplasia is Caused by a Mutation in LMNA-Encoding Lamin A/C," *Am. J. Hum. Genet.*, 71:426-431, 2002.

Östlund et al., "Nuclear Envelope Proteins and Neuromuscular Diseases," *Muscle & Nerve*, 27:393-406, 2003.

Parnaik et al., "Laminopathies: Multiple disorders arising from defects in nuclear architecture," *J. Biosci*, 31(3): 405-421, 2006.

Pesce and Rothe, "The Premature Aging Syndromes," *Clinics in Dermatology* 14:161-170, 1996.

Peters et al., "Activity of the farnesyl protein transferase inhibitor SCH66336 against BCR/ABL-induced murine leukemia and primary cells from patients with chronic myeloid leukemia," *Blood* 97(5):1404-1412, Mar. 1, 2001.

Pollex and Hegele, "Hutchinson-Gilford progeria syndrome," *Clin. Genet.*, 66:375-381, 2004.

Rao et al. "Phase II Double-Blind Placebo-Controlled Study of Farnesyl Transferase Inhibitor R115777 in Patients with Refractory Advanced Colorectal Cancer," *Journal of Clinical Oncology* 22(19): 3950-3957, Oct. 2004.

Rodríguez and Pérez-Alonso, "Diagnosis of Progeria Syndrome is the Only One Possible," *Letter to the Editor—Am. J. Med. Genet.*, 87:453-454, 1999.

Rodríguez et al., "Lethal Neonatal Hutchinson-Gilford Progeria Syndrome," *Am. J. Med. Genet.*, 82:242-248, 1999.

Rosenblum et al., "On signal sequence polymorphisms and diseases of distribution," *Proc. Natl. Acad. Sci. USA* 93:4471-4473, Apr. 1996.

Sarkar and Shinton, "Hutchinson-Gilford progeria syndrome," *Postgrad Med J.* 77:312-317, May 2001.

Scaffidi and Misteli, "Lamin A-Dependent Nuclear Defects in Human Aging," *Science* 312(5776): 1059-1063, Published Online Apr. 2006.

Scaffidi and Misteli, "Reversal of the cellular phenotype in the premature aging disease Hutchinson-Gilford progeria syndrome," *Nat Med.* 11(4): 440-445, Published Online Mar. 2005.

Sinensky et al. "The processing pathway of prelamin A," *Journal of Cell Science* 107: 61-67, 1994.

Sullivan et al., "Loss of A-Type Lamin Expression Compromises Nuclear Envelope Integrity Leading to Muscular Dystrophy," *The Journal of Cell Biology*, 147(5):913-919, 1999.

Toth et al., "Blocking protein farnesyltransferase improves nuclear shape in fibroblasts from humans with progeroid syndromes," *PNAS*, 102:12873-12878, 2005.

Uitto "Searching for clues to premature aging," *Trends in Endocrinology & Metabolism* 13(4):140-141, May/Jun. 2004.

Yang et al. "Blocking protein farnesyltransferase improves nuclear blebbing in mouse fibroblasts with a targeted Hutchinson-Gilford progeria syndrome mutation," *PNAS* 102(9): 10291-10293, Jul. 2005.

Young et al. "Prelamin A, Zmpste24, misshapen cell nuclei, and progeria—new evidence suggesting that protein farnesylation could be important for disease pathogenesis," *J. Lipid Res.* ; 46(12): 2531-2558, Published Online Oct. 2005.

AH001498 Human nuclear lamin A and nuclear lamin C gene, Feb. 11, 2000. *NCBI* printed Oct. 17, 2002.

Database EMBL (online), "*Homo sapiens* lamin A/C, transcript variant 1, mRNA (cDNA clone MGC:23638 Image:4863480), complete cds," Accession No. BC014507, Sep. 24, 2001.

Database UniProt (online), "Lamin A/C (70 kDa Lamin)," Accession No. P02545, Jul. 21, 1986.

"Grants Funded," The Progeria Research Foundation, available online as of Jul. 21, 2007 at http://progeriaresearch.org/assets/plugins/fckeditor/editor/grants_funded.html.

"Hutchinson-Gilford Progeria (HGPS) Syndrome Workshop," Agenda, Participants, and Abstracts available online as of Jan. 10, 2005 at http://rarediseases.info.nih.gov/html/workshops/workshops/hutchinson-gilford2003.html.

"Lamin A/C (LMNA)" *Leiden Muscular Dystrophy pages* © (Sep. 8, 2002), www.dmd.nl/lmna_home.html.

"The Progeria Clinical Research Drug Trial: Who, Where, When, How and How Much . . ." The Progeria Research Foundation, online as of Jul. 5, 2007 at http:/www.progeriaresearch.org/progeria_clinical_drug_trial_has_begun.html.

L12401 Human nuclear lamin A and nuclear lamin gene, exons 3-12 and complete alternative mRNAs, Feb. 11, 2000. *NCBI* printed Oct. 17, 2002.

* cited by examiner

FIGURE 6
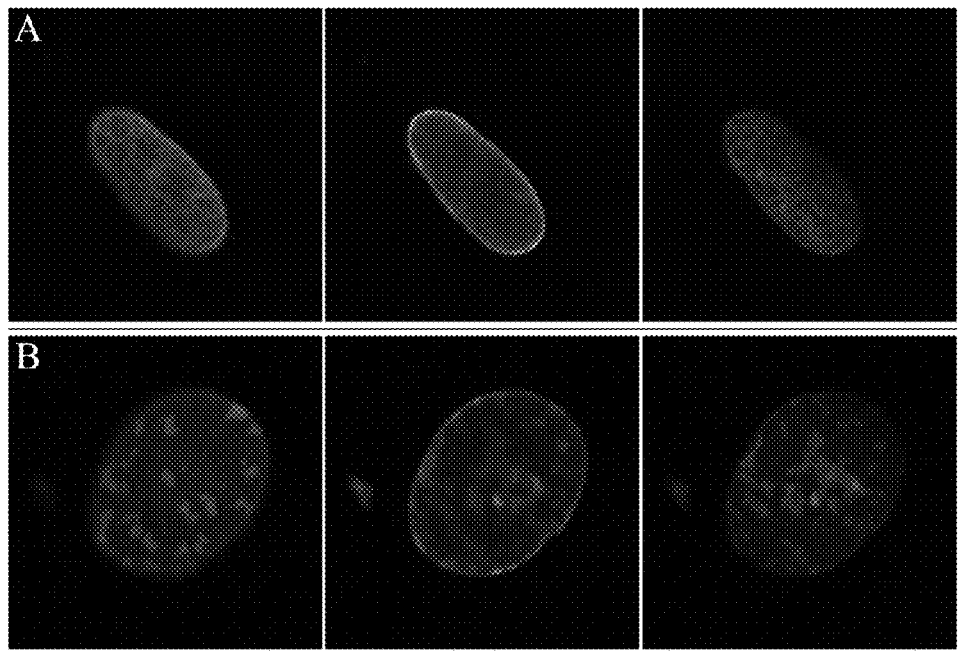
FIGURE 7A & B
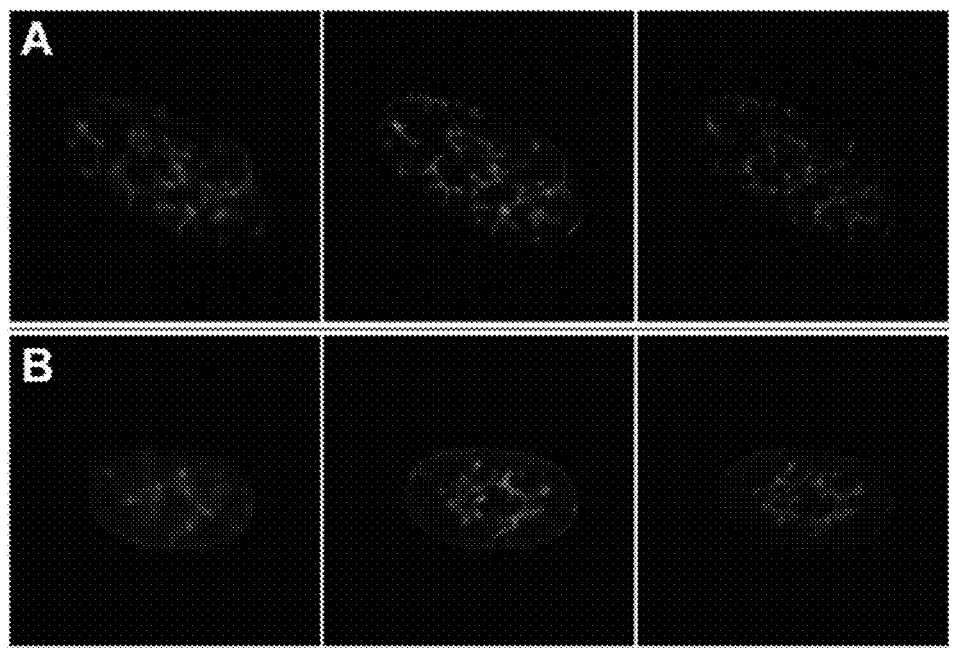

FIGURE 13
MAP 1
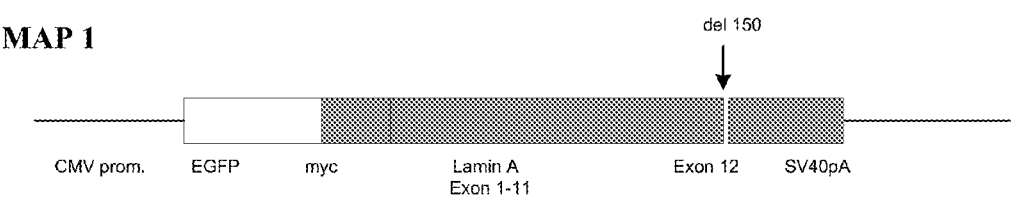
MAP 2
MAP 3
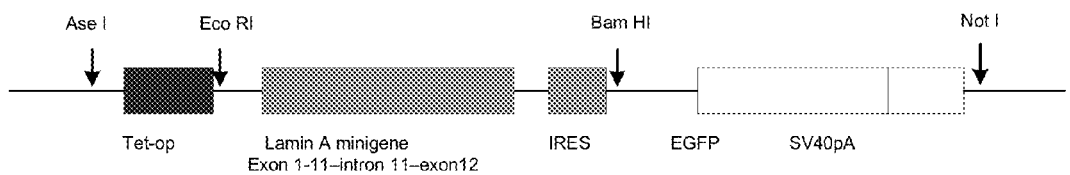

FIGURE 14
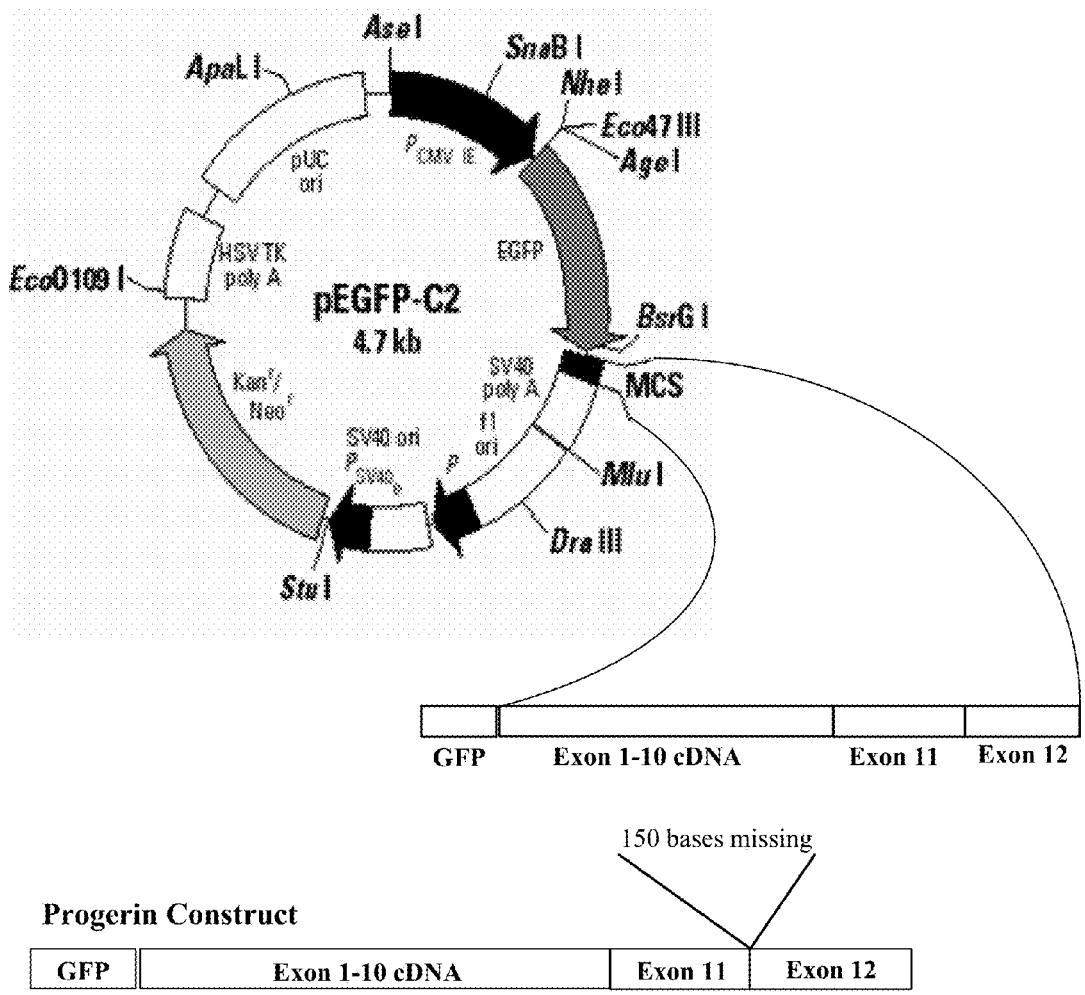
Progerin Construct
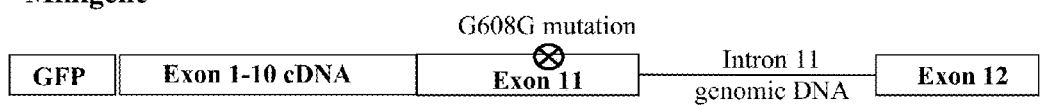

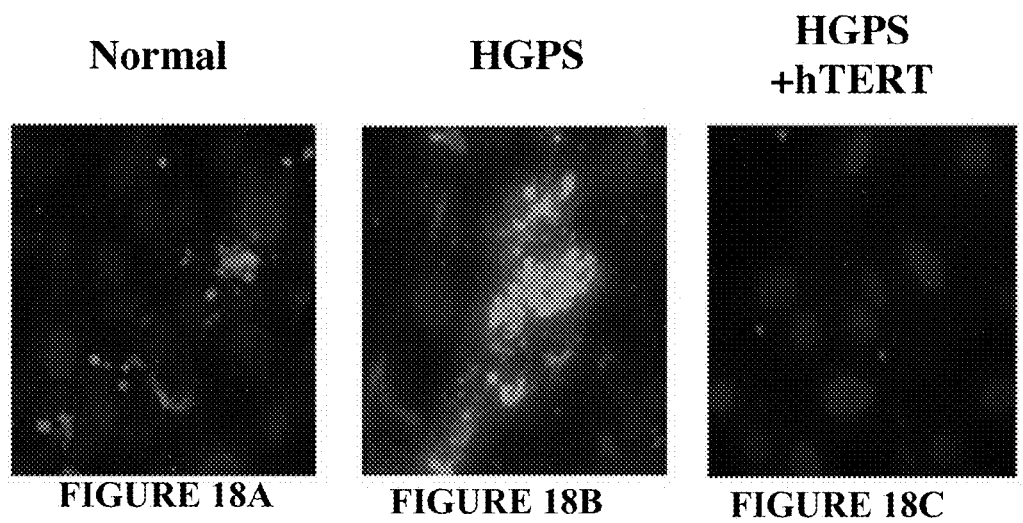
FIGURE 18A    FIGURE 18B    FIGURE 18C
FIGURE 19
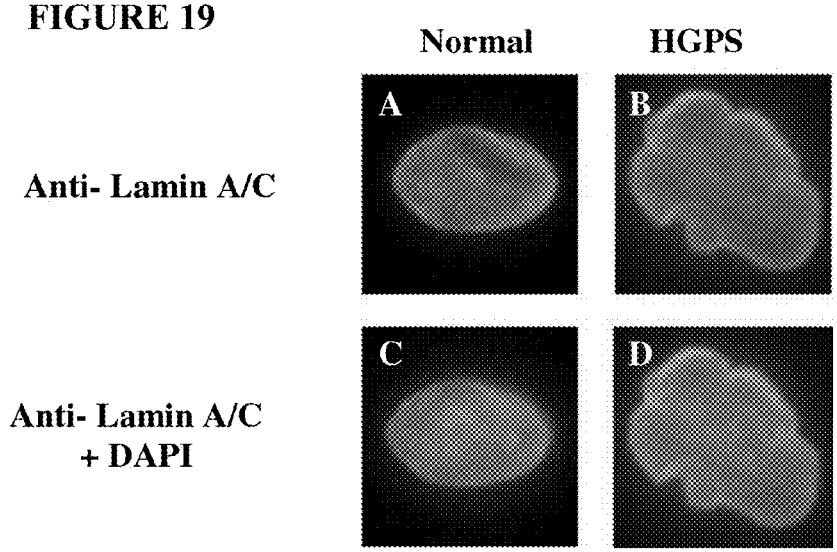
Anti- Lamin A/C
Anti- Lamin A/C + DAPI
FIGURE 20
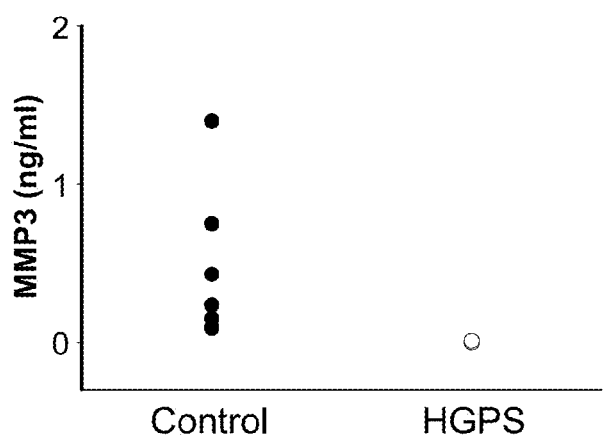

SEQUENCE LISTING

```
<160> NUMBER OF SEQ ID NOS: 34

<210> SEQ ID NO 1
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 1
agcagtctct gtccttcgac cc                                              22

<210> SEQ ID NO 2
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 2
cttccacctc ccacctcatt cc                                              22

<210> SEQ ID NO 3
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 3
gtggaggagg tggatgagga gggcaag                                         27

<210> SEQ ID NO 4
<211> LENGTH: 30
<212> TYPE: DNA
```

```
<213> ORGANISM: Artificial sequence
<220> FEATURE:
<223> OTHER INFORMATION: Synthetic Oligonucleotide

<400> SEQUENCE: 4
tggagttgcc caggcggtag gagcgggtga                                              30

<210> SEQ ID NO 5
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 5
tcacccgctc ctaccgcctg ggcaactcca                                              30

<210> SEQ ID NO 6
<211> LENGTH: 26
<212> TYPE: DNA
<213> ORGANISM: Artificial sequence
<220> FEATURE:
<223> OTHER INFORMATION: Synthetic Oligonucleotide

<400> SEQUENCE: 6
ctgagggctg gaccgcatct ggggac                                                  26

<210> SEQ ID NO 7
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 7
catgggcaat tggcagatca ag                                                      22

<210> SEQ ID NO 8
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 8
catgccttgc aaaatggcgt tac                                                     23

<210> SEQ ID NO 9
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 9
tcaggagccc agcgaccc                                                           18

<210> SEQ ID NO 10
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 10
ttctttggca agccccc                                                            17
```

<210> SEQ ID NO 11
<211> LENGTH: 38
<212> TYPE: DNA
<213> ORGANISM: Artificial sequence
<220> FEATURE:
<223> OTHER INFORMATION: Synthetic Oligonucleotide

<400> SEQUENCE: 11
ccagagcccc cagaactcaa gcatcatgta atctagag                                  38

<210> SEQ ID NO 12
<211> LENGTH: 38
<212> TYPE: DNA
<213> ORGANISM: Artificial sequence
<220> FEATURE:
<223> OTHER INFORMATION: Synthetic Oligonucleotide

<400> SEQUENCE: 12
ctctagatta catgatgctt gagttctggg ggctctgg                                  38

<210> SEQ ID NO 13
<211> LENGTH: 40
<212> TYPE: DNA
<213> ORGANISM: Artificial sequence
<220> FEATURE:
<223> OTHER INFORMATION: Synthetic Oligonucleotide

<400> SEQUENCE: 13
ccccagaact gcagcatctt ataatctaga gtcgacggta                                40

<210> SEQ ID NO 14
<211> LENGTH: 40
<212> TYPE: DNA
<213> ORGANISM: Artificial sequence
<220> FEATURE:
<223> OTHER INFORMATION: Synthetic Oligonucleotide

<400> SEQUENCE: 14
taccgtcgac tctagattat aagatgctgc agttctgggg                                40

<210> SEQ ID NO 15
<211> LENGTH: 38
<212> TYPE: DNA
<213> ORGANISM: Artificial sequence
<220> FEATURE:
<223> OTHER INFORMATION: Synthetic Oligonucleotide

<400> SEQUENCE: 15
cttagagccc ccagaactca agcatcatgt aatctggg                                  38

<210> SEQ ID NO 16
<211> LENGTH: 38
<212> TYPE: DNA
<213> ORGANISM: Artificial sequence
<220> FEATURE:
<223> OTHER INFORMATION: Synthetic Oligonucleotide

<400> SEQUENCE: 16
cccagattac atgatgcttg agttctgggg gctctaag                                  38

<210> SEQ ID NO 17
<211> LENGTH: 38
<212> TYPE: DNA
<213> ORGANISM: Artificial sequence
<220> FEATURE:

<223> OTHER INFORMATION: Synthetic Oligonucleotide

<400> SEQUENCE: 17

| cccagaactg cagcatctta taatctggga cgggatcc | 38 |
|---|---|

<210> SEQ ID NO 18
<211> LENGTH: 38
<212> TYPE: DNA
<213> ORGANISM: Artificial sequence
<220> FEATURE:
<223> OTHER INFORMATION: Synthetic Oligonucleotide

<400> SEQUENCE: 18

| ggatcccgtc ccagattata agatgctgca gttctggg | 38 |
|---|---|

<210> SEQ ID NO 19
<211> LENGTH: 1995
<212> TYPE: DNA
<213> ORGANISM: Homo sapiens

<400> SEQUENCE: 19

| atggagaccc cgtcccagcg gcgcgccacc cgcagcgggg cgcaggccag ctccactccg | 60 |
|---|---|
| ctgtcgccca cccgcatcac ccggctgcag gagaaggagg acctgcagga gctcaatgat | 120 |
| cgcttggcgg tctacatcga ccgtgtgcgc tcgctggaaa cggagaacgc agggctgcgc | 180 |
| cttcgcatca ccgagtctga agaggtggtc agccgcgagg tgtccggcat caaggccgcc | 240 |
| tacgaggccg agctcgggga tgcccgcaag acccttgact cagtagccaa ggagcgcgcc | 300 |
| cgcctgcagc tggagctgag caaagtgcgt gaggagttta aggagctgaa agcgcgcaat | 360 |
| accaagaagg agggtgacct gatagctgct caggctcggc tgaaggacct ggaggctctg | 420 |
| ctgaactcca aggaggccgc actgagcact gctctcagtg agaagcgcac gctggagggc | 480 |
| gagctgcatg atctgcgggg ccaggtggcc aagcttgagg cagccctagg tgaggccaag | 540 |
| aagcaacttc aggatgagat gctgcggcgg gtggatgctg agaacaggct gcagaccatg | 600 |
| aaggaggaac tggacttcca agaacatc tacagtgagg agctgcgtga gaccaagcgc | 660 |
| cgtcatgaga cccgactggt ggagattgac aatgggaagc agcgtgagtt tgagagccgg | 720 |
| ctggcggatg cgctgcagga actgcgggcc cagcatgagg accaggtgga gcagtataag | 780 |
| aaggagctgg agaagactta ttctgccaag ctggacaatg ccaggcagtc tgctgagagg | 840 |
| aacagcaacc tggtgggggc tgcccacgag gagctgcagc agtcgcgcat ccgcatcgac | 900 |
| agcctctctg cccagctcag ccagctccag aagcagctgg cagccaagga ggcgaagctt | 960 |
| cgagacctgg aggactcact ggcccgtgag cgggacacca gccggcggct gctggcggaa | 1020 |
| aaggagcggg agatggccga gatgcgggca aggatgcagc agcagctgga cgagtaccag | 1080 |
| gagcttctgg acatcaagct ggccctggac atggagatcc acgcctaccg caagctcttg | 1140 |
| gagggcgagg aggagaggct acgcctgtcc cccagcccta cctcgcagcg cagccgtggc | 1200 |
| cgtgcttcct ctcactcatc ccagacacag ggtgggggca cgtcaccaa aaagcgcaaa | 1260 |
| ctggagtcca ctgagagccg cagcagcttc tcacagcacg cacgcactag cgggcgcgtg | 1320 |
| gccgtggagg aggtggatga ggagggcaag tttgtccggc tgcgcaacaa gtccaatgag | 1380 |
| gaccagtcca tgggcaattg gcagatcaag cgccagaatg gagatgatcc cttgctgact | 1440 |
| taccggttcc caccaaagtt caccctgaag gctgggcagg tggtgacgat ctgggctgca | 1500 |
| ggagctgggg ccacccacag ccccctacc gacctggtgt ggaaggcaca gaacacctgg | 1560 |
| ggctgcggga acagcctgcg tacggctctc atcaactcca ctggggaaga agtggccatg | 1620 |

-continued

```
cgcaagctgg tgcgctcagt gactgtggtt gaggacgacg aggatgagga tggagatgac    1680
ctgctccatc accaccacgg ctcccactgc agcagctcgg gggaccccgc tgagtacaac    1740
ctgcgctcgc gcaccgtgct gtgcgggacc tgcgggcagc ctgccgacaa ggcatctgcc    1800
agcggctcag gagcccaggt gggcggaccc atctcctctg gctcttctgc ctccagtgtc    1860
acggtcactc gcagctaccg cagtgtgggg ggcagtgggg gtggcagctt cggggacaat    1920
ctggtcaccc gctcctacct cctgggcaac tccagccccc gaacccagag cccccagaac    1980
tgcagcatca tgtaa                                                    1995
```

<210> SEQ ID NO 20
<211> LENGTH: 664
<212> TYPE: PRT
<213> ORGANISM: Homo sapiens

<400> SEQUENCE: 20

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300
```

```
Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
            660
```

<210> SEQ ID NO 21
<211> LENGTH: 1995
<212> TYPE: DNA
<213> ORGANISM: Homo sapiens

<400> SEQUENCE: 21
atggagaccc cgtcccagcg gcgcgccacc cgcagcgggg cgcaggccag ctccactccg      60

-continued

```
ctgtcgccca cccgcatcac ccggctgcag gagaaggagg acctgcagga gctcaatgat    120
cgcttggcgg tctacatcga ccgtgtgcgc tcgctggaaa cggagaacgc agggctgcgc    180
cttcgcatca ccgagtctga agaggtggtc agccgcgagg tgtccggcat caaggccgcc    240
tacgaggccg agctcgggga tgcccgcaag acccttgact cagtagccaa ggagcgcgcc    300
cgcctgcagc tggagctgag caaagtgcgt gaggagttta aggagctgaa agcgcgcaat    360
accaagaagg agggtgacct gatagctgct caggctcggc tgaaggacct ggaggctctg    420
ctgaactcca aggaggccgc actgagcact gctctcagtg agaagcgcac gctggagggc    480
gagctgcatg atctgcgggg ccaggtggcc aagcttgagg cagccctagg tgaggccaag    540
aagcaacttc aggatgagat gctgcggcgg gtggatgctg agaacaggct gcagaccatg    600
aaggaggaac tggacttcca gaagaacatc tacagtgagg agctgcgtga ccaagcgc     660
cgtcatgaga cccgactggt ggagattgac aatgggaagc agcgtgagtt tgagagccgg    720
ctggcggatg cgctgcagga actgcgggcc cagcatgagg accaggtgga gcagtataag    780
aaggagctgg agaagactta ttctgccaag ctggacaatg ccaggcagtc tgctgagagg    840
aacagcaacc tggtggggc tgcccacgag gagctgcagc agtcgcgcat ccgcatcgac    900
agcctctctg cccagctcag ccagctccag aagcagctgg cagccaagga ggcgaagctt    960
cgagacctgg aggactcact ggcccgtgag cgggacacca gcggcggct gctggcggaa   1020
aaggagcggg agatggccga gatgcgggca aggatgcagc agcagctgga cgagtaccag   1080
gagcttctgg acatcaagct ggccctggac atggagatcc acgcctaccg caagctcttg   1140
gagggcgagg aggagaggct acgcctgtcc cccagcccta cctcgcagcg cagccgtggc   1200
cgtgcttcct ctcactcatc ccagacacag ggtgggggca gcgtcaccaa aaagcgcaaa   1260
ctggagtcca ctgagagccg cagcagcttc tcacagcacg cacgcactag cgggcgcgtg   1320
gccgtggagg aggtggatga ggagggcaag tttgtccggc tgcgcaacaa gtccaatgag   1380
gaccagtcca tgggcaattg cagatcaag cgccagaatg gagatgatcc cttgctgact   1440
taccggttcc caccaaagtt caccctgaag gctgggcagg tggtgacgat ctgggctgca   1500
ggagctgggg ccacccacag ccccctacc gacctggtgt ggaaggcaca gaacacctgg   1560
ggctgcggga acagcctgcg tacggctctc atcaactcca ctggggaaga agtggccatg   1620
cgcaagctgg tgcgctcagt gactgtggtt gaggacgacg aggatgagga tggagatgac   1680
ctgctccatc accaccacgg ctcccactgc agcagctcgg gggaccccgc tgagtacaac   1740
ctgcgctcgc gcaccgtgct gtgcgggacc tgcgggcagc tgccgacaa ggcatctgcc   1800
agcggctcag gagcccaggt gggcggaccc atctcctctg gctcttctgc ctccagtgtc   1860
acggtcactc gcagctaccg cagtgtgggg ggcagtgggg gtgcagcttc ggggacaat   1920
ctggtcaccc gctcctacct cctgggcaac tccagccccc gaacccagag cccccagaac   1980
tgcagcatct tataa                                                    1995
```

<210> SEQ ID NO 22
<211> LENGTH: 664
<212> TYPE: PRT
<213> ORGANISM: Homo sapiens

<400> SEQUENCE: 22

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys

```
                    20                  25                  30
Glu Asp Leu Gln Glu Leu Asn Asp Arg Leu Ala Val Tyr Ile Asp Arg
                35                  40                  45

Val Arg Ser Leu Glu Thr Glu Asn Ala Gly Leu Arg Leu Arg Ile Thr
        50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
            115                 120                 125

Ala Ala Gln Ala Arg Leu Lys Asp Leu Glu Ala Leu Leu Asn Ser Lys
        130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
            195                 200                 205

Asn Ile Tyr Ser Glu Glu Leu Arg Glu Thr Lys Arg Arg His Glu Thr
        210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
            275                 280                 285

His Glu Glu Leu Gln Gln Ser Arg Ile Arg Ile Asp Ser Leu Ser Ala
        290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
        370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445
```

Gly Lys Phe Val Arg Leu Arg Asn Lys Ser Asn Glu Asp Gln Ser Met
    450                 455                 460
Gly Asn Trp Gln Ile Lys Arg Gln Asn Gly Asp Asp Pro Leu Leu Thr
465                 470                 475                 480
Tyr Arg Phe Pro Pro Lys Phe Thr Leu Lys Ala Gly Gln Val Val Thr
                485                 490                 495
Ile Trp Ala Ala Gly Ala Gly Ala Thr His Ser Pro Pro Thr Asp Leu
            500                 505                 510
Val Trp Lys Ala Gln Asn Thr Trp Gly Cys Gly Asn Ser Leu Arg Thr
        515                 520                 525
Ala Leu Ile Asn Ser Thr Gly Glu Glu Val Ala Met Arg Lys Leu Val
    530                 535                 540
Arg Ser Val Thr Val Val Glu Asp Asp Glu Asp Glu Asp Gly Asp Asp
545                 550                 555                 560
Leu Leu His His His His Gly Ser His Cys Ser Ser Ser Gly Asp Pro
                565                 570                 575
Ala Glu Tyr Asn Leu Arg Ser Arg Thr Val Leu Cys Gly Thr Cys Gly
            580                 585                 590
Gln Pro Ala Asp Lys Ala Ser Ala Ser Gly Ser Gly Ala Gln Val Gly
        595                 600                 605
Gly Pro Ile Ser Ser Gly Ser Ser Ala Ser Ser Val Thr Val Thr Arg
    610                 615                 620
Ser Tyr Arg Ser Val Gly Gly Ser Gly Gly Ser Phe Gly Asp Asn
625                 630                 635                 640
Leu Val Thr Arg Ser Tyr Leu Leu Gly Asn Ser Ser Pro Arg Thr Gln
                645                 650                 655
Ser Pro Gln Asn Cys Ser Ile Leu
            660

<210> SEQ ID NO 23
<211> LENGTH: 1995
<212> TYPE: DNA
<213> ORGANISM: Homo sapiens

<400> SEQUENCE: 23
atggagaccc cgtcccagcg gcgcgccacc cgcagcgggg cgcaggccag ctccactccg     60
ctgtcgccca cccgcatcac ccggctgcag gagaaggagg acctgcagga gctcaatgat    120
cgcttggcgg tctacatcga ccgtgtgcgc tcgctggaaa cggagaacgc agggctgcgc    180
cttcgcatca ccgagtctga agaggtggtc agccgcgagg tgtccggcat caaggccgcc    240
tacgaggccg agctcgggga tgcccgcaag acccttgact cagtagccaa ggagcgcgcc    300
cgcctgcagc tggagctgag caaagtgcgt gaggagttta aggagctgaa agcgcgcaat    360
accaagaagg agggtgacct gatagctgct caggctcggc tgaaggacct ggaggctctg    420
ctgaactcca aggaggccgc actgagcact gctctcagtg agaagcgcac gctggagggc    480
gagctgcatg atctgcgggg ccaggtggcc aagcttgagg cagccctagg tgaggccaag    540
aagcaacttc aggatgagat gctgcggcgg gtggatgctg agaacaggct gcagaccatg    600
aaggaggaac tggacttcca agaaaacatc tacagtgagg agctgcgtga ccaagcgc     660 cgtcatgaga cccgactggt ggagattgac aatgggaagc agcgtgagtt tgagagccgg    720
ctggcggatg cgctgcagga actgcgggcc agcatgagg accaggtgga gcagtataag    780
aaggagctgg agaagactta ttctgccaag ctggacaatg ccaggcagtc tgctgagagg    840

```
aacagcaacc tggtggggc tgcccacgag gagctgcagc agtcgcgcat ccgcatcgac    900
agcctctctg cccagctcag ccagctccag aagcagctgg cagccaagga ggcgaagctt    960
cgagacctgg aggactcact ggcccgtgag cgggacacca gccggcggct gctggcggaa   1020
aaggagcggg agatggccga gatgcgggca aggatgcagc agcagctgga cgagtaccag   1080
gagcttctgg acatcaagct ggccctggac atggagatcc acgcctaccg caagctcttg   1140
gagggcgagg aggagaggct acgcctgtcc cccagcccta cctcgcagcg cagccgtggc   1200
cgtgcttcct ctcactcatc ccagacacag ggtgggggca gcgtcaccaa aaagcgcaaa   1260
ctggagtcca ctgagagccg cagcagcttc tcacagcacg cacgcactag cgggcgcgtg   1320
gccgtggagg aggtggatga ggagggcaag tttgtccggc tgcgcaacaa gtccaatgag   1380
gaccagtcca tggcaattg gcagatcaag cgccagaatg gagatgatcc cttgctgact   1440
taccggttcc caccaaagtt caccctgaag gctgggcagg tggtgacgat ctgggctgca   1500
ggagctgggg ccacccacag cccccctacc gacctggtgt ggaaggcaca gaacacctgg   1560
ggctgcggga acagcctgcg tacggctctc atcaactcca ctggggaaga agtggccatg   1620
cgcaagctgg tgcgctcagt gactgtggtt gaggacgacg aggatgagga tggagatgac   1680
ctgctccatc accaccacgg ctcccactgc agcagctcgg gaaccccgc tgagtacaac    1740
ctgcgctcgc gcaccgtgct gtgcgggacc tgcgggcagc ctgccgacaa ggcatctgcc   1800
agcggctcag gagcccaggt gggcggaccc atctcctctg gctcttctgc ctccagtgtc   1860
acggtcactc gcagctaccg cagtgtgggg ggcagtgggg gtggcagctt cggggacaat   1920
ctggtcaccc gctcctacct cctgggcaac tccagccccc gaacccagag ccccagaac    1980
tcaagcatca tgtaa                                                    1995
```

<210> SEQ ID NO 24
<211> LENGTH: 664
<212> TYPE: PRT
<213> ORGANISM: Homo sapiens

<400> SEQUENCE: 24

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
```

```
                165                 170                 175
Gly Glu Ala Lys Lys Gln Leu Gln Asp Glu Met Leu Arg Arg Val Asp
                180                 185                 190

Ala Glu Asn Arg Leu Gln Thr Met Lys Glu Glu Leu Asp Phe Gln Lys
            195                 200                 205

Asn Ile Tyr Ser Glu Glu Leu Arg Glu Thr Lys Arg Arg His Glu Thr
        210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590
```

Gln Pro Ala Asp Lys Ala Ser Ala Ser Gly Ser Gly Ala Gln Val Gly
            595                 600                 605

Gly Pro Ile Ser Ser Gly Ser Ser Ala Ser Ser Val Thr Val Thr Arg
        610                 615                 620

Ser Tyr Arg Ser Val Gly Gly Ser Gly Gly Ser Phe Gly Asp Asn
625                 630                 635                 640

Leu Val Thr Arg Ser Tyr Leu Leu Gly Asn Ser Ser Pro Arg Thr Gln
            645                 650                 655

Ser Pro Gln Asn Ser Ser Ile Met
            660

<210> SEQ ID NO 25
<211> LENGTH: 1845
<212> TYPE: DNA
<213> ORGANISM: Homo sapiens

<400> SEQUENCE: 25

| | | | | | | |
|---|---|---|---|---|---|---|
| atggagaccc | cgtcccagcg | gcgcgccacc | cgcagcgggg | cgcaggccag | ctccactccg | 60 |
| ctgtcgccca | cccgcatcac | ccggctgcag | gagaaggagg | acctgcagga | gctcaatgat | 120 |
| cgcttggcgg | tctacatcga | ccgtgtgcgc | tcgctggaaa | cggagaacgc | agggctgcgc | 180 |
| cttcgcatca | ccgagtctga | agaggtggtc | agccgcgagg | tgtccggcat | caaggccgcc | 240 |
| tacgaggccg | agctcgggga | tgcccgcaag | acccttgact | cagtagccaa | ggagcgcgcc | 300 |
| cgcctgcagc | tggagctgag | caaagtgcgt | gaggagttta | aggagctgaa | agcgcgcaat | 360 |
| accaagaagg | agggtgacct | gatagctgct | caggctcggc | tgaaggacct | ggaggctctg | 420 |
| ctgaactcca | aggaggccgc | actgagcact | gctctcagtg | agaagcgcac | gctggagggc | 480 |
| gagctgcatg | atctgcgggg | ccaggtggcc | aagcttgagg | cagccctagg | tgaggccaag | 540 |
| aagcaacttc | aggatgagat | gctgcggcgg | gtggatgctg | agaacaggct | gcagaccatg | 600 |
| aaggaggaac | tggacttcca | gaagaacatc | tacagtgagg | agctgcgtga | gaccaagcgc | 660 |
| cgtcatgaga | cccgactggt | ggagattgac | aatgggaagc | agcgtgagtt | tgagagccgg | 720 |
| ctggcggatg | cgctgcagga | actgcgggcc | cagcatgagg | accaggtgga | gcagtataag | 780 |
| aaggagctgg | agaagactta | ttctgccaag | ctggacaatg | ccaggcagtc | tgctgagagg | 840 |
| aacagcaacc | tggtggggc | tgcccacgag | gagctgcagc | agtcgcgcat | ccgcatcgac | 900 |
| agcctctctg | cccagctcag | ccagctccag | aagcagctgg | cagccaagga | ggcgaagctt | 960 |
| cgagacctgg | aggactcact | ggcccgtgag | cgggacacca | gccggcggct | gctggcggaa | 1020 |
| aaggagcggg | agatggccga | gatgcgggca | aggatgcagc | agcagctgga | cgagtaccag | 1080 |
| gagcttctgg | acatcaagct | ggccctggac | atggagatcc | acgcctaccg | caagctcttg | 1140 |
| gagggcgagg | aggagaggct | acgcctgtcc | cccagcccta | cctcgcagcg | cagccgtggc | 1200 |
| cgtgcttcct | ctcactcatc | ccagacacag | ggtggggca | gcgtcaccaa | aaagcgcaaa | 1260 |
| ctggagtcca | ctgagagccg | cagcagcttc | tcacagcacg | cacgcactag | cgggcgcgtg | 1320 |
| gccgtggagg | aggtggatga | ggagggcaag | tttgtccggc | tgcgcaacaa | gtccaatgag | 1380 |
| gaccagtcca | tggcaattg | gcagatcaag | cgccagaatg | agatgatcc | cttgctgact | 1440 |
| taccggttcc | caccaaagtt | caccctgaag | gctgggcagg | tggtgacgat | ctgggctgca | 1500 |
| ggagctgggg | ccacccacag | cccccctacc | gacctggtgt | ggaaggcaca | gaacacctgg | 1560 |
| ggctgcggga | acagctgcg | tacggctctc | atcaactcca | ctggggaaga | agtggccatg | 1620 |
| cgcaagctgg | tgcgctcagt | gactgtggtt | gaggacgacg | aggatgagga | tggagatgac | 1680 |

```
ctgctccatc accaccacgg ctcccactgc agcagctcgg gggacccccgc tgagtacaac    1740 ctgcgctcgc gcaccgtgct gtgcgggacc tgcgggcagc ctgccgacaa ggcatctgcc    1800
agcggctcag gagcccagag ccccccagaac tgcagcatca tgtaa                   1845
```

<210> SEQ ID NO 26
<211> LENGTH: 614
<212> TYPE: PRT
<213> ORGANISM: Homo sapiens

<400> SEQUENCE: 26

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
```

```
                    340              345              350
Gln Gln Gln Leu Asp Glu Tyr Gln Glu Leu Leu Asp Ile Lys Leu Ala
            355                  360                  365

Leu Asp Met Glu Ile His Ala Tyr Arg Lys Leu Leu Glu Gly Glu Glu
        370                  375              380

Glu Arg Leu Arg Leu Ser Pro Ser Pro Thr Ser Gln Arg Ser Arg Gly
385                  390                  395                  400

Arg Ala Ser Ser His Ser Ser Gln Thr Gln Gly Gly Ser Val Thr
                405                  410                  415

Lys Lys Arg Lys Leu Glu Ser Thr Glu Ser Arg Ser Ser Phe Ser Gln
            420                  425                  430

His Ala Arg Thr Ser Gly Arg Val Ala Val Glu Glu Val Asp Glu Glu
        435                  440                  445

Gly Lys Phe Val Arg Leu Arg Asn Lys Ser Asn Glu Asp Gln Ser Met
    450                  455                  460

Gly Asn Trp Gln Ile Lys Arg Gln Asn Gly Asp Asp Pro Leu Leu Thr
465                  470                  475                  480

Tyr Arg Phe Pro Pro Lys Phe Thr Leu Lys Ala Gly Gln Val Val Thr
                485                  490                  495

Ile Trp Ala Ala Gly Ala Gly Ala Thr His Ser Pro Pro Thr Asp Leu
            500                  505                  510

Val Trp Lys Ala Gln Asn Thr Trp Gly Cys Gly Asn Ser Leu Arg Thr
        515                  520                  525

Ala Leu Ile Asn Ser Thr Gly Glu Glu Val Ala Met Arg Lys Leu Val
    530                  535                  540

Arg Ser Val Thr Val Val Glu Asp Asp Glu Asp Gly Asp Asp
545                  550                  555                  560

Leu Leu His His His Gly Ser His Cys Ser Ser Gly Asp Pro
                565                  570                  575

Ala Glu Tyr Asn Leu Arg Ser Arg Thr Val Leu Cys Gly Thr Cys Gly
            580                  585                  590

Gln Pro Ala Asp Lys Ala Ser Ala Ser Gly Ser Gly Ala Gln Ser Pro
        595                  600                  605

Gln Asn Cys Ser Ile Met
    610

<210> SEQ ID NO 27
<211> LENGTH: 1845
<212> TYPE: DNA
<213> ORGANISM: Homo sapiens

<400> SEQUENCE: 27
atggagaccc cgtcccagcg gcgcgccacc cgcagcgggg cgcaggccag ctccactccg      60
ctgtcgccca cccgcatcac ccggctgcag gagaaggagg acctgcagga gctcaatgat     120
cgcttggcgg tctacatcga ccgtgtgcgc tcgctggaaa cggagaacgc agggctgcgc     180
cttcgcatca ccgagtctga gaggtggtc agccgcgagg tgtccggcat caaggccgcc     240
tacgaggccg agctcgggga tgcccgcaag acccttgact cagtagccaa ggagcgcgcc     300
cgcctgcagc tggagctgag caaagtgcgt gaggagttta aggagctgaa agcgcgcaat     360
accaagaagg agggtgacct gatagctgct caggctcggc tgaaggacct ggaggctctg     420
ctgaactcca aggaggccgc actgagcact gctctcagtg agaagcgcac gctggagggc     480
gagctgcatg atctgcgggg ccaggtggcc aagcttgagg cagccctagg tgaggccaag     540
```

```
aagcaacttc aggatgagat gctgcggcgg gtggatgctg agaacaggct gcagaccatg    600
aaggaggaac tggacttcca gaagaacatc tacagtgagg agctgcgtga gaccaagcgc    660
cgtcatgaga cccgactggt ggagattgac aatgggaagc agcgtgagtt tgagagccgg    720
ctggcggatg cgctgcagga actgcgggcc cagcatgagg accaggtgga gcagtataag    780
aaggagctgg agaagactta ttctgccaag ctggacaatg ccaggcagtc tgctgagagg    840
aacagcaacc tggtggggc tgcccacgag gagctgcagc agtcgcgcat ccgcatcgac    900
agcctctctg cccagctcag ccagctccag aagcagctgg cagccaagga ggcgaagctt    960
cgagacctgg aggactcact ggcccgtgag cgggacacca gccggcggct gctggcggaa   1020
aaggagcggg agatggccga gatgcgggca aggatgcagc agcagctgga cgagtaccag   1080
gagcttctgg acatcaagct ggccctggac atggagatcc acgcctaccg caagctcttg   1140
gagggcgagg aggagaggct acgcctgtcc cccagcccta cctcgcagcg cagccgtggc   1200
cgtgcttcct ctcactcatc ccagacacag ggtgggggca gcgtcaccaa aaagcgcaaa   1260
ctggagtcca ctgagagccg cagcagcttc tcacagcacg cacgcactag cgggcgcgtg   1320
gccgtggagg aggtggatga ggagggcaag tttgtccggc tgcgcaacaa gtccaatgag   1380
gaccagtcca tgggcaattg gcagatcaag cgccagaatg agatgatcc cttgctgact   1440 taccggttcc caccaaagtt cacctgaag gctgggcagg tggtgacgat ctgggctgca   1500
ggagctgggg ccaccacag ccccctacc gacctggtgt ggaaggcaca gaacacctgg   1560
ggctgcggga acagcctgcg tacggctctc atcaactcca ctggggaaga agtggccatg   1620
cgcaagctgt gcgctcagt gactgtggtt gaggacgacg aggatgagga tggagatgac   1680
ctgctccatc accaccacgg ctcccactgc agcagctcgg gggaccccgc tgagtacaac   1740
ctgcgctcgc gcaccgtgct gtgcgggacc tgcgggcagc tgccgacaa ggcatctgcc   1800 agcggctcag gagcccagag ccccagaac tgcagcatct tataa                     1845
```

<210> SEQ ID NO 28
<211> LENGTH: 614
<212> TYPE: PRT
<213> ORGANISM: Homo sapiens

<400> SEQUENCE: 28

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140
```

```
Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
            165                 170                 175

Gly Glu Ala Lys Lys Gln Leu Gln Asp Glu Met Leu Arg Arg Val Asp
        180                 185                 190

Ala Glu Asn Arg Leu Gln Thr Met Lys Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
            245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
            325                 330                 335

Leu Leu Ala Glu Lys Glu Arg Glu Met Ala Glu Met Arg Ala Arg Met
        340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
            370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
            405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
            485                 490                 495

Ile Trp Ala Ala Gly Ala Gly Ala Thr His Ser Pro Thr Asp Leu
        500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
        530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
```

|  |  | 565 |  |  |  | 570 |  |  |  | 575 |  |
|--|--|--|--|--|--|--|--|--|--|--|--|

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Ser Pro
            595                 600                 605

Gln Asn Cys Ser Ile Leu
        610

<210> SEQ ID NO 29
<211> LENGTH: 1845
<212> TYPE: DNA
<213> ORGANISM: Homo sapiens

<400> SEQUENCE: 29

| | | | | | |
|---|---|---|---|---|---|
| atggagaccc | cgtcccagcg | gcgcgccacc | cgcagcgggg | cgcaggccag | ctccactccg | 60 |
| ctgtcgccca | cccgcatcac | ccggctgcag | gagaaggagg | acctgcagga | gctcaatgat | 120 |
| cgcttggcgg | tctacatcga | ccgtgtgcgc | tcgctggaaa | cggagaacgc | agggctgcgc | 180 |
| cttcgcatca | ccgagtctga | gaggtggtc | agccgcgagg | tgtccggcat | caaggccgcc | 240 |
| tacgaggccg | agctcgggga | tgcccgcaag | acccttgact | cagtagccaa | ggagcgcgcc | 300 |
| cgcctgcagc | tggagctgag | caaagtgcgt | gaggagttta | aggagctgaa | agcgcgcaat | 360 |
| accaagaagg | agggtgacct | gatagctgct | caggctcggc | tgaaggacct | ggaggctctg | 420 |
| ctgaactcca | aggaggccgc | actgagcact | gctctcagtg | agaagcgcac | gctggagggc | 480 |
| gagctgcatg | atctgcgggg | ccaggtggcc | aagcttgagg | cagccctagg | tgaggccaag | 540 |
| aagcaacttc | aggatgagat | gctgcggcgg | gtggatgctg | agaacaggct | gcagaccatg | 600 |
| aaggaggaac | tggacttcca | gaagaacatc | tacagtgagg | agctgcgtga | gaccaagcgc | 660 |
| cgtcatgaga | cccgactggt | ggagattgac | aatgggaagc | agcgtgagtt | tgagagccgg | 720 |
| ctggcggatg | cgctgcagga | actgcgggcc | cagcatgagg | accaggtgga | gcagtataag | 780 |
| aaggagctgg | agaagactta | ttctgccaag | ctggacaatg | ccaggcagtc | tgctgagagg | 840 |
| aacagcaacc | tggtgggggc | tgcccacgag | gagctgcagc | agtcgcgcat | ccgcatcgac | 900 |
| agcctctctg | cccagctcag | ccagctccag | aagcagctgg | cagccaagga | ggcgaagctt | 960 |
| cgagacctgg | aggactcact | ggcccgtgag | cgggacacca | gccggcggct | gctggcggaa | 1020 |
| aaggagcggg | agatggccga | gatgcgggca | aggatgcagc | agcagctgga | cgagtaccag | 1080 |
| gagcttctgg | acatcaagct | ggccctggac | atggagatcc | acgcctaccg | caagctcttg | 1140 |
| gagggcgagg | aggagaggct | acgcctgtcc | cccagcccta | cctcgcagcg | cagccgtggc | 1200 |
| cgtgcttcct | ctcactcatc | ccagacacag | ggtgggggca | gcgtcaccaa | aaagcgcaaa | 1260 |
| ctggagtcca | ctgagagccg | cagcagcttc | tcacagcacg | cacgcactag | cgggcgcgtg | 1320 |
| gccgtggagg | aggtggatga | ggagggcaag | tttgtccggc | tgcgcaacaa | gtccaatgag | 1380 |
| gaccagtcca | tggcaattg | gcagatcaag | cgccagaatg | agatgatcc | cttgctgact | 1440 |
| taccggttcc | caccaaagtt | caccctgaag | gctgggcagg | tggtgacgat | ctgggctgca | 1500 |
| ggagctgggg | ccacccacag | ccccctacc | gacctggtgt | ggaaggcaca | gaacacctgg | 1560 |
| ggctgcggga | acagcctgcg | tacggctctc | atcaactcca | ctggggaaga | agtggccatg | 1620 |
| cgcaagctgg | tgcgctcagt | gactgtggtt | gaggacgacg | aggatgagga | tggagatgac | 1680 |
| ctgctccatc | accaccacgg | ctcccactgc | agcagctcgg | ggaccccgc | tgagtacaac | 1740 |
| ctgcgctcgc | gcaccgtgct | gtgcgggacc | tgcgggcagc | ctgccgacaa | ggcatctgcc | 1800 | agcggctcag gagcccagag cccccagaac tcaagcatca tgtaa            1845

<210> SEQ ID NO 30
<211> LENGTH: 614
<212> TYPE: PRT
<213> ORGANISM: Homo sapiens

<400> SEQUENCE: 30

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

```
Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Val Asp Glu Glu
            435                 440                 445

Gly Lys Phe Val Arg Leu Arg Asn Lys Ser Asn Glu Asp Gln Ser Met
450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
530                 535                 540

Arg Ser Val Thr Val Val Glu Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
                580                 585                 590

Gln Pro Ala Asp Lys Ala Ser Ala Ser Gly Ser Gly Ala Gln Ser Pro
            595                 600                 605

Gln Asn Ser Ser Ile Met
        610

<210> SEQ ID NO 31
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: The X at positions 2 and 3 can be any aliphatic
      amino acid; the X at position 4 can be methionine, serine,
      glutamine, alanine or leucine.

<400> SEQUENCE: 31

Cys Xaa Xaa Xaa
1

<210> SEQ ID NO 32
<211> LENGTH: 4
<212> TYPE: PRT
<213> ORGANISM: Artificial sequence
<220> FEATURE:
<223> OTHER INFORMATION: Synthetic Peptide

<400> SEQUENCE: 32

Cys Ser Ile Met
1
```

```
<210> SEQ ID NO 33
<211> LENGTH: 4
<212> TYPE: PRT
<213> ORGANISM: Artificial sequence
<220> FEATURE:
<223> OTHER INFORMATION: Synthetic Peptide

<400> SEQUENCE: 33

Ser Ser Ile Met
1

<210> SEQ ID NO 34
<211> LENGTH: 4
<212> TYPE: PRT
<213> ORGANISM: Artificial sequence
<220> FEATURE:
<223> OTHER INFORMATION: Synthetic Peptide

<400> SEQUENCE: 34

Cys Ser Ile Leu
1
```

FARNESYLTRANSFERASE INHIBITORS FOR TREATMENT OF LAMINOPATHIES, CELLULAR AGING AND ATHEROSCLEROSIS

CROSS-REFERENCE TO RELATED APPLICATIONS

This is a continuation of co-pending U.S. patent application Ser. No. 13/567,432, filed Aug. 6, 2012; which is a division of U.S. patent application Ser. No. 12/905,838, filed Oct. 15, 2010, which issued as U.S. Pat. No. 8,257,915 on Sep. 4, 2012; which is a division of U.S. patent application Ser. No. 11/828,117, filed Jul. 25, 2007, which issued as U.S. Pat. No. 7,838,531 on Nov. 23, 2010; which is a continuation-in-part of International Application No. PCT/US2006/002977, filed Jan. 27, 2006; which in turn claims the benefit of U.S. Provisional Application No. 60/648,307, filed Jan. 28, 2005 and U.S. Provisional Application No. 60/707,192, filed Aug. 9, 2005; and a continuation-in-part of U.S. Utility application Ser. No. 10/943,400, filed Sep. 17, 2004, which issued as U.S. Pat. No. 7,297,942 on Nov. 20, 2007; which is a continuation of International Application No. PCT/US2003/033058, filed Oct. 17, 2003, which in turn claims the benefit of U.S. Provisional Application No. 60/463,084, filed Apr. 14, 2003, and U.S. Provisional Application No. 60/419,541, filed Oct. 18, 2002. Each of these applications is incorporated herein in their entirety.

FIELD

This disclosure relates to treatment of laminopathies, cellular aging and aging-related conditions, and more particularly to the use of farnesyltransferase inhibitors (FTIs) and other compounds and compositions to treat such conditions. It also relates to methods of identifying agents useful in treating, for instance, laminopathies.

BACKGROUND

Hutchinson-Gilford Progeria Syndrome (HGPS) is a rare genetic disease that affects children in the first decade of life and causes a remarkable phenotype resembling many aspects of aging. Affected children develop an extremely aged appearance, a lack of subcutaneous fat, growth retardation and severe atherosclerosis. Affected children die of premature atherosclerosis at an average age of 13 years. Progeria is a disease in which some, but not all, of its manifestations (in vivo and in vitro) represent a model of accelerated aging (reviewed in Sweeney & Weiss, *Gerontology* 38:139-152, 1992). Clinical features common to progeria and normal aging include alopecia (although the pattern of hair loss differs), sclerodermatosis, atherosclerosis, lipofuscin deposition, nail dystrophy, hypermelanosis, decreased adipose tissue, and osteoporosis. Clinical differences include sequelae of maldevelopment in progeria, with coxa valga, distal bone resorption, delayed dentition, facial disproportion, failure to thrive, and short stature. Features of aging that are absent in progeria include neurosensory decline such as Alzheimer's disease, dementia, hearing loss, and presbyopia.

Recently, the gene responsible for HGPS was identified, and HGPS joined a group of syndromes—the laminopathies—all of which have an underlying defect in the lamin A/C gene (LMNA) (Eriksson et al., *Nature* 423:293-298, 2003). LMNA codes for the lamin A and lamin C isoforms, which differ due to alternate splicing, as well as the Δ10 isoform found in sperm. The lamins are a component of the nuclear lamina, a fibrous matrix located at the interior of the nuclear membrane, responsible for nuclear integrity and organization. In addition, lamins are also present in the nucleoplasm and may be involved in more complex spatial organization of the nucleus. They play a role in a wide array of nuclear processes, including transcription, replication, chromatin organization, nuclear shape, cell division, and cell cycle functions (Gruenbaum et al., *J Struct Biol* 129:313-23, 2000; Gruenbaum et al., *Nat. Rev. Mol. Cell Biol.* 6:21-31, 2005). The LMNA gene is primarily expressed in differentiated tissues in the fetus and adult and may be important in maintaining the differentiated state (Rober et al., *Development* 105:365-378, 1989). In fact, lamin A expression is down-regulated in many tumors, perhaps as part of the loss of differentiation seen in those tumors (Muller et al., *Leukemia* 8:940-945, 1994).

The pre-lamin A protein contains a CAAX box (SEQ ID NO: 31) at the carboxy terminus, which is an invariant cysteine followed by two aliphatic amino acids with the X denoting the terminal amino acid. The CAAX box signals for isoprenylation, the addition of a 15-carbon farnesyl isoprenoid lipid group to the cysteine by the enzyme farnesyltransferase (FTase) or a 20-carbon geranylgeranyl isoprenoid lipid by geranylgeranyltransferase I (GGTaseI) (Beck et al., *J. Cell Biol.* 110:1489-1499, 1990). The final amino acid defines the specificity for the addition of the isoprenyl group with methionine, serine, glutamine, or alanine signaling farnesylation and leucine signaling the addition of a 20-carbon geranylgeranyl isoprenoid group catalyzed by the structurally related enzyme GGTase I (Moores et al., *J Biol Chem* 266: 14603-14610, 1991; Cox & Der, *Curr. Opin. Pharmacol.* 2:388-393, 2002). The native lamin A CAAX box (SEQ ID NO: 31) consists of CSIM (cysteine, serine, isoleucine, methionine) (SEQ ID NO: 32). Farnesylation, together with subsequent CAAX-signaled modifications, promote prelamin A association with the nuclear membrane (Hennekes & Nigg, *J. Cell Sci.* 107:1019-1029, 1994). Farnesylation is a permanent modification; once a farnesyl group is added to a protein, it remains attached to that residue for the life of the protein. Following farnesylation, the terminal three AAX amino acids are removed, and the C-terminal isoprenylated cysteine undergoes methyl esterification (Hennekes & Nigg, *J. Cell Sci.* 107:1019-1029, 1994). While both B-type lamins and lamin A are farnesylated and carboxymethylated, unique to lamin A is a second cleavage that occurs inside the nucleus causing the removal of an additional 15 C-terminal amino acids from the mature protein, including the farnesylated cysteine. Because farnesylation is a permanent post-translational modification, proteolytic cleavage of the farnesylated cysteine is necessary for full processing of the prelamin A protein to mature lamin A, and for its correct subcellular localization and function. Thus, this final cleavage step and the resulting loss of the farnesyl anchor presumably releases prelamin A from the nuclear membrane and allows it to be inserted into the nuclear lamina. In HGPS, although preprogerin can be farnesylated, its internal deletion of amino acids 606-656 removes the endoprotease recognition site necessary for executing the final cleavage step. This final cleavage step appears to be important for normal function as mutations in ZMPSTE24 cause a severe form of mandibuloacral dysplasia (MADB), one of the laminopathies which is phenotypically similar to HGPS (Agarwal et al., *Hum. Mol. Genet.* 12:1995-2001, 2003). ZMPSTE24 is the human homolog of yeast STE 24 and is responsible for the final cleavage of lamin A that removes the 15 terminal amino acids (Pendas et al., *Nat. Genet.* 31:94-99, 2002).

Nearly all HGPS patients have the same silent mutation (G608G) creating an abnormal splice donor site in exon 11 of the LMNA gene (Eriksson et al., *Nature* 423:293-298, 2003), which causes a 150 base pair mRNA deletion in the lamin A transcript. The result of the mis-splicing is a protein missing 50 amino acids near the C-terminus (henceforth called "pre-progerin" prior to posttranslational processing and "progerin" after post-translational processing). The deleted region includes the protein cleavage site that normally removes the C-terminal 15 amino acids, including the farnesylated cysteine. The deleted region also contains two potential cyclin-dependent kinase target serines (652 and 657) that may be involved in dissociation and reassociation of the nuclear membrane at each cell division (Sinensky et al., *J Cell Sci* 107(Pt 1):61-7, 1994; Kilic et al., *J Biol Chem* 272(8):5298-304, 1997) and it may affect molecular solubility (Hennekes & Nigg, *J Cell Sci*. 107:1019-29, 1994).

SUMMARY OF THE DISCLOSURE

Although it can be farnesylated, the progerin protein cannot be defarnesylated because the characteristic mutation causes deletion of the second cleavage site necessary for binding ZMPSTE24 and effecting defarnesylation (Eriksson et al., *Nature* 423:293-298, 2003). The result is a shortened, aberrant (abnormally) farnesylated protein capable of altering normal lamin A function as a dominant negative, as well as assuming its own aberrant function through its association with the nuclear membrane. Thus, the multisystem disease process and the variety of genes that are affected in HGPS (Csoka et al., *Aging Cell* 3:235-243, 2004) lie downstream of a protein defect that is central to basic cellular function. Other lamin defects also lead to disease processes (generally referred to as laminopathies) due to aberrant properties of the LMNA protein product.

The retention of farnesylation, and potentially other abnormal properties of progerin and other abnormal lamin gene protein products, produces disease. Farnesyltransferase inhibitors (both direct effectors and indirect inhibitors of farnesyltransferase) will prevent farnesylation, inhibit the formation of progerin, cause a decrease in lamin A protein and an increase in prelamin A and preprogerin proteins. Decreasing the amount of aberrant protein will improve disease status in Progeria and other laminopathies (in that the status will be moved towards normal). In addition, altering lamin A using farnesyltransferase inhibitors (both direct effectors and indirect inhibitors) will improve those elements of other diseases and conditions, such as atherosclerosis and aging, in normal individuals that involve lamin A.

The foregoing and other features and advantages will become more apparent from the following detailed description of several embodiments, which proceeds with reference to the accompanying figures.

BRIEF DESCRIPTION OF THE FIGURES

FIG. 6 (panels A-B) shows images of confocal microscopy of transfected cells. Normal fibroblasts were plated on coverslips, transfected, and fixed as in FIG. 4. Localization of GFP-lamin A (panel A) and progerin (panel B) was analyzed using a Zeiss LSM 510 confocal microscope mounted on a Zeiss AXIOVERT® 100M inverted microscope. Three focal planes are shown—top, middle and bottom (from left to right). These images show the location of the GFP-progerin aggregates as thicker regions at the nuclear periphery (B). Fibroblasts expressing normal GFP-lamin A have GFP signal around the nuclear periphery (A).

Cultures were plated in chambered microscope slides 24 hours prior to fixing with 4% paraformaldehyde for nuclear morphology studies. Cells were maintained in three predetermined tetracycline concentrations, 0 mM for full expression (A), 0.05 mM for intermediate expression levels (B), and 8 mM for very low expression levels (C). Using a TET-OFF® expression vector system allowed for modulation of expression levels with tetracycline concentration as demonstrated by immunoblot of cells from the above experiment (D). When GFP-progerin and GFP-LA(L647R) mutant was stably expressed in normal fibroblasts at intermediate levels (0.05 mg/ml tetracycline), 10 nM FTI substantially reduced the percent abnormal nuclei by 71% and 67%, respectively (p<0.0001) (B). Analysis of nuclear morphology was performed in a double blinded fashion with at least 70 cells analyzed per sample.

Figure 12:
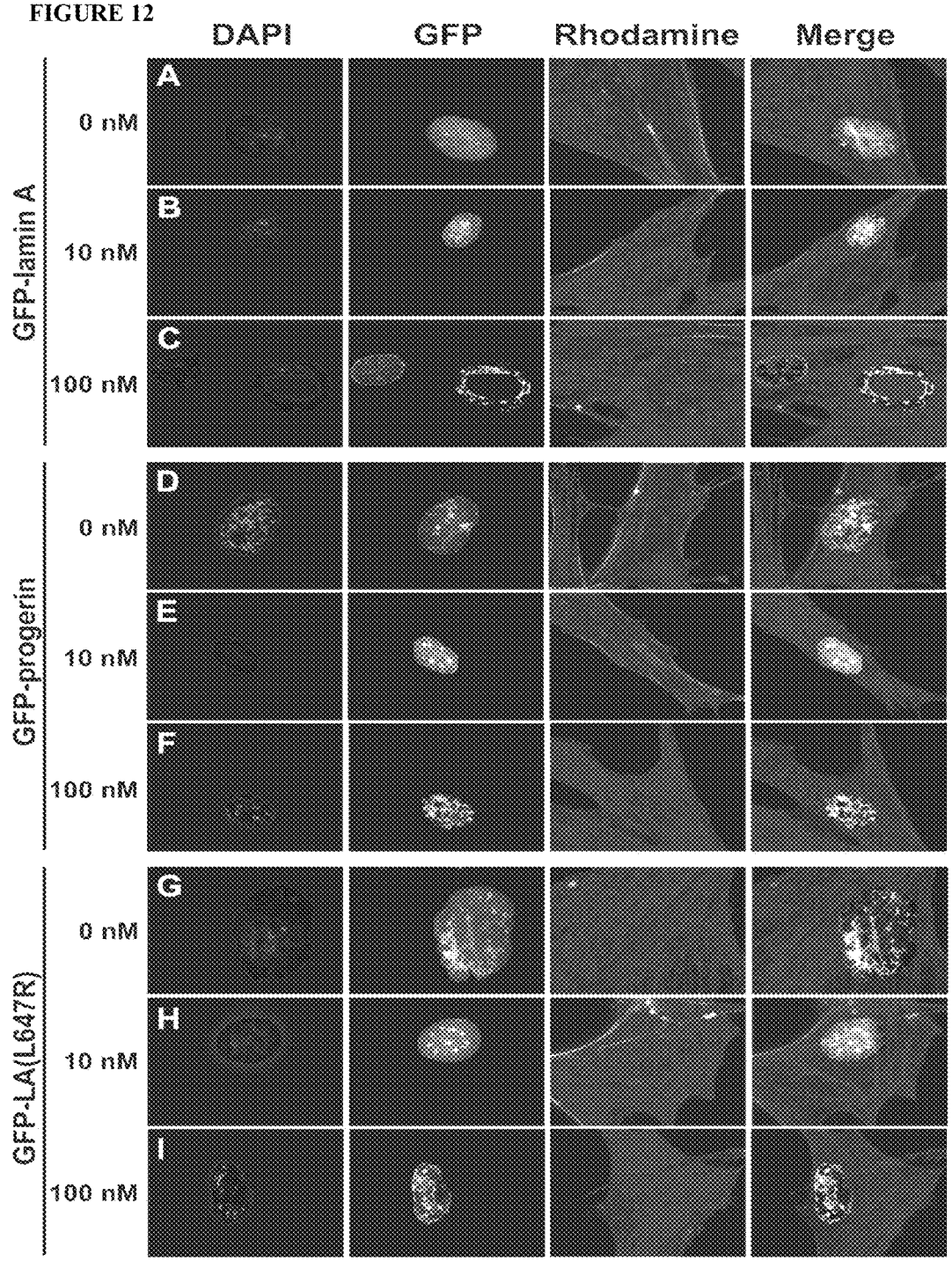

FIG. 12 (panels A-I) illustrates the effect of FTI on the distribution of GFP signal in normal fibroblasts (GM08398) expressing GFP-lamin A (panels A, B and C), GFP-progerin (D, E and F) and GFP-LA(L647R) (G, H, and I) using a retroviral TET-OFF® expression vector system with various FTI concentrations. Fibroblasts were maintained in medium with 0 nM (A, D, G), 10 nM (B, E, and H) or 100 nM (C, F and I) FTI for six days. Expression levels of the GFP fusions were maintained at levels similar to endogenous levels of lamin A by the addition of 0.05 mg/ml tetracycline. Signals were visualized with a Zeiss AXIOPHOT™ Fluorescent microscope and imaging was performed using the Olympus DP70 Digital Camera System.

FIG. 13 includes the maps of three constructs discussed in Examples 5 and 6. MAP 1 illustrates a representative cDNA construct expressing EGFP-labeled lamin A, with or without the 150-nucleotide deletion used to mimic HGPS lamin A. The construct is expressed under the control of a CMV promoter, and also contains a myc epitope tag. MAP 2 illustrates a representative minigene construct expressing EGFP-labeled lamin A, with or without the 150-nucleotide deletion used to mimic HGPS lamin A. The construct is expressed under the control of a CMV promoter, and also contains a myc epitope tag. MAP 3 illustrates a representative tet-inducible minigene construct expressing lamin A, with or without the 150-nucleotide deletion used to mimic HGPS lamin A (Tet 75/77-lamin A minigene constructs). One specific example of a Tet-inducible minigene construct is Tet 75-lamin A, which contains the G608G mutation (GCG to GGT) causing partial aberrant splicing from Exon 11 to Exon 12 and deleting 150 nucleotides (corresponding to 50 amino acid residues), thereby producing a progerin-like protein. Another is Tet 77-lamin A, which contains the wild type Lamin A minigene.

FIG. 14 is a series of schematic drawings of lamin A and mutant lamin A expression constructs.

Figure 15:
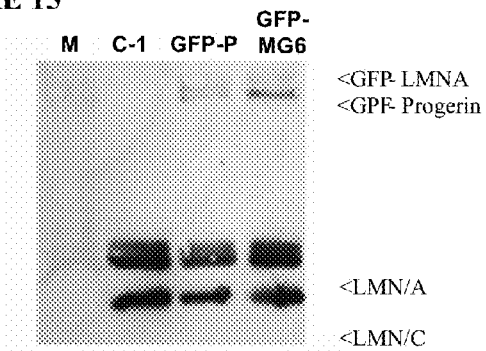

FIG. 15 is a Western blot illustrating expression of Progerin from fibroblasts transfected with Progerin cDNA and minigene: M=Molecular weight marker; C1 Normal Fibroblast untransfected; GFP-P=Normal Fibroblast transfected with complete Progerin cDNA construct; GFP-MG6=Normal Fibroblast transfected with MG6-minigene which shows the splicing event.

Figure 16:
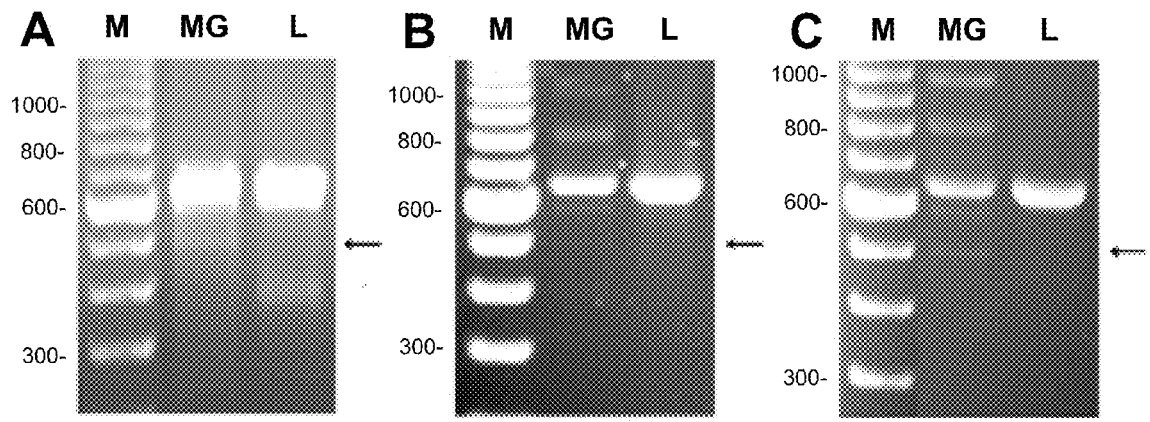

FIG. 16 (panels A-C) is a series of digital scans of nucleic acid gels, showing processing of lamin and progerin minigene constructs in human vascular cells. FIG. 16A shows results in EC; FIG. 16B shows coronary artery SMC; and FIG. 16C shows radial artery SMC. Each cell type expresses and processes progerin after minigene transcript transfection. Cells were electroporated and exposed to either Progerin minigene (MG) or LMNA-lamin A (L). Arrows indicate the 489 base pair band of interest in the MG lane, produced by the Progeria gene which indicates a splicing event occurring in VSMC and EC. Other bands indicate incomplete splicing of the minigene.

Figure 17:
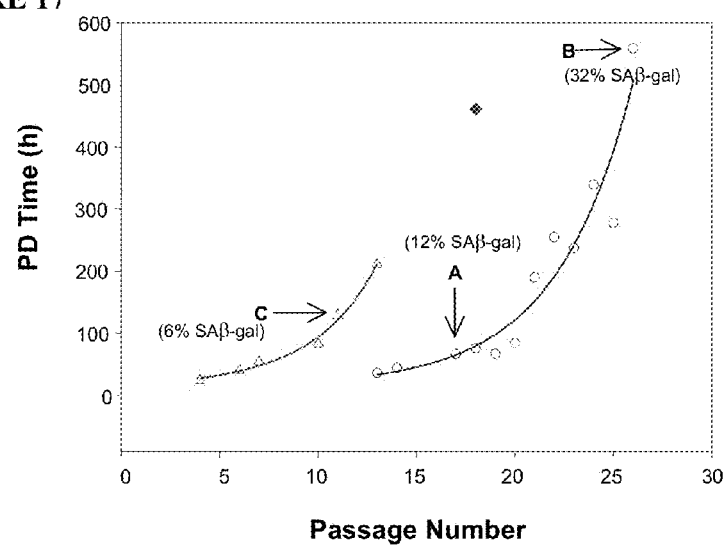

FIG. 17 shows population doubling times of cultured human dermal fibroblast lines. Solid lines indicate 4-parameter exponential growth curve fit for HGPS (line through triangles) and Normal (line through circles). Passage doubling (PD) time at each passage is indicated by open triangles (HGPS) and open circles (Normal). Filled diamond indicates a second HGPS cell line at later passage for comparison. Corresponding SAβ-gal staining is indicated.

FIG. 18 (panels A-C) Cells were stained with Annexin V for apoptosis, Propidium Iodide (PI) for necrosis, and DAPI for DNA (all 20×). FIG. 18A: Non-apoptotic normal fibroblasts (passage 14) display round nuclei. FIG. 18B: HGPS fibroblasts (passage 14) display apoptosis with underlying nuclei. FIG. 18C: HGPS fibroblasts immortalized with hTERT catalytic subunit of telomerase show no apoptosis (passage 35).

FIG. 19 (panels A-D) Cells were plated on glass coverslips and stained for lamin A/C (upper and lower panels) and DAPI (lower panels). Images were taken under 40× objective and analyzed for nuclear morphology. HGPS cells (B&D) exhibit blebbing of the nuclear envelope whereas Normal cells (A&C) do not.

FIG. 20 Normal (n=6) and HGPS (n=6) fibroblast cell lines were assessed for MMP-3 secretion. MMP-3 secretion from HGPS fibroblasts was significantly (p=0.003) decreased over controls.

Figure 21:
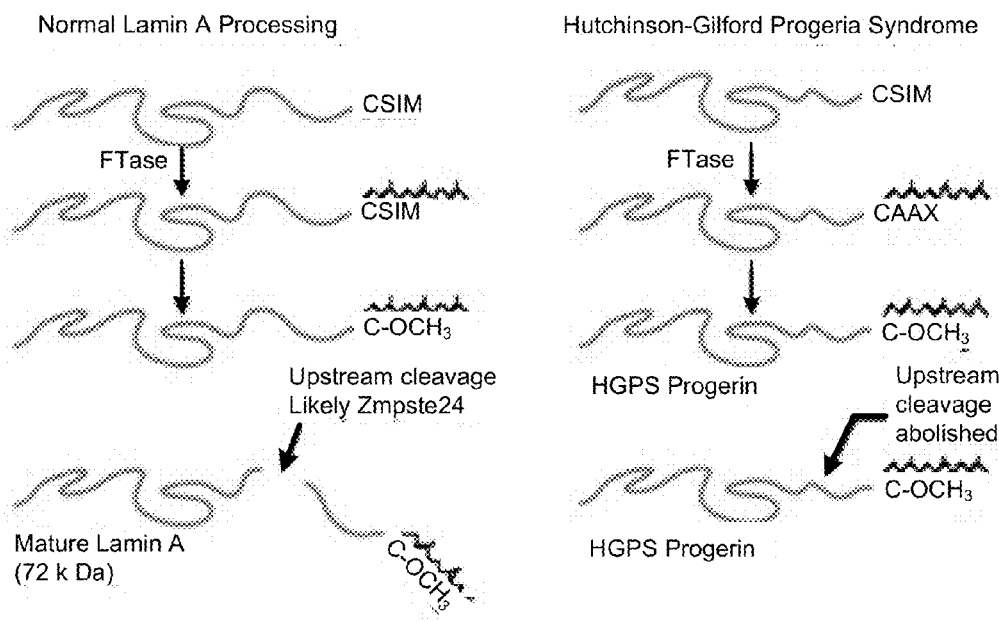

FIG. 21 Translation of the LMNA gene yields the prelamin A protein, which requires posttranslational processing for incorporation into the nuclear lamina. The prelamin protein contains a CAAX box (CSIM) (SEQ ID NO: 31) at the C-terminus signaling isoprenylation, in this case addition of a farnesyl group to the cysteine by the enzyme farnesyltransferase. Following farnesylation, the terminal three amino acids (SIM) are cleaved, and the terminal farnesylated cysteine undergoes methyl esterification. A second cleavage step by the ZMPSTE24 endoprotease then removes the terminal 15 amino acids, including the farnesyl group. This final cleavage step is blocked in progeria.

Figure 22:
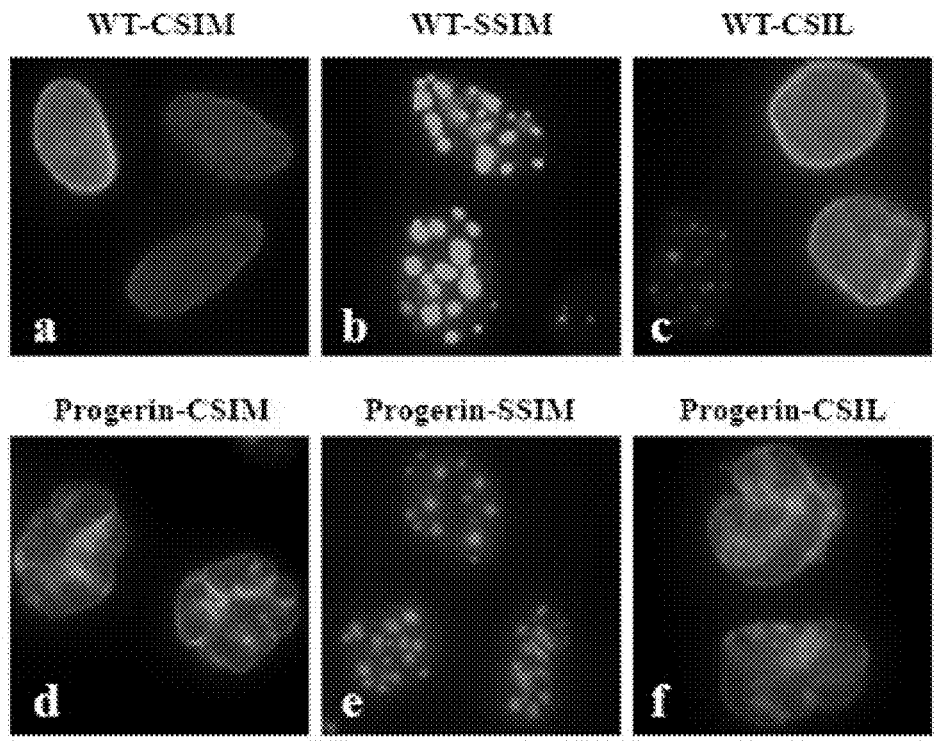

FIG. 22 (panels A-F) Subcellular localization and induction of nuclear blebbing by prenylation mutants of wild-type and progerin lamin A. Transient transfection of HeLa cells with expression vectors encoding the indicated wild-type or progerin lamin A protein. (a) Normal wildtype lamin A-CSIM CAAX motif (SEQ ID NO: 31); (b) wild-type lamin A with the CSIM sequence (SEQ ID NO: 32) mutated to SSIM (SEQ ID NO: 33) to prevent farnesylation (because serine (S) cannot be farnesylated), relocalizing all lamin A into nucleoplasmic aggregates; (c) wild-type lamin A with the CSIM sequence (SEQ ID NO: 32) mutated to CSIL (SEQ ID NO: 34), predicted to be geranylgeranylated by GGTase I, resulting in a mix of nucleoplasmic and nuclear membrane localization; (d) the progerin-CSIM construct recreates the hallmark nuclear blebbing seen in HGPS; (e) when the CSIM (SEQ ID NO: 32) of the progerin-CSIM is mutated to SSIM (SEQ ID NO: 33) (progerin-SSIM), blebbing is prevented, and progerin accumulates in nucleoplasmic aggregates; (f) progerin-CSIL causes blebbing indistinguishable from that of authentic progerin-CSIM. Cells were visualized 48 hours after transfection and photomicrographs were taken at 60× magnification.

Figure 23:
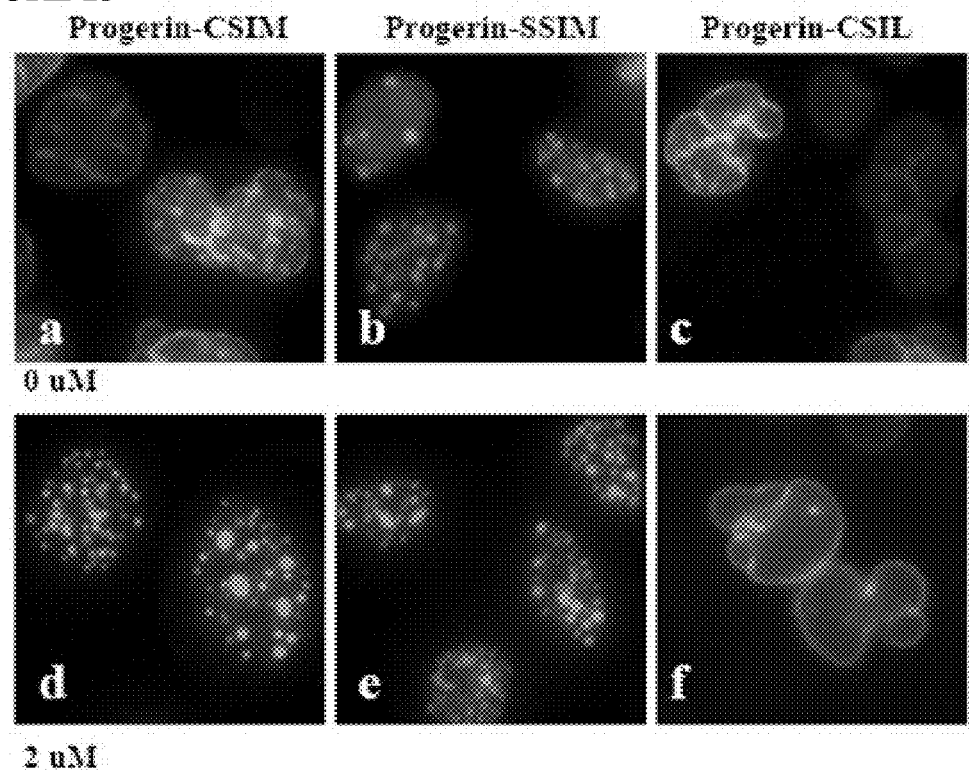

FIG. 23 (panels A-F) FTI treatment prevents nuclear blebbing caused by farnesylated, but not geranylgeranylated, progerin. HeLa cells were transiently transfected with expression vectors encoding either the progerin-CSIM, progerin-SSIM or progerin-CSIL constructs, and were treated with either 0 or 2 μM of the FTI lonafarnib/SCH66336. (a) The progerin-CSIM construct recreates the hallmark nuclear blebbing seen in HGPS, while FTI treatment almost totally abolishes it, and leads to relocalization of progerin into nucleoplasmic aggregates (d); (b) unprocessed progerin-SSIM mimics the phenotype of FTI-treated cells expressing authentic progerin-CSIM, with all progerin relocalized into nucleoplasmic aggregates, and this does not change significantly with treatment (e); (c) progerin-CSIL, predicted to be geranylgeranylated, recreates nuclear blebbing but is resistant to FTI treatment (f). Cells were visualized 48 hours after transfection and photomicrographs were taken at 60× magnification.

Figure 24:
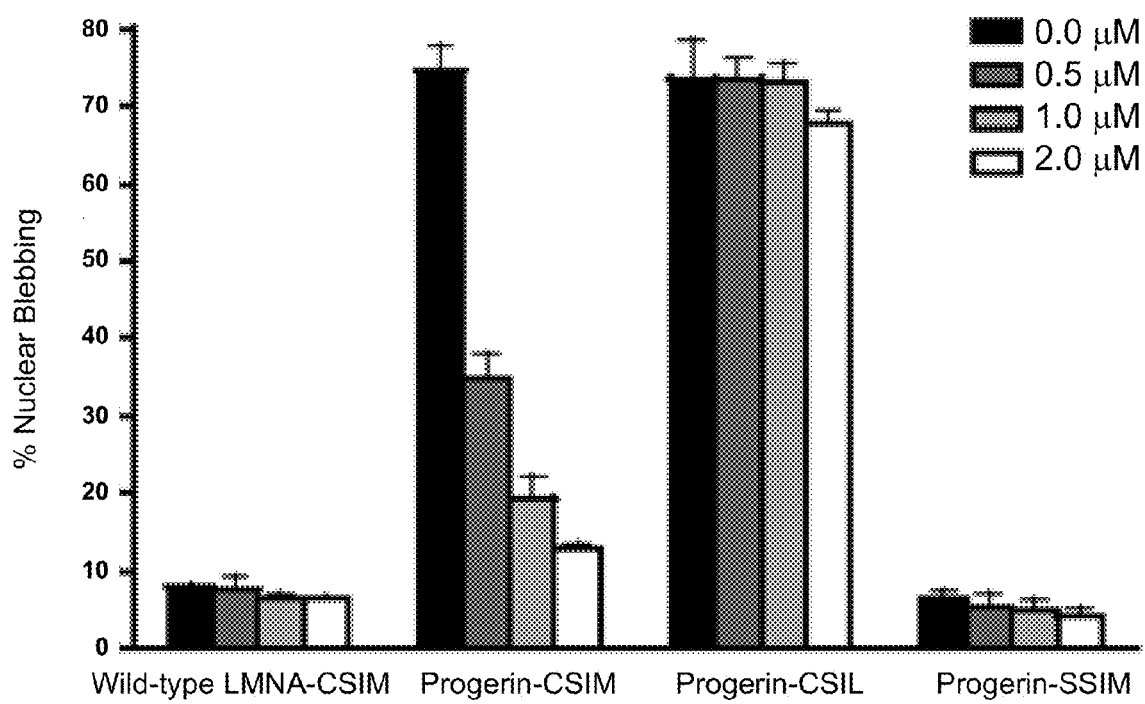

FIG. 24: The percentage of blebbed HeLa nuclei when transiently transfected with the above four constructs and treated with a single dose of lonafarnib/SCH66336 at the time of transfection. Percentages were read by three independent observers, who scored 200 cells for each experiment and were blind to the construct being used. Error bars show the standard error of the mean, and the p-values are for the comparison of the treated cells to the untreated control. Wild-type lamin A-CSIM does not change significantly from the typical 5% nuclear blebbing percentage of normal cells. The progerin-CSIM shows a dramatic dose-response. The progerin-CSIL, expected to be geranylgeranylated, is resistant to inhibition of farnesylation. The progerin-SSIM, which cannot be farnesylated or geranylgeranylated, demonstrates virtually no blebbing.

Figure 25:
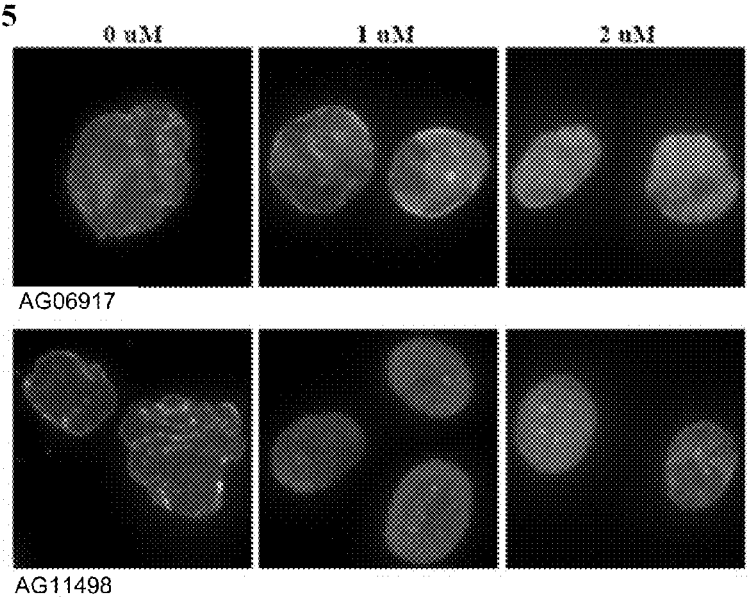

FIG. 25: FTI treatment causes reversion of the nuclear blebbing in two different progerin-expressing HGPS human fibroblasts. Cells were stained with anti-lamin A antibody after being treated for 3 days with either 0, 1, or 2 μM of the FTI lonafarnib/SCH66336 (60×).

Figure 26:
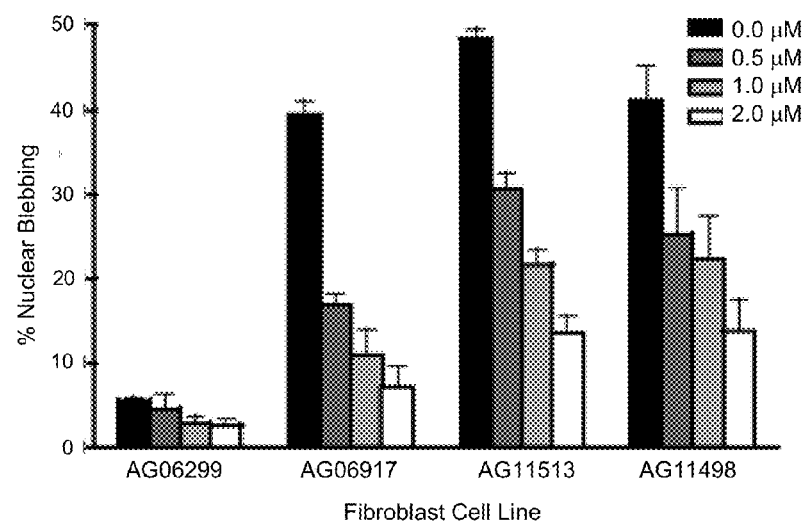

FIG. 26: The percentage of blebbed nuclei when HGPS skin fibroblasts were treated once daily for three days with the above doses of lonafarnib. AG06299 is from the 34 year-old unaffected mother (passage 31) of AG06917, an affected 6 year-old (passage 14). AG11513 is from an affected 8 year-old (passage 7), and AG11498 is from an affected 14 year-old (passage 11). Percentages were read by three independent observers, who scored 200 cells for each experiment and were blind to the genotype of the fibroblasts and the dose of the FTI being used. Error bars show the standard error of the mean, and the p-values are for the comparison of the treated cells to the untreated control.

Figure 27:
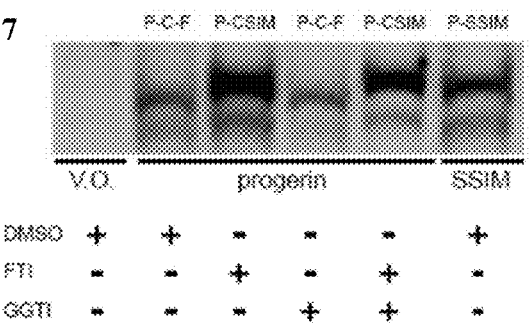

FIG. 27: FTI treatment alone is sufficient to impair progerin processing. NIH-3T3 cells transiently expressing empty vector ("v.o."), or GFP-tagged progerin-CSIM ("Progerin") or GFP-tagged progerin-SSIM ("SSIM") were treated for 48 hours with vehicle (DMSO) or inhibitors of FTase or GGTase I (5 μM FTI-2153 or GGTI-2166, respectively). Total cell lysates were resolved on SDS-PAGE and immunoblotted with anti-GFP to detect GFP-progerin-CSIM or the fully unprocessed mutant GFP-progerin-SSIM. Treatment with FTI, but not GGTI, induces a mobility shift of progerin-CSIM to that of the unprocessed progerin-SSIM, demonstrating that progerin is a FTI target that does not undergo alternative prenylation and modification by GGTase I. Schematic diagrams at the top of each lane indicate the molecular entity that constitutes the major species in each experiment. P=progerin sequence up to CAAX motif (SEQ ID NO: 31); C=cysteine; F=farnesyl group.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file named SeqList.txt, created on Mar. 26, 2013, ~56 KB, which is incorporated by reference herein. Only one strand of each nucleic acid sequence is shown, but the complementary strand is understood as included by any reference to the displayed strand. In the accompanying sequence listing:

SEQ ID NOs: 1 and 2 are primers (laminAF1 and laminAR1, respectively) used to amplify normal and mutant lamin A/C.

SEQ ID NOs: 3-8 are primers used to introduce the L647R mutant into the pRevTRE-GFP-lamin A construct.

SEQ ID NOs: 9 and 10 are a pair of forward and reverse primers.

SEQ ID NOs: 11-18 are primers used to generate lamin A CAAX mutants.

SEQ ID NO: 19 is the CSIM Human lamin A (LMNA) wt mRNA coding sequence (nucleotide residues 213-2207 of GenBank Accession: NM_170707).

SEQ ID NO: 20 is the CSIM LMNA protein translation.

SEQ ID NO: 21 is the CSIL Human lamin A (LMNA) wt mRNA coding sequence (nucleotide residues 213-2207 of GenBank Accession: NM_170707).

SEQ ID NO: 22 is the CSIL LMNA protein translation.

SEQ ID NO: 23 is the SSIM Human lamin A (LMNA) wt mRNA coding sequence (nucleotide residues 213-2207 of GenBank Accession: NM_170707).

SEQ ID NO: 24 is the SSIM LMNA protein translation.

SEQ ID NO: 25 is the CSIM Human lamin A (LMNA) del 150 mRNA coding sequence.

SEQ ID NO: 26 is the CSIM LMNA_del50 protein translation.

SEQ ID NO: 27 is the Human lamin A (LMNA) CSIL del 150 mRNA coding sequence.

SEQ ID NO: 28 is the CSIL LMNA_del50 protein translation.

SEQ ID NO: 29 is the SSIM Human lamin A (LMNA) del 150 mRNA coding sequence.

SEQ ID NO: 30 is the SSIM LMNA_del50 protein translation.

SEQ ID NOs: 31-34 are the CAAX box motif of the prelamin protein and variants thereof.

DETAILED DESCRIPTION

I. Abbreviations
  EC: endothelial cells
  EGFP: enhanced green fluorescent protein
  FPP: farnesyl pyrophosphate
  FTase: farnesyltransferase
  FTI: farnesyltransferase inhibitor
  GFP: green fluorescent protein
  GGTase I: geranylgeranyltransferase
  GGTI: geranylgeranyltransferase inhibitor
  HGPS: Hutchinson-Gilford Progeria Syndrome
  ICC: immunocytochemistry
  LA: lamin A
  LMNA: gene encoding lamin A and lamin C
  MADB: mandibuloacral dysplasia
  MG: minigene
  ORF: open reading frame
  PD: Passage doubling
  RT-PCR: reverse-transcription polymerase chain reaction
  UTRs: untranslated regions
  VSMC: vascular smooth muscle cells II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, we provide the following information concerning some of the terms used herein. Additional information may be found in the literature, including the references cited and incorporated by reference herein.

Abnormal: Deviation from normal characteristics. Normal characteristics can be found in a control, a standard for a population, etc. For instance, where the abnormal condition is a disease condition, such as progeria, a few appropriate sources of normal characteristics might include an individual who is not suffering from the disease (e.g., progeria), a population standard of individuals believed not to be suffering from the disease, etc.

Likewise, abnormal may refer to a condition that is associated with a disease. The term "associated with" includes an increased risk of developing the disease as well as the disease itself. For instance, a certain abnormality (such as an abnormality in an LMNA nucleic acid or Lamin protein expression) can be described as being associated with the biological conditions of progeria and tendency to develop premature aging disease or condition.

An abnormal nucleic acid, such as an abnormal LMNA nucleic acid, is one that is different in some manner to a normal (wildtype) nucleic acid. Such abnormality includes but is not necessarily limited to: (1) a mutation in the nucleic acid (such as a point mutation (e.g., a single nucleotide polymorphism) or short deletion or duplication of a few to several nucleotides); (2) a mutation in the control sequence(s) associated with that nucleic acid such that replication or expression of the nucleic acid is altered (such as the functional inactivation of a promoter); (3) a decrease in the amount or copy number of the nucleic acid in a cell or other biological sample (such as a deletion of the nucleic acid, either through selective gene loss or by the loss of a larger section of a chromosome or under expression of the mRNA); (4) an increase in the amount or copy number of the nucleic acid in a cell or sample (such as a genomic amplification of part or all of the nucleic acid or the overexpression of an mRNA), each compared to a control or standard; and (5) an alteration in a sequence that controls the splicing mechanism, in such a way that either a normal splice signal is inactivated or an abnormal splice signal is created. It will be understood that these types of abnormalities can co-exist in the same nucleic acid or in the same cell or sample; for instance, a genomic-amplified nucleic acid sequence may also contain one or more point mutations. In addition, it is understood that an abnormality in a nucleic acid may be associated with, and in fact may cause, an abnormality in expression of the corresponding protein.

Abnormal protein expression, such as abnormal lamin A protein expression, refers to expression of a protein that is in some manner different to expression of the protein in a normal (wildtype) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (e.g., organ or tissue specific) expression of the protein (such that the protein is not expressed where it would normally be expressed or is expressed where it normally would not be expressed), each compared to a control or standard.

One particular type of protein abnormality that is contemplated herein involves changes in the post-translational processing of a protein. A protein that is abnormally post-translationally processed includes, for instance, proteins that processed in a different way, or to a different extent, than the wild-type (normal) version of the protein. Progerin is an example of an abnormally processed protein; it is not proteolytically processed in the same way as the corresponding wild-type protein, lamin A. In addition, progerin is abnormal in that it remains farnesylated after its processing is completed (to the extent that a cell expressing a nucleic acid encoding progerin processes the protein). This can be referred to as being "constitutively" farnesylated, in that an individual progerin protein remains farnesylated in the context of an otherwise unaltered cell. In contrast, a "normal" lamin A protein is only transiently farnesylated, because full post-translational processing of lamin A eventually results in loss of the farnesyl group from the mature protein (by way of a required proteolytic cleavage step). Progerin can be considered an abnormally farnesylated form of lamin A; other abnormally farnesylated forms of lamins are discussed herein, including forms engineered to lack a proteolytic cleavage site, to lack the farnesylation site, and so forth. Other potential "abnormal" post-translational processing includes changes in other added groups (e.g., methylations, phosphorylations, glycosylations, and so forth), alterations in proteolytic processing, and so forth.

Controls or standards appropriate for comparison to a sample, for the determination of abnormality, include samples believed to be normal as well as laboratory determined values, even though such values are possibly arbitrarily set, and keeping in mind that such values may vary from laboratory to laboratory. Laboratory standards and values may be set based on a known or determined population value and may be supplied in the format of a graph or table that permits easy comparison of measured, experimentally determined values.

Analog, derivative or mimetic: An analog is a molecule that differs in chemical structure from a parent or reference compound, for example a homolog (differing by an incremental change in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a substance related to a base structure, and theoretically derivable from the base structure. A mimetic is a biomolecule that mimics the activity of another biologically active molecule. Biologically active molecules can include chemical structures that mimic the biological activities of a compound, for instance a native siRNA.

Array: An arrangement of molecules, particularly biological macromolecules (such as polypeptides or nucleic acids) in addressable locations on a substrate. The array may be regular (arranged in uniform rows and columns, for instance) or irregular. The number of addressable locations on the array can vary, for example from a few (such as three) to more than 50, 100, 200, 500, 1000, 10,000, or more. A "microarray" is an array that is miniaturized so as to require or benefit from microscopic examination, or other magnification, for its evaluation. Further miniaturization can be used to produce "nanoarrays."

Within an array, each arrayed molecule sample is addressable, in that its location can be reliably and consistently determined within at least two dimensions of the array surface. In ordered arrays, the location of each molecule sample can be assigned to the sample at the time when it is spotted or otherwise applied onto the array surface, and a key may be provided in order to correlate each location with the appropriate target. Often, ordered arrays are arranged in a symmetrical grid pattern, but samples could be arranged in other patterns (e.g., in radially distributed lines, spiral lines, or ordered clusters). Addressable arrays are computer readable, in that a computer can be programmed to correlate a particular address on the array with information (such as hybridization or binding data, including for instance signal intensity). In some examples of computer readable formats, the individual "spots" on the array surface will be arranged regularly in a pattern (e.g., a Cartesian grid pattern) that can be correlated to address information by a computer.

The sample application "spot" on an array may assume many different shapes. Thus, though the term "spot" is used, it refers generally to a localized deposit of nucleic acid, and is not limited to a round or substantially round region. For instance, substantially square regions of mixture application can be used with arrays encompassed herein, as can be regions that are substantially rectangular (such as a slot blot-type application), or triangular, oval, or irregular. The shape of the array substrate itself is also immaterial, though it is usually substantially flat and may be rectangular or square in general shape.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes lamin A, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side of the removed sequence being joined together.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Examples of useful epitope tags include but are not limited to FLAG, T7, HA (hemagglutinin) and myc.

Feature: An addressable spot/element containing a molecule or mixture of molecules on an array. Features may be created by printing the molecule(s), usually within some type of matrix, onto the array platform by a printing device, such as a quill-like pen, or by a touch-less deposition system (see, e.g., Harris et al., *Nature Biotech.* 18:384-385, 2000). Alternatively, in some embodiments the feature can be made by in situ synthesis of the molecule on the array substrate.

Fluorescent protein: A protein that either directly (through its primary, secondary, or tertiary structure) or indirectly (through a co-factor, non-protein chromophore, or a substrate, or due to the addition of a fluor) produces or emits fluorescent light. Non-limiting examples of fluorescent proteins are the green fluorescent protein (GFP; see, for instance, GenBank Accession Number M62654) from the Pacific Northwest jellyfish, *Aequorea victoria* and natural and engineered variants thereof (see, for instance, U.S. Pat. Nos. 5,804,387; 6,090,919; 6,096,865; 6,054,321; 5,625,048; 5,874,304; 5,777,079; 5,968,750; 6,020,192; and 6,146,826; and published international patent application WO 99/64592).

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for exampleCY3® green fluorophore, FITC, and OREGON GREEN® green fluorophore, are characterized by their emission at wavelengths generally in the range of 515-540λ. Red fluorophores, for example TEXAS RED® red fluorophore, CY5® red fluorophore and tetramethylrhodamine, are characterized by their emission at wavelengths generally in the range of 590-690λ.

Examples of fluorophores that may be used are provided in U.S. Pat. No. 5,866,366 to Nazarenko et al., and include for instance: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (TEXAS RED® red fluorophore); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Inhibiting or treating a disease: Inhibiting the full development of a disease, disorder or condition, for example, in a subject who is at risk for a disease such as a laminopathy, an aging-associated disease or condition, atherosclerosis or cardiovascular disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease or condition.

Injectable composition: A pharmaceutically acceptable fluid composition including at least one active ingredient (for instance, a dsRNA). The active ingredient is usually dissolved or suspended in a physiologically acceptable carrier, and the composition can additionally include minor amounts of one or more non-toxic auxiliary substances, such as emulsifying agents, preservatives, and pH buffering agents and the like. Such injectable compositions that are useful for use with the provided nucleotides and proteins are conventional; appropriate formulations are well known in the art.

Isolated: An "isolated" biological component (such as a nucleic acid molecule, protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A composition detectable by (for instance) spectroscopic, photochemical, biochemical, immunochemical, or chemical means. Typical labels include fluorescent proteins or protein tags, fluorophores, radioactive isotopes (including for instance $^{32}P$), ligands, biotin, digoxigenin, chemiluminescent agents, electron-dense reagents (such as metal sols and colloids), and enzymes (e.g., for use in an ELISA), haptens, and proteins or peptides (such as epitope tags) for which antisera or monoclonal antibodies are available. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, John Wiley & Sons, New York (1998). A label often generates a measurable signal, such as radioactivity, fluorescent light or enzyme activity, which can be used to detect and/or quantitate the amount of labeled molecule.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or intersugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with this disclosure are conventional. Martin, *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, e.g., variants in the gene sequence that lead to gene products that are not functionally equivalent. This term also encompasses variations that produce no gene product, an inactive gene product, or increased gene product. The term polymorphism may be used interchangeably with allele or mutation, unless context clearly dictates otherwise.

Polymorphisms can be referred to, for instance, by the nucleotide position at which the variation exists, by the change in amino acid sequence caused by the nucleotide variation, or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth). In the current instance, Mutation 1 is also referred to as G608G(GGC>GGT), indicating that the mutation is in codon 608, that it is silent (in that it causes no change in the encoded amino acid), and that the exact nucleotide sequence change is C to T in the third position of the codon. Similarly, Mutation 2 is also referred to as G608S(GGC>AGC), indicating that the mutation is in codon 608, that it causes an amino acid substitution (glycine to serine), and that the exact nucleotide sequence change is G to A in the first position of the codon.

Probes and primers: A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (*In Molecular Cloning: A Laboratory Manual*, CSHL, New York, 1989) and Ausubel et al. (*In Current Protocols in Molecular Biology*, John Wiley & Sons, New York, 1998).

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Nucleic acid probes and primers can be readily prepared based on the nucleic acid molecules provided in this disclosure. It is also appropriate to generate probes and primers based on fragments or portions of these disclosed nucleic acid molecules, for instance regions that encompass the identified polymorphisms at nucleotide 1822 and nucleotide 1824 within the LMNA coding sequence.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990).

Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of a lamin A-encoding nucleotide or flanking region thereof (a "lamin A primer" or "lamin A probe") will anneal to a target sequence with a higher specificity than a corresponding primer of only 15 nucleotides. Thus, in order to obtain greater specificity, probes and primers can be selected that comprise at least 20, 25, 30, 35, 40, 45, 50 or more consecutive nucleotides of a lamin A nucleotide sequences.

The disclosure thus includes isolated nucleic acid molecules that comprise specified lengths of the lamin A encoding sequence and/or flanking regions. Such molecules may comprise at least about 10, 15, 20, 23, 25, 30, 35, 40, 45 or 50 consecutive nucleotides of these sequences or more, and may be obtained from any region of the disclosed sequences. By way of example, the human LMNA locus, cDNA, ORF, coding sequence and gene sequences (including sequences both upstream and downstream of the LMNA coding sequence) may be apportioned into about halves or quarters based on sequence length, and the isolated nucleic acid molecules (e.g., oligonucleotides) may be derived from the first or second halves of the molecules, or any of the four quarters. The cDNA also could be divided into smaller regions, e.g. about eighths, sixteenths, twentieths, fiftieths and so forth, with similar effect.

In particular embodiments, isolated nucleic acid molecules comprise or overlap at least one residue position designated as being associated with a polymorphism that is predictive of progeria and/or a premature aging disease or condition. Such polymorphism sites include position 1822 (corresponding to the Mutation 2 polymorphism) and position 1824 (corresponding to the Mutation 1 polymorphism).

Protein: A biological molecule, particularly a polypeptide, expressed by a gene and comprised of amino acids.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Specific binding agent: An agent that binds substantially only to a defined target. Thus a lamin A protein-specific binding agent binds substantially only the lamin A protein. As used herein, the term "Lamin protein specific binding agent" includes anti-Lamin protein antibodies (and functional fragments thereof) and other agents (such as soluble receptors) that bind substantially only to a Lamin protein. It is particularly contemplated in specific embodiments that certain Lamin-specific binding agents are specific for one form of Lamin, such as lamin A or lamin C.

Anti-Lamin protein antibodies may be produced using standard procedures described in a number of texts, including Harlow and Lane (*Antibodies, A Laboratory Manual*, CSHL, New York, 1988). The determination that a particular agent binds substantially only to the target protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given target protein binding agent, such as an anti-lamin A protein monoclonal antibody, binds substantially only to the specified target protein.

Shorter fragments of antibodies can also serve as specific binding agents. For instance, FAbs, Fvs, and single-chain Fvs (SCFvs) that bind to lamin A would be lamin A-specific binding agents. These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb')$_2$, the fragment of the antibody obtained by treating whole antibody with the enzyme pepsin without subsequent reduction; (4) F(Ab')$_2$, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals. This term encompasses both known and unknown individuals, such that there is no requirement that a person working with a sample from a subject know who the subject is, or even from where the sample was acquired.

Subject susceptible to a disease or condition: A subject capable of, prone to, or predisposed to developing a disease or condition. It is understood that a subject already having or showing symptoms of a disease or condition is considered "susceptible" since they have already developed it.

Therapeutically effective dose: A dose sufficient to prevent advancement, or to cause regression of the disease, or which is capable of relieving symptoms caused by the disease, such as a laminopathy or age related disease or condition (for instance, atherosclerosis). For example, a therapeutically effective amount of an inhibitor can vary from about 0.1 nM per kilogram (kg) body weight to about 1 µM per kg body weight, such as about 1 nM to about 500 nM per kg body weight, or about 5 nM to about 50 nM per kg body weight. The exact dose is readily determined by one of skill in the art based on the potency of the specific compound, the age, weight, sex and physiological condition of the subject.

Transfected or Transformed: A process by which a nucleic acid molecule is introduced into live cells, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

A first embodiment is a method of reducing at least one cellular defect in a cell from a subject susceptible to a disease or condition characterized by farnesylation of an abnormally farnesylated form of a lamin, comprising administering to the cell a therapeutically effective dose of a farnesyltransferase inhibitor (FTI). In examples of such methods, the cellular defect involves mis-localization of a farnesylated lamin, mis-localization of a non-farnesylated lamin, nuclear membrane disruption, aggregation of lamin, nuclear lobulation, nuclear blebbing, cytoskeleton disruption, early senescence, apoptosis, reduced secretion of MMP-3, or two or more thereof.

Examples of diseases or conditions characterized by farnesylation of an abnormally farnesylated form of a lamin include laminopathies, which include but are not limited to Hutchinson-Gilford Progeria Syndrome (HGPS), progeria, muscular dystrophy, Charcot-Marie-Tooth disorder, and Werner syndrome.

There is also provided a method of treating a subject having or predisposed to a laminopathy, which method involves administering to the subject an effective amount of at least one FTI.

Yet another provided method is a method of preventing progression of a laminopathy in a subject having or predisposed to the laminopathy, which method involves administering at least one FTI to the subject.

In examples of the various embodiments, the normally non-farnesylated lamin is a lamin other than Lamin B. For instance, in specific instances, the normally non-farnesylated lamin is lamin A.

It is specifically contemplated herein that the subject of any of the provided methods may be a subject having, or suspected of having, or susceptible to, atherosclerosis.

By way of specific, non-limiting examples, the FTI used in any method provided herein can be PD169541, R115777, SCH66336, or a farnesyltransferase inhibitory derivative thereof. Optionally, in any of the methods, a second therapeutic compound can be administered to the cell or subject. Examples of such second therapeutic compounds include another FTI, or a non-FTI compound.

A further embodiment is a method of screening for a compound useful in treating a laminopathy in a mammal. In an example of this embodiment, the method involves determining if a test compound alters a cellular defect selected from the group consisting of mis-localization of a farnesylated lamin, mis-localization of a non-farnesylated lamin, nuclear membrane disruption, aggregation of lamin, nuclear lobulation, nuclear blebbing, cytoskeleton disruption, early senescence, apoptosis, reduced secretion of MMP-3, or two or more thereof; and selecting a compound that alters the cellular defect so that it is more close to normal.

Also provided is a method for identifying an agent useful for treating a laminopathy, which method involves contacting the agent to a cell expressing progerin or a progerin-like abnormal lamin A protein under conditions sufficient to allow interaction between the cell and the agent; evaluating an amount of a cellular defect in the cell; and comparing the amount of the cellular defect in the cell contacted with the agent to an amount of the cellular defect in a control cell not treated with the agent, wherein a statistically significant (e.g., $p<0.05$, or $p<0.01$, or another selected level of significance) improvement in the amount of the cellular defect in the cell contacted with the agent, as compared to the control cell not treated with the agent, identifies the agent as one that is useful for treating the laminopathy.

Yet a further method provided herein is a method for identifying an agent that inhibits or reverses at least one cellular defect caused by constitutive farnesylation of a lamin protein. Such a method involves contacting a cell expressing progerin or a progerin-like abnormal lamin A protein with a test agent under conditions sufficient to allow interaction between the cell and the agent; and determining whether a cellular defect caused by constitutive farnesylation of a lamin protein is inhibited or reversed. By way of non-limiting example, the cellular defect is mis-localization of a farnesylated lamin, mis-localization of a non-farnesylated lamin, nuclear membrane disruption, aggregation of lamin, nuclear lobulation, nuclear blebbing, cytoskeleton disruption, early senescence, apoptosis, reduced secretion of MMP-3, or a combination of two or more thereof.

IV. Diseases Linked to Lamin A/C

Over 180 mutations have been reported in the LMNA gene, and currently there are eight diseases in addition to HGPS, referred to as the "laminopathies," that are associated with various mutations in this gene (Gruenbaum et al., *Nat. Rev. Mol. Cell Biol.* 6:21-31, 2005). These include such disorders as Emery-Dreifuss muscular dystrophy (EDMD; e.g., associated with heterozygous R527P), mandibuloacral dysplasia (associated with homozygous R527H), atypical Werner's syndrome, dilated cardiomyopathy-type 1A (CMD1A; e.g., associated with R644C), restrictive dermopathy, and Dunnigan-type familial partial lipodystrophy (Mounkes et al., *Curr. Opin. Genet. Dev.* 13:223-230, 2003; Navarro et al., *Hum. Mol. Genet.* 13:2493-2503, 2004).

Emery-Dreifuss muscular dystrophy is an autosomal recessive or dominant disease characterized by muscle weakness, contractures, and cardiomyopathy with conduction defects. Familial partial lipodystrophy (Dunnigan variety) (FPLD) is an autosomal dominant disorder characterized by marked loss of subcutaneous adipose tissue from the extremities and trunk but by excess fat deposition in the head and neck. This condition is frequently associated with profound insulin resistance, dyslipidemia, and diabetes.

Surprisingly, point mutations recently identified in the LMNA gene have been found to cause HGPS (PCT/US2003/033058, published as WO 04/035753, incorporated herein by reference in its entirety). The inheritance is new mutation autosomal dominant, and identified mutations occur in codon 608; the most common is due to a C to T base substitution in a CpG dinucleotide. It is currently believed that the mechanism of the mutations is activation of a cryptic splice site within the LMNA gene, which leads to deletion of part of exon 11 and generation of a lamin A protein product that is 50 amino acids shorter than the normal protein. All of the identified mutations are predicted to affect lamin A but not Lamin C. In addition, two cases of classical HGPS were identified with segmental UPD (uniparental disomy) of chromosome 1q from fibroblast DNA do not show the mutation, which may be indicative of a (in vivo or in vitro) somatic rescue event.

The results described herein can be generalized to the aging process and related conditions and diseases, beyond progeroid diseases. This is because HGPS is in many respects closely connected to normal aging processes. HGPS continues to be recognized as a useful model of aging (Fossel, *J. Pediatr Endocrinol Metab* 13 Suppl 6:1477-1481, 2000). For instance, the connection to atherosclerosis is very strong, especially of the coronary arteries. In addition, alopecia in HGPS is similar to that seen in subjects with advanced age. Further, the prime cellular feature of HGPS, as described many years ago by Hayflick and others (Hayflick, *N Engl J Med* 295:1302-1308, 1976) is early cellular senescence. The limited number of cell divisions in HGPS fibroblasts is similar to what is seen in fibroblasts derived from elderly individuals. That was further explored by research showing similarities in the gene expression patterns of HGPS fibroblasts and those derived from elderly persons, distinguishing them from fibroblasts derived from younger persons (Ly et al., *Science* 287: 2486-2492, 2000).

V. Specific HGPS Mutations Identified in LMNA

The typical LMNA mutation in HGPS is a nucleotide substitution of a C to a T at position 1824 of SEQ ID NO: 19 (corresponding to position 4277 in GI 292250 (Accession No. L12401)), causing no change in the encoded amino acid (G608G) (Accession No. P02545), but creating a cryptic splice donor site. Activation of this site results in an mRNA lacking 150 nucleotides. This is in turn translated into a mutant protein with a 50 amino acid internal deletion near the C-terminal end, termed progerin (Eriksson et al., *Nature* 423: 293-298, 2003). Lamin A is normally expressed by most differentiated cells, where it integrally affects both nuclear membrane structure and function (Rober et al., *Development* 105:365-378, 1989). Progerin apparently acts in a dominant negative manner on the nuclear function of cell types that express lamin A (Goldman et al., *Proc. Natl. Acad. Sci. USA* 101:8963-8968, 2004; Scaffidi & Misteli, *Nat. Med.* 11:440-445, 2005). In addition to the potential mechanical fragility created by disrupting the nuclear lamina, this mutation also may affect other vital cellular processes such as gene transcription, DNA replication, and cell division.

There has also been identified a change at nucleotide position 4275 in GI 292250, which corresponds to amino acid 608 (corresponding to position 1822 of SEQ ID NO: 19); this mutation changes a glycine to a serine in lamin A, and is predicted to generate the same cryptic splice site as the silent mutation. Hence both mutations generate the same mutant lamin A protein (progerin). The two mutations both occur in the same codon, which encodes amino acid 608.

The discovery that rare variants in the sequence of LMNA causes HGPS also enables a variety of diagnostic, prognostic, and therapeutic methods that are further embodiments. The new appreciation of the role of lamin A in HGPS and more generally aging illnesses and arteriosclerosis/atherosclerosis enables detection of predisposition to these conditions in a subject. This disclosure also enables early detection of subjects at high risk of these conditions, and provides opportunities for prevention and/or early treatment.

The deletion of the last half of exon 11 removes a cleavage site that is normally necessary for processing of lamin A. Post-translational modification of the CAAX box (SEQ ID NO: 31) at the C-terminus of lamin A, which is still present in the mutant forms, allows anchoring of the protein in the membrane—but then this anchoring mechanism is normally removed by the processing cleavage. The lamin A mutant protein (progerin) shown herein is not cleaved, and thus appears to be trapped in this membrane location. Since lamin A is part of a large multiprotein complex, its mislocalization is likely to pull other bystander proteins into the same improper location. It is now believed that this leads to structural abnormalities of the nucleus that can be visualized by light microscopy, immunohistochemistry, immunofluorescence, confocal microscopy, or electron microscopy. These characteristics are also useful for providing systems to test compounds for treating laminopathies.

VI. Farnesyltransferase Inhibitors to Ameliorate Progerin Cellular Disruption

Farnesylation is a permanent posttranslational modification; therefore, proteolytic cleavage is required to remove the farnesylated residue from lamin A protein and thereby effect defarnesylation and maturation of fully processed lamin A. Although it can be farnesylated, the progerin protein cannot be defarnesylated because it is missing the second cleavage site necessary for binding the protease ZMPSTE24, whose cleavage activity removes the last 15 amino acids in the C-terminal portion of the protein and effects defarnesylation (see, for instance, Eriksson et al., *Nature* 423(6937):293-298, 2003, incorporated herein by reference). Progerin maintains its nuclear localization sequence and its farnesyl group, along with the central rod that allows dimerization with normal lamin A and probably with itself. The result is an aberrant farnesylated protein putatively capable of altering normal lamin A function as a dominant negative, as well as assuming its own aberrant function through its association with the nuclear membrane. Thus, the multisystem disease process and the variety of genes that are affected in HGPS (Csoka et al., *Aging Cell* 3:235-243, 2004) lie downstream of a protein defect that is central to basic cellular function.

The progerin deletion has a number of consequences which give rise to the abnormal cellular phenotype, including abnormal protein processing and deletion of critical nuclear periphery protein binding domains. The retention of the farnesyl group changes important properties of the protein making it more lipophilic and altering interactions with other proteins. We have demonstrated in vivo that progerin is incompletely processed and retains the farnesyl group (Example 1). Expression of an N-terminal GFP-progerin fusion protein in normal fibroblasts caused abnormal nuclear morphology similar to that seen on HGPS fibroblasts. Furthermore, expression of the endogenous mutant in HGPS fibroblasts can cause abnormal localization of normal GFP tagged lamin A, demonstrating a dominant effect of the mutant protein on exogenously expressed normal lamin A. However, expression of the normal GFP-lamin A did not improve the nuclear morphology phenotype of HGPS fibroblasts, indicating that the deleterious effects of progerin are not compensated by increased expression of the normal protein.

It is also demonstrated herein that a protein cleavage site mutation construct gives rise to cellular phenotypes similar to a progerin construct (Example 2). A GFP-tagged cleavage-minus mutant lamin A (L647R) displayed a localization pattern very similar to the localization of GFP-tagged progerin when expressed in normal fibroblasts. Its expression caused a significant increase in abnormal nuclear morphology similar to the effect of the GFP-progerin construct.

Treatment of normal fibroblasts expressing progerin and HGPS fibroblasts with the farnesyltransferase inhibitor PD169541 resulted in a redistribution of GFP-lamin A and GFP-progerin localization and significant improvement in the nuclear morphology phenotype (Example 3). These studies indicate that abnormal farnesylation of progerin plays a major role in the abnormal cellular phenotype and suggest a possible therapeutic option for HGPS.

Based on the discoveries presented herein, it is shown that farnesyltransferase inhibitors (both direct effectors and indirect inhibitors) will inhibit or reduce the formation of progerin, cause a decrease in lamin A protein and an increase prelamin A protein. Decreasing the amount of aberrant protein may improve disease status in progeria and other laminopathies; this is supported by the discovery that treatment with an FTI reduces cellular defects linked to the expression of progerin. It is therefore believed that a farnesyltransferase inhibitor, such as (but not limited to) PD169541, R115777 (tipifarnib, Zarnestra), and SCH66336 (lonafarnib, Sarasar), will reduce or abolish the formation of progerin, decrease lamin A, and increase the levels of a prelamin A protein lacking 50 amino acids ("preprogerin"). This is demonstrated herein (Example 3), where normal fibroblasts expressing progerin and HGPS fibroblasts show a redistribution of GFP-lamin A and GFP-progerin localization and significant improvement in the nuclear morphology phenotype when exposed to the farnesyltransferase inhibitor PD169541.

Farnesyltransferase inhibitors can be used to reverse and/or prevent cellular effects caused by accumulation of progerin or other forms of constitutively farnesylated lamin protein. Thus, it is now determined that FTIs can be used to treat effects associated with expression of constitutively farnesylated lamin A, including for instance symptoms characteristic of HGPS, other laminopathies, aging-related conditions, atherosclerosis, and so forth. Specific cellular symptoms include mis-localization of farnesylated lamin, such a form of a lamin A protein (including prelamin A, progerin, preprogerin, and so forth), mis-localization of a non-farnesylated lamin, such as one or more non-farnesylated lamin A protein form (for instance, fully processed lamin A protein that is mislocalized due to association with a farnesylated lamin protein form), aggregation of lamin(s), nuclear membrane disruption, nuclear blebbing, nuclear lobulation, early senescence, apoptosis, and reduced secretion of MMP-3. In many instances, a cell will display a combination of two or more of these symptoms/effects.

VII. Farnesyltransferase Inhibitors

Farnesyltransferase inhibitors (FTIs) were developed originally as inhibitors of Ras biological activity, because FTase modification of Ras by farnesylation is essential for Ras to cause oncogenesis, and more generally as target-molecule specific chemotherapeutic agents. FTIs inhibit the post-translational addition of a 15-carbon farnesyl group to a C-terminal cysteine residue that is required, for instance, for farnesylated proteins (e.g., Ras) to localize to the cell membrane (Reuter et al., Blood 96(5):1655-1669, 2000). FTIs effectively block signaling and cellular transformation of some but not all isoforms of Ras, although it is certain that Ras is not the only target of farnesyltransferase inhibition (Ashar et al., J. Biol. Chem. 275(39):30451-30457, 2000; Liu et al., Mol. Cell Biol. 20(16):6105-6113, 2000). More generally, farnesyltransferase inhibitors were described as potentially useful to treat cancers where mutated forms of Ras are commonly found (e.g., colon and pancreatic cancers). However, since the most common forms of Ras found mutated in human cancers (K-Ras and N-Ras) undergo alternative prenylation by GGTase I when cells are treated with FTI (Whyte et al., J. Biol. Chem. 272:14459-14464, 1997), the anti-tumor activity of FTIs is not attributed to blocking Ras itself. Alternatively prenylated Ras, for instance geranylgeranylated K-Ras, retains function and is not inhibited by FTI. Instead, other substrates of FTase are believed to account for the clinical activity of FTIs. Farnesylated proteins that become alternatively prenylated in the presence of FTIs can escape the inhibitory effects of these compounds and remain functional. Therefore, it is critical to evaluate the possibility of alternative prenylation when determining whether a particular protein, for example progerin, can be targeted successfully by FTI treatment. Clinical consideration and prospects for FTIs in general are discussed in Cox and Der (Curr. Op. Pharma. 2:388-393, 2002).

FTIs generally can be divided into three groups: tetrapeptides having or mimicking the CAAX motif (SEQ ID NO: 31) (Brown et al., Proc. Natl. Acad. Sci. U.S.A. 89:8313-8316, 1992; Reiss et al., Proc. Natl. Acad. Sci. U.S.A. 88:732-736, 1991; Goldstein et al., J. Biol. Chem. 266:15575-15578, 1991); analogs of farnesyl pyrophosphate (FPP) (Gibbs et al., J. Biol. Chem 268:7617-7620, 1993); and inhibitors with structures not resembling either tetrapeptides or FPP (Liu et al., J. Antibiot. 45:454-457, 1992; Miura et al., FEBS Lett. 318:88-90, 1993; Omura et al., J. Antibiot. 46:222-228, 1993; Van Der Pyl et al. J. Antibiot. 45:1802-1805, 1992). The latter category of inhibitors generally has lower activity compared to the first two categories. By way of example, the FTI SCH66336 is a non-peptidomimetic FTI; FTI-277 is a peptidomimetic.

Several FTIs have entered into clinical trials in the last several years. For instance, the clinical candidate FTI SCH66336 (lonafarnib, Sarasar®) has been shown to inhibit proliferation of several human cancer cell lines and is active against human brain, lung, prostate, pancreas, colon, and bladder tumor xenografts in nude mice (Liu et al., Cancer Res. 58(21):4947-4956, 1998; Feldkamp et al., Cancer Res., 61(11):4425-4431, 2001). One Phase I clinical trial showed that SCH66336 inhibits protein farnesylation in vivo, and is generally well tolerated by the subject (Adjei et al., Cancer Res., 60(7):1871-1877, 2000). Anti-leukemic activity of SCH66336 on cell culture and mouse models of BCR/ABL has been demonstrated (Reichert et al., Blood, 97(5):1399-1403; 2001; Peters et al., Blood, 97(5):1404-1412, 2001).

The FTI R115777 (tipifarnib, Zarnestra®) has also entered clinical trials; it has been found to be well tolerated, but not fully effective against cancer (Adjei et al., J Clin Oncol. 21(9):1760-1766, 2003; Heymach et al., Annals of Oncology 15:1187-1193, 2004).

It is shown herein that FTIs can be used to reverse and/or prevent cellular effects caused by accumulation of progerin or other forms of constitutively farnesylated lamin A. It is believed that all categories of FTIs may be used in methods and compositions provided herein; the selection of a specific FTI is within the skill of the ordinary practitioner based on testing methods provided herein. In some embodiments, it is beneficial to select an inhibitor compound that is more selective for farnesyltransferase, compared to geranylgeranyl-transferase I. In other embodiments, it may be beneficial to select an inhibitor compound that is dually selective, in that it inhibits both FTase and GGTase I. Considerations for determining selectivity criteria for FTIs include (but are not limited to) the possibility of lower toxicity with FTase-specific FTIs versus dual specificity FTIs, although both efficacy and toxicity may differ according to the particular compound and the particular patient. As will be recognized by an ordinarily skilled practitioner, other considerations, for instance pharmacological and medical considerations, may also apply.

The development and chemistry of FTIs are well documented and known to those of ordinary skill. By way of example, the following publications review FTIs in the context of cancer treatment: Cox & Der, *Biochim Biophys Acta* 1333:F51-F71, 1997; Gelb et al., *Curr Opin Chem Biol* 2:40-48, 1998; Rowinsky et al., *J. Clin Oncol.* 17; 3631-3652, 1999; Oliff, *Biochim Biophys Acta* 1423:C19-C30, 1999; Sebti & Hamilton, *Expert Opin Investig Drugs* 9:2767-2782, 2000; and Gibbs et al., *Curr Med Chem* 8:1437-1465, 2001.

The following patent documents provide additional descriptions of making example farnesyltransferase inhibitors and compositions contain such compounds: WO 00/39082; WO 00/12499; WO 00/12498; WO 00/01691; WO 99/45912; WO 98/49157; WO 98/40383; WO 98/28303; WO 97/30992; WO 97/21701; WO 97/16443; WO 94/10138; U.S. Application Publication 20040063770; U.S. Application Publication 20030060450; U.S. Pat. Nos. 6,187,786; 6,177,432; 6,169,096; 6,133,303; 6,037,350; 5,976,851; 5,972,984; 5,972,966; 5,968,965; 5,968,952; 5,965,578; 5,965,539; 5,958,939; 5,939,557; 5,936,097; 5,891,889; 5,889,053; 5,880,140; 5,872,135; 5,869,682; 5,861,529; 5,859,015; 5,856,439; 5,856,326; 5,852,010; 5,843,941; 5,807,852; 5,780,492; 5,773,455; 5,767,274; 5,756,528; 5,750,567; 5,721,236; 5,700,806; 5,661,161; 5,602,098; 5,585,359; 5,578,629; 5,534,537; 5,532,359; 5,523,430; 5,504,212; 5,491,164; 5,420,245; and 5,238,922.

Also useful are pharmaceutically acceptable acid or base addition salts of FTIs, including any of the inhibitors as mentioned above. The phrase "pharmaceutically acceptable acid or base addition salts" includes therapeutically active non-toxic acid and non-toxic base addition salt forms which FTIs are able to form. Such compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

FTI compounds which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms that an FTI is able to form. Examples of such forms are, for instance, hydrates, alcoholates and the like.

Also contemplated for use in methods and compositions described herein are stereochemically isomeric forms of FTIs. The term stereochemically isomeric form includes all possible compounds made up of the same atoms bonded by the same sequence of bonds, but having different three-dimensional structures that are not interchangeable. Unless otherwise mentioned or indicated, the chemical designation of a compound encompasses the mixture of all possible stereochemically isomeric forms that the compound may possess. Such mixture may contain all diastereomers and/or enantiomers of the basic molecular structure of the compound. Also contemplated are all stereochemically isomeric forms in pure form or in admixture with each other. Also contemplated are tautomeric forms of FTI compounds.

VIII. Methods of Treatment

The present disclosure includes methods of using various compounds and compositions, including any of the listed FTIs or other compounds identified as capable of inhibiting, directly or indirectly, farnesylation of lamin A or progerin (referred to generally as FTI compounds), as a treatment for disease. In a particular embodiment, the FTI compound is a peptidomimetic or non-peptidomimetic inhibitor of the farnesyltransferase enzyme, and the treatment is a treatment of a laminopathy, such as HGPS or another progeroid disease or condition, an age-related condition, a cardiovascular disease or condition (such as atherosclerosis), and so forth.

The method includes administering a pharmaceutical agent or FTI, or more than one, or a combination of a FTI (or more than one) and one or more other pharmaceutical agents, to the subject in a pharmaceutically compatible carrier and in an amount effective to inhibit the development or progression of a disease. Although the treatment can be used prophylactically in any patient in a demographic group at significant risk for such diseases, subjects can also be selected using more specific criteria, such as a definitive diagnosis of the disease/condition or identification of one or more factors that increase the likelihood of developing such disease (e.g., a genetic factor).

Various delivery systems are known and can be used to administer chemical compounds and FTIs as therapeutics. Such systems include, for example, encapsulation in liposomes, microparticles, microcapsules, recombinant cells capable of expressing therapeutic molecule(s) (see, e.g., Wu et al., *J. Biol. Chem.* 262, 4429, 1987), construction of a therapeutic nucleic acid as part of a retroviral or other vector, and the like. Methods of introduction include, but are not limited to, intrathecal, intradermal, intramuscular, intraperitoneal (ip), intravenous (iv), subcutaneous, intranasal, epidural, and oral routes. The therapeutics may be administered by any convenient route, including, for example, infusion or bolus injection, topical, absorption through epithelial or mucocutaneous linings (e.g., oral mucosa, rectal and intestinal mucosa, and the like) ophthalmic, nasal, and transdermal, and may be administered together with other biologically active agents. Pulmonary administration can also be employed (e.g., by an inhaler or nebulizer), for instance using a formulation containing an aerosolizing agent.

In a specific embodiment, it may be desirable to administer the pharmaceutical compositions of the invention locally to the area in need of treatment. This may be achieved, for example, and not by way of limitation, by local infusion or perfusion (e.g., during surgery), topical application (e.g., in a dressing), injection, catheter, suppository, or implant (e.g., implants formed from porous, non-porous, or gelatinous materials, including membranes, such as sialastic membranes or fibers), and the like. In one embodiment, administration can be by direct injection at the site (or former site) of a tissue that is to be treated. In another embodiment, the therapeutic are delivered in a vesicle, in particular liposomes (see, e.g., Langer, *Science* 249, 1527, 1990; Treat et al., in *Liposomes in the Therapy of Infectious Disease and Cancer*, Lopez-Berestein and Fidler (eds.), Liss, N.Y., pp. 353-365, 1989).

In yet another embodiment, the therapeutic can be delivered in a controlled release system. In one embodiment, a pump may be used (see, e.g., Langer *Science* 249, 1527, 1990;

Sefton *Crit. Rev. Biomed. Eng.* 14, 201, 1987; Buchwald et al., *Surgery* 88, 507, 1980; Saudek et al., *N. Engl. J. Med.* 321, 574, 1989). In another embodiment, polymeric materials can be used (see, e.g., Ranger et al., *Macromol. Sci. Rev. Macromol. Chem.* 23, 61, 1983; Levy et al., *Science* 228, 190, 1985; During et al., *Ann. Neurol.* 25, 351, 1989; Howard et al., *J. Neurosurg.* 71, 105, 1989). Other controlled release systems, such as those discussed in the review by Langer (*Science* 249, 1527 1990), can also be used.

The vehicle in which the agent is delivered can include pharmaceutically acceptable compositions of the compounds, using methods well known to those with skill in the art. For instance, in some embodiments, chemical compounds, small molecules, and/or specifically FTIs typically are contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. These therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: *The Science and Practice of Pharmacy* (19th Edition, 1995) in chapter 95.

Embodiments of other pharmaceutical compositions are prepared with conventional pharmaceutically acceptable counter-ions, as would be known to those of skill in the art.

Therapeutic preparations will contain a therapeutically effective amount of at least one active ingredient, preferably in purified form, together with a suitable amount of carrier so as to provide proper administration to the patient. The formulation should suit the mode of administration.

The composition of this disclosure can be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

The ingredients in various embodiments are supplied either separately or mixed together in unit dosage form, for example, in solid, semi-solid and liquid dosage forms such as tablets, pills, powders, liquid solutions, or suspensions, or as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to administration.

The amount of the therapeutic that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each patient's circumstances. An example of such a dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The therapeutic compounds and compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated.

In some embodiments, sustained localized release of the pharmaceutical preparation that comprises a therapeutically effective amount of a therapeutic compound or composition may be beneficial. Slow-release formulations are known to those of ordinary skill in the art. By way of example, polymers such as bis(p-carboxyphenoxy)propane-sebacic-acid or lecithin suspensions may be used to provide sustained localized release.

It is specifically contemplated in some embodiments that delivery is via an injected and/or implanted drug depot, for instance comprising multi-vesicular liposomes such as in DEPOFOAM® drug delivery agent (SkyePharma, Inc, San Diego, Calif.) (see, for instance, Chamberlain et al., *Arch. Neuro.* 50:261-264, 1993; Katri et al., *J. Pharm. Sci.* 87:1341-1346, 1998; Ye et al., *J. Control Release* 64:155-166, 2000; and Howell, *Cancer J.* 7:219-227, 2001).

IX. Cell-Based Systems for Identifying and Characterizing FTIs for Treatment

Also provided herein are in vivo assay systems designed to show the ability of test compounds (test agents) to inhibit farnesyltransferase and more specifically, ability of test compounds to reduce or ameliorate one or more cellular effects caused by constitutive farnesylation of lamin A.

If farnesylation is inhibited, maturation of lamin A cannot be completed and the precursor (prelamin A) accumulates. This phenomenon has been recognized (see, e.g., Beck et al., *J. Cell Biol.* 110:1489-1499, 1990; Kilic et al., *J. Biol. Chem.* 272:5298-5304, 1997). Thus, inhibition of farnesylation can be detected by detecting increased accumulation of prelamin A (e.g., on a gel based on differential mobility, or using an antibody that preferentially detects prelamin A). One method for generating a prelamin A-specific antibody preparation is described in Adjei et al. (*Clin Cancer Res* 6:2318-2325, 2000). Detection of prelamin A is recommended as a marker of farnesyltransferase inhibition in that same reference. It was shown to be detectable using Western blotting and immunohistochemical staining, as well as differential migration on SDS-PAGE.

Similarly, inhibition of farnesyltransferase can be measured by detecting changes in processing, and therefore changes in electrophoretic mobility, of other proteins. By way of example, the chaperone HDJ-2 [Neckers et al., *The Hsp90 chaperone family, In*: D. S. Latchmann (ed.), *Stress Proteins*, pp. 9-42 (New York: sprinter-Verlag, 1999)] and the peroxisomal protein Pxf (James et al., *J. Biol. Chem* 269:14182-14190, 1994) are good candidate markers for monitoring farnesyltransferase inhibition (Adjei et al., *Clin Cancer Res* 6:2318-2325, 2000).

In addition, specific examples provided herein describe constructs useful in cell-based systems. These systems can be used, for instance, in studying the effectiveness of specific FTIs (or other candidate therapeutic compounds) to ameliorate symptoms (particularly, cellular defects) of constitutive farnesylation of lamin protein forms. Specific systems therefore exploit methods of detecting and analyzing mis-localization of a farnesylated lamin, mis-localization of a non-farnesylated lamin, nuclear membrane disruption, aggregation of lamin protein, nuclear lobulations, nuclear blebbing, cytoskeleton disruption, early senescence, apoptosis (e.g., through measurement of Annexin V), reduced secretion of MMP-3, and so forth. It is contemplated that certain of such cell-based systems could be used in a high-throughput format, in order to more rapidly analyze the effect and effectiveness of known and putative inhibitory molecules.

Examples of described constructs, cell-based systems, and transgenic animals are specifically contemplated for use in characterizing, testing, selecting, and identifying compounds that may be putative farnesyltransferase inhibitory.

The following examples are provided to illustrate certain particular features and/or embodiments. These examples should not be construed to limit the invention to the particular features or embodiments described.

EXAMPLES

Example 1

Incomplete Lamin a Processing in HGPS Leads to Nuclear Abnormalities

This example describes methods for detecting lamin A in cells, and examining cellular characteristics that result from expressing progerin.

GFP-tagged normal and mutant LMNA expression constructs have been created, and normal and HGPS fibroblasts have been transfected with these constructs in order to examine protein localization and effect on nuclear structure. Expression of the mutant lamin A protein (progerin) in normal fibroblasts caused abnormal nuclear morphology including mislocalization of progerin to foci at the nuclear periphery and nuclear blebbing similar to that seen in HGPS fibroblasts. Expression of normal lamin A in HGPS fibroblasts did not significantly correct the nuclear blebbing phenotype. Furthermore, the normal GFP-lamin A was mislocalized, indicating that the presence of the endogenous mutant can act in a dominant-negative fashion. The progerin deletion could have a number of consequences which could give rise to this abnormal cellular phenotype, including abnormal protein processing and deletion of critical protein binding domains. The deleted region includes a protein cleavage site that normally removes 15 amino acids including a CAAX box (SEQ ID NO: 31) farnesylation site.

Methods

Constructs: Normal and mutant alleles of lamin A/C were cloned by isolating RNA from the cell lines AG11513a and NF, respectively. An oligo dT primer was used for first strand synthesis using the SUPERSCRIPT® reverse transcriptase kit (Invitrogen). The first strand cDNA was used as a template to amplify normal and mutant products using the Platinum Taq high fidelity kit from Invitrogen with the primers laminAF1 (SEQ ID NO: 1) and laminAR1 (SEQ ID NO: 2). Due to the GC-rich nature of the template, DMSO and betaine were added to final concentrations of 4% and 500 mM, respectively. The reaction was run for 20 cycles with an annealing temperature of 62° C. and the resulting product was used for TOPO TA cloning (Invitrogen). These cDNA constructs were verified by sequencing and used as templates for subcloning into the pEGFP-C2 and pRevTRE vectors (Clontech).

Cell Culture: Cell lines used were normal fibroblast lines, GM08398 and HGMDFN090, and HGPS fibroblast lines: P01 (HGADFN003), HGADFN004, HGADFN136, AG03513d, AG10750 and AG11498. Fibroblasts were cultured in minimal essential medium (Gibco, #10370-021) supplemented with 15% FBS (HiClone), 2 mM L-glutamine, penicillin (50 U/ml) and streptomycin (50 mg/ml). The Amphotropic Phoenix retroviral packaging line (Peter Nolan, Stanford University) was maintained in DMEM supplemented with 10% FBS, 2 mM L-glutamine, penicillin (50 U/ml) and streptomycin (50 mg/ml).

Retroviral Constructs: The pRevTetOff vector and pRevTRE constructs were transfected using FUGENE®6 transfection reagent into the Amphotropic Phoenix retroviral packaging line (Peter Nolan, Stanford University). Forty-eight hours after transfection the media containing retrovirus was filtered through a 0.22 micron filter and used immediately or stored at −70° C. Retroviral infection was performed by exposing target cells to a 1:1 mix of retroviral supernatant and growth medium with 4 μg/ml polybrene.

GFP localization: Normal and HGPS fibroblasts were plated on coverslips in six well plates or in chambered microscope slides (BD Biosciences) 24 hours prior to transfection. Fibroblasts were transiently transfected with the GFP-lamin A or GFP-progerin expression constructs using FUGENE®6 transfection reagent (Roche). Seventy-two hours later the cells were washed two times with PBS (pH 7.2) and fixed for 20 minutes at 4° C. with 4% paraformaldehyde in PBS containing 62.5 μg/ml LPC palmitoyl and 1 U/ml rhodamine phalloidin (Molecular Probes) to stain the cytoskeleton. Following three washes with PBS, Prolong Gold mounting medium with DAPI (Molecular Probes) was applied to the coverslips which were then inverted and placed on microscope slides.

Immunocytochemistry: Immunocytochemistry (ICC) was performed as previously described. Cells were cultured on coverslips in 6-well plates for 72 hours. Coverslips were washed twice with PBS and fixed with 4% paraformaldehyde in PBS with 0.18% Triton X-100 for 20 min at 4° C. Coverslips were washed 3 times with PBS and incubated 30 min at 37° C. in blocking buffer (1% BSA in PBS). The cells were probed with 1:10 dilution of the lamin A specific antibody (USBiological) in blocking buffer for 1 hour at room temperature followed by washing three times with PBS. Secondary antibody (Goat Anti-Mouse IgG, FITC) was diluted 1:1000 in blocking buffer and applied to the coverslips for 1 hour at room temperature. After washing three times for 5 minutes with PBS, the coverslips were inverted and placed on slides with ProLong Gold mounting medium containing DAPI (Molecular Probes).

Immunoprecipitation: Cells from nearly confluent T75 flasks were harvested and lysed in RIPA buffer containing a protease inhibitor cocktail (Roche). Cell pellets were vortexed and sonicated briefly to ensure thorough lysing. 500 mg of total cellular protein in a final volume of 500 µl from each sample was immunoprecipitated as follows. Cell lysate was precleared by incubating for 1 hour with protein G sepharose at 4° C. on a nutator mixer. The protein G sepharose was removed by a brief spin and the supernatant was incubated with 100 µl anti-lamin A/C antibody (Abcam ab8984) overnight at 4° C. Fifty µl protein G Sepharose was added to each sample and incubated for 3 hour at 4° C. After washing four times with RIPA buffer, 50 µl 2× NuPAGE sample buffer with reducing agent (Invitrogen) was added to the protein G pellet, heated to 100° C. for 10 min, and loaded onto a 4-12% Bis-Tris NuPAGE gel (Invitrogen).

Immunoblotting: Proteins were transferred to Immobilon-P membrane (Millipore) using a Trans-Blot semi-dry electrophoretic transfer cell (BioRad) blocked with 5% dry milk in TBST and probed with lamin A/C specific antibodies according to standard protocols.

Results

GFP Localization

Figure 1:
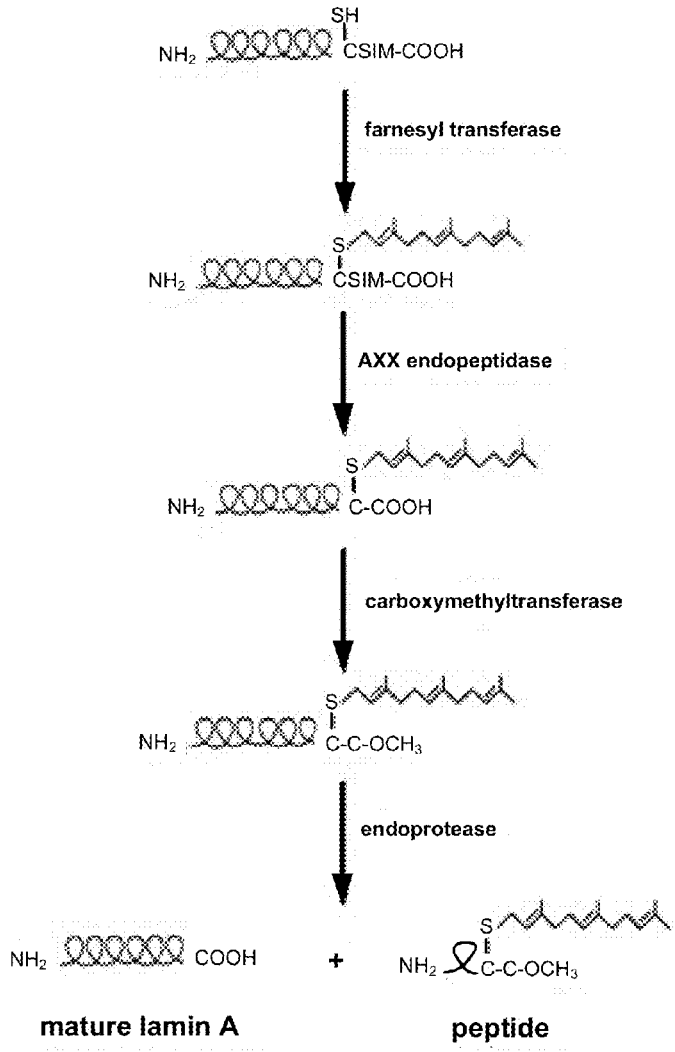
FIG. 1 shows a schematic overview of normal lamin A processing. The C-terminal CAAX box (SEQ ID NO: 31) of prelamin A undergoes farnesylation, which allows localization of the partially processed protein to the nuclear membrane. The AAX endopeptidase cleaves the last three amino acids from the farnesylated protein. Prelamin A then undergoes methyl esterification at the C-terminus. The endoprotease ZMPSTE24 then cleaves the c-terminal 15 amino acids, which cleavage releases a short peptide containing both the farnesylation and the methyl ester. This last proteolytic cleavage is prevented in progerin, as the cleavage site is lost in the 50 amino acid deletion. In addition, neither proteolytic cleavage can occur without prior farnesylation of the precursor protein.
Figure 2:
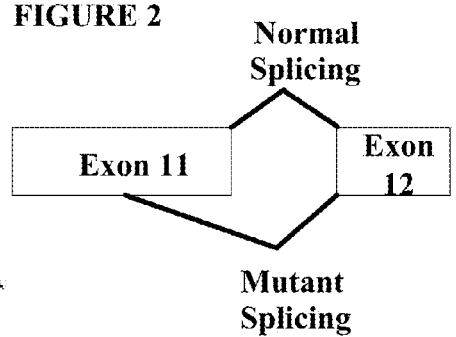
FIG. 2 is a diagram showing the differential processing of lamin A exon 11 in wild-type and the HGPS mutant. The silent mutation G608G leads to activation of a cryptic splice site, which results in splicing-out of 150 nucleotides corresponding to the 3'-end of Exon 11.
Figure 3:
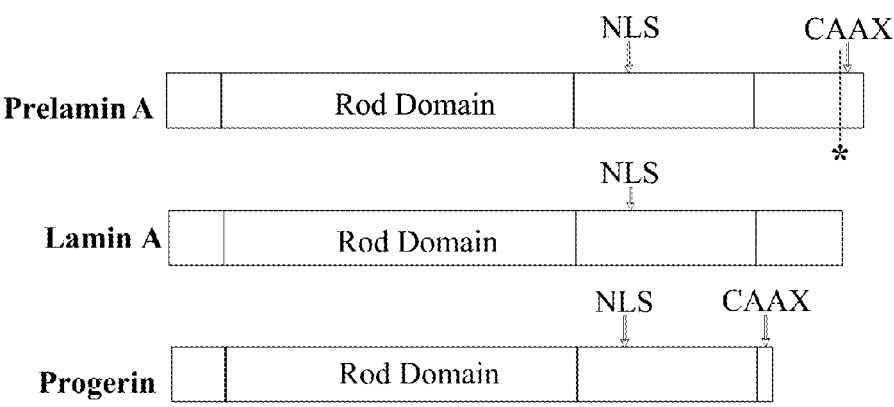
FIG. 3 shows drawings of prelamin A, lamin A, and progerin. The deletion in progerin removes amino acids 608-657 of the wildtype lamin A protein; this region includes both a phosphorylation site (indicated in the figure by an asterisk) and a proteolytic cleavage site that is required for maturation from the pre-form to the mature lamin A. The nuclear localization sequence (NLS) is unaffected by the mutation.
Figure 4:
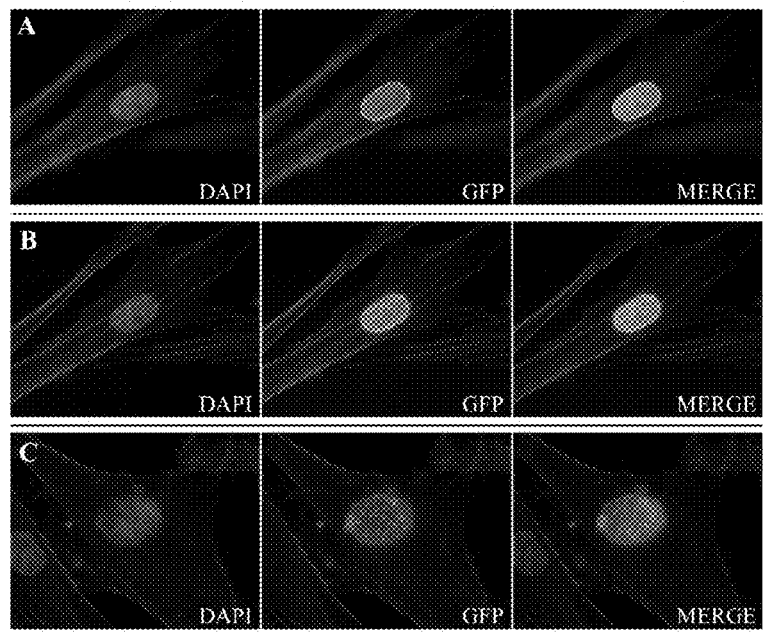
FIG. 4 (panels A-C) illustrates nuclear morphology and protein localization in cells transfected with plasmid DNA encoding green fluorescent protein (GFP)-tagged lamin A or GFP-tagged wild type or mutant progerin proteins. GFP-lamin A (panels A and B) or GFP-progerin (panel C) expression constructs were transiently transfected into the normal fibroblast line, GM08398, using FUGENE® transfection reagent (Roche). Seventy-two hours later the cells were fixed with 4% paraformaldehyde and visualized using a Zeiss AXIOPHOT™ fluorescence microscope with a SENSYS® CCD camera and Applied Imaging digital imaging capture software. The actin cytoskeleton was stained with Rhodamine-phalloidin. Panel A shows the same cell as in Panel B but with the focal plane bisecting the nucleus. In B and C the periphery of the nucleus is in focus to show the altered localization of GFP-progerin in panel C.
Figure 5:
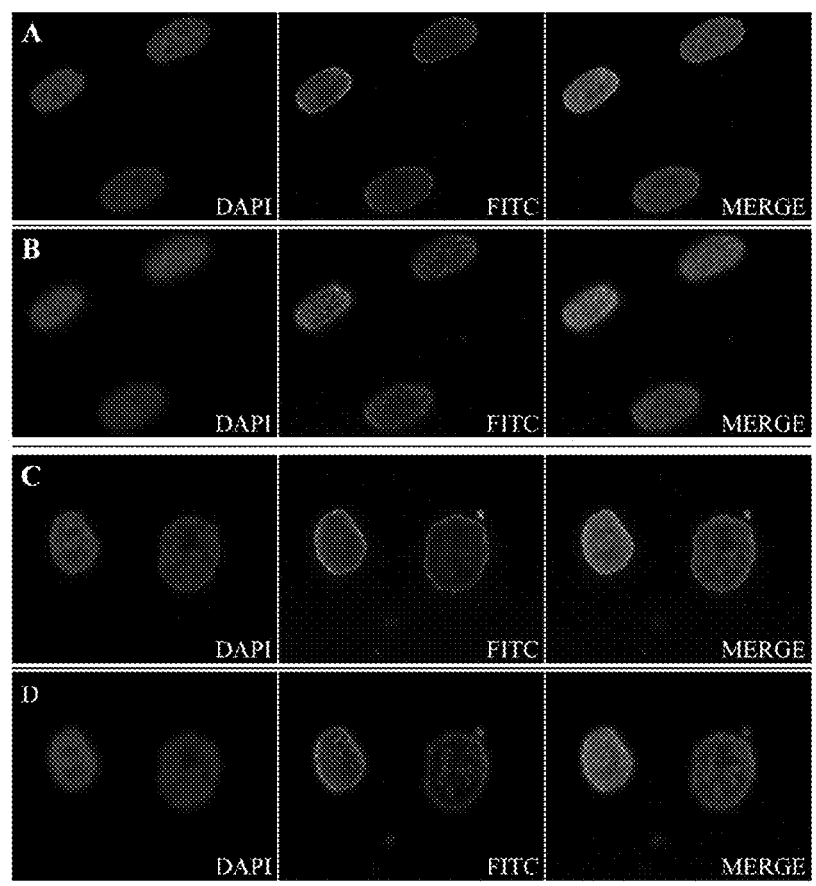
FIG. 5 (panels A-D) illustrates immunocytochemistry using a lamin A-specific antibody to detect localization of endogenous lamin A. Normal (A and B) and HGPS(C and D) fibroblasts were grown on coverslips, fixed with formaldehyde and probed with anti-lamin A antibodies (USBiological). Lamin A aggregates were observed in HGPS fibroblasts. Images show two focal planes, a nuclear cross-section (A and C) and a focal plane bisecting the nucleus (B and D).

When GFP-tagged normal lamin A was expressed in normal fibroblasts, the nuclei had an oval shape with fluorescence evenly distributed at the periphery of the nucleus (FIGS. 4A and 4B). Expression of the GFP-tagged progerin in normal fibroblasts caused abnormal nuclear morphology, similar to that seen in HGPS fibroblasts including nuclear blebbing, and the mislocalization of the GFP-tagged progerin into nuclear foci in many cells (FIG. 4C). Expression of normal lamin A in HGPS fibroblasts for 72 hours did not significantly correct the nuclear blebbing phenotype seen in these cells, and the normal GFP-lamin A was mislocalized, indicating that the presence of the endogenous mutant can cause mislocalization of the normal GFP-tagged lamin A. These experiments were repeated using confocal microscopy in order to verify these results and gain very high resolution images that better show the localization of GFP-progerin (FIG. 6). The most commonly seen localization pattern for the GFP-progerin 72 hours post-transfection appears as thick regions in the nuclear lamina. These were also detected by ICC in HGPS fibroblasts with less resolution most likely due to a lack of availability of the epitope within these aggregates (FIG. 5).

GFP-lamin A and GFP-progerin were also expressed from TET-OFF® retroviral expression vector constructs that allow for sustained expression and modulation of expression to address the possibility of results due to over-expression of the fusion proteins. Reducing expression of GFP-progerin (as measured by Western blotting) did not significantly alter the localization of the mutant protein into aggregates at the nuclear periphery.

Progerin Processing

Figure 7C:
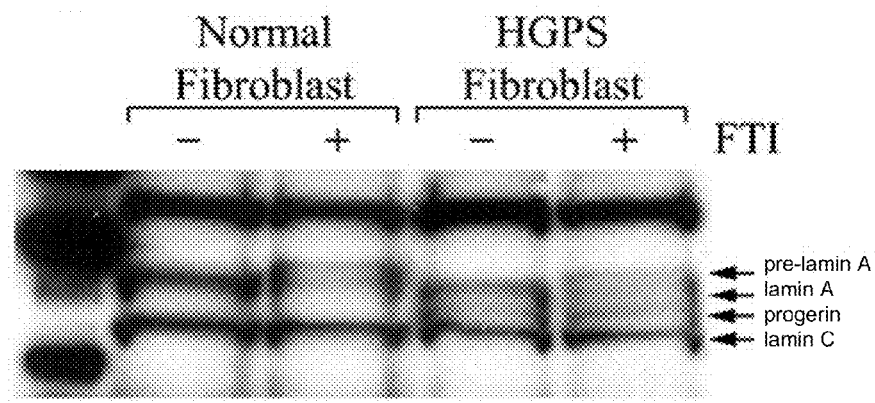
FIG. 7 (panels A-E) illustrates the effect of a 72 hour exposure to 100 nM FTI (PD169451) on GFP-lamin A (A) and GFP-progerin (B) localization, protein processing (C) and nuclear morphology (D and E). Confocal microscopy was used to examine the effects of FTIs on transiently-expressed GFP-lamin A (A) and GFP-progerin (B) in normal fibroblasts. Three focal planes are shown—top, middle and bottom (from left to right). Exposure to 100 nM FTI for 72 hours caused about half of the endogenous lamin A to be unprocessed pre-lamin A in normal and HGPS fibroblasts (C). Exposure to the FTI increased the percent of mock transfected cells and GFP-lamin A expressing cells with abnormal nuclear morphology (D). However, the percentage of cells expressing GFP-progerin with an abnormal nuclear morphology decreased by 33% when exposed to the FTI for 72 hours. The nuclear morphology of HGPS fibroblasts showed a similar improvement in the percent of abnormal nuclei when exposed to the FTI for 72 hours (E).

In order to determine if the progerin protein retains a farnesyl group an immunoprecipitation (IP) was performed using anti lamin A/C antibodies (Abcam ab8984). The IP step was necessary because as many as 0.1% of cell proteins are modified by the addition of farnesyl or geranylgeranyl group. Progerin was efficiently detected following IP as a protein of approximately 74 kDa that runs between lamin C (70 kDa) and lamin A (78.5 kDa) on an immunoblot, consistent with the loss of 50 amino acids from lamin A (FIG. 7C). The presence of a $^3$H-labeled farnesyl group on the progerin protein was detected by fluorography of the immunoprecipitated proteins. A farnesyl group was not detected on normal lamin A so the normal protein was completely processed in these cells. The addition of 2 µM FTI prevented the farnesylation of progerin and lamin A. In addition, the pre-lamin A band in these lanes was shown by the presence of a larger band since farnesylation was necessary for the subsequent processing steps including removal of the C-terminal 18 amino acids.

Discussion

To date, there have been seven diseases associated with mutations in the LMNA gene. The disorders include muscular dystrophy, lipodystrophy and neuropathy, and the tissues most affected in these disorders are striated muscle, adipose tissue and bone (reviewed in Burke & Stewart, Nat Rev Mol Cell Biol 3:575-585, 2002). The remarkable heterogeneity and phenotypic differences of the laminopathies are reflected in the distribution of mutations in LMNA. Virtually all HGPS patients have the same mutation creating an abnormal splice donor site in exon 11 of the LMNA gene. The mis-splicing creates a protein missing 50 amino acids in a globular domain near the C-terminus. Mutations causing Dreifuss muscular dystrophy (EDMD2) are distributed throughout the gene, while those resulting in familial dilated cardiomyopathy type 1 (CMD1A) are mainly clustered within the coiled-coil domain, suggesting that the latter may act by disrupting dimerization or subsequent polymerization of lamin A/C. In contrast, the mutations found in individuals with HGPS, Dunnigan familial partial lipodystrophy (FPLD), and mandibuloacral dysplasia (MADA or MAD) are found within exons encoding the C-terminal globular domain of lamin A/C and, more specifically, are restricted to just a few codons in exons 8, 9 and 11 (Eriksson et al., Nature 423:293-298, 2003; Shackleton et al., Nat Genet 24:153-156, 2000; Speckman et al., Am J Hum Genet 66:1192-1198, 2000; Novelli et al., Am J Hum Genet 71:426-431, 2002). Abnormal nuclear morphology is seen in many of the laminopathies, including Emory (EDMD2) and FPLD, so it seems unlikely that this cellular phenotype alone accounts for the HGPS-specific disease phenotypes.

We and others have described the mis-splicing caused by the activation of a cryptic splice site due to the codon 608 mutation in HGPS. The mis-splicing results in loss of 150 nucleotides between the cryptic splice site and the end of exon 11. The frame of the transcript is retained so that the final nine codons from exon 12 are transcribed including a CAAX box (SEQ ID NO: 31) farnesylation site. However, the deletion of 50 amino acids may have numerous consequences, including deletion of protein binding domains and deletion of the cleavage site necessary for normal protein processing and predicted removal of the farnesyl group from the mature protein. Incomplete processing of lamin A appears to be an important factor as mutations in ZMPSTE24 (the protease that performs the final cleavage step removing the farnesyl group) are found in patients with a severe form of mandibuloacral dysplasia. Although the conserved cleavage site is missing in progerin, it remained possible that the protein was still cleaved as there are potential sites in the progerin protein that may have substituted for the missing cleavage sequence. Thus, while maintenance of the farnesyl group is predicted, it had not been formally proven.

Data presented in this example show that the progerin protein remains farnesylated and is not cleaved. The retention of the farnesyl group may have numerous consequences. Farnesyl groups increase lipophilicity and are involved in membrane association. Also, farnesyl groups are involved in protein interactions. In fact, the protein Narf has been shown to interact only with the farnesylated form of lamin A (Barton & Worman, *J Biol Chem.* 274:30008-30018, 1999). Retention of the farnesyl group on the progerin protein and on the cleavage minus mutant alters the localization of these proteins in comparison to the normal lamin A. This abnormal distribution of the nuclear lamin A may contribute to the loss of integrity of the lamina and thus result in the abnormal nuclear phenotype observed in HGPS cells and when these proteins are expressed in normal cells.

N-terminal GFP-lamin A fusions have been shown previously to display localization patterns consistent with localization of the non-tagged protein. The fusion protein has the added advantage of showing lamin structures that are difficult to detect using ICC because epitopes are not available.

Example 2

Cleavage Mutant of Lamin A

As shown in Example 1, the C-terminus of progerin was not cleaved and the protein remained farnesylated. This example provides the construction of a cleavage-site mutation in lamin A, and compares its processing and cellular effects with those of progerin. Transfection of normal cells with the codon 647 cleavage site mutation construct was found to give rise to similar nuclear abnormalities as those seen in progeria cells. These results indicate that abnormal farnesylation of progerin plays a major role in the abnormal cellular phenotype.

Methods

Creation of Cleavage Minus Mutant

The L647R mutant was introduced into the pRevTRE-GFP-lamin A construct using a PCR-based site directed mutagenesis. Two overlapping PCR products were generated using the following primer pairs: PCR product 1 using the primers LMNA-1320-For (SEQ ID NO: 3) and LMNA-L647R-Rev (SEQ ID NO: 4), and PCR product 2 using the primers LMNA-L647R-For (SEQ ID NO: 5) and pRevTRE-3700-Rev (SEQ ID NO: 6). The reverse primer for product 1 is the complement sequence to the forward primer for product 2 and both of these primers contain a single mismatch with the target sequence that will generate the L647R mutation.

Both products were gel purified and used together as the template for a third PCR reaction using the primers LMNA-1390-For (SEQ ID NO: 7) and pRevTRE-3440-Rev (SEQ ID NO: 8). Although the template is two overlapping fragments, a single PCR product results, which was gel purified and cloned using the TOPO® TA cloning kit (Invitrogen). The resulting insert was subcloned into the pRevTRE-GFP-lamin A construct using Mfe I and Cla I restriction endonucleases. The resulting construct, pRevTRE-GFP-LA(L647R) was sequenced to verify the presence of the introduced mutation without any random base changes due to the use of PCR to generate the construct.

Results and Discussion

A mutant lamin A was engineered to create a L647R amino acid change in the cleavage site of lamin A, so that the effect of retaining the farnesyl group could be assessed without the 50 amino acid deletion that occurs in the progerin protein. The L647R mutation changed a conserved base in the cleavage site of lamin A so that ZMPSTE24 could not cleave the protein, leaving it farnesylated.

Figure 8:
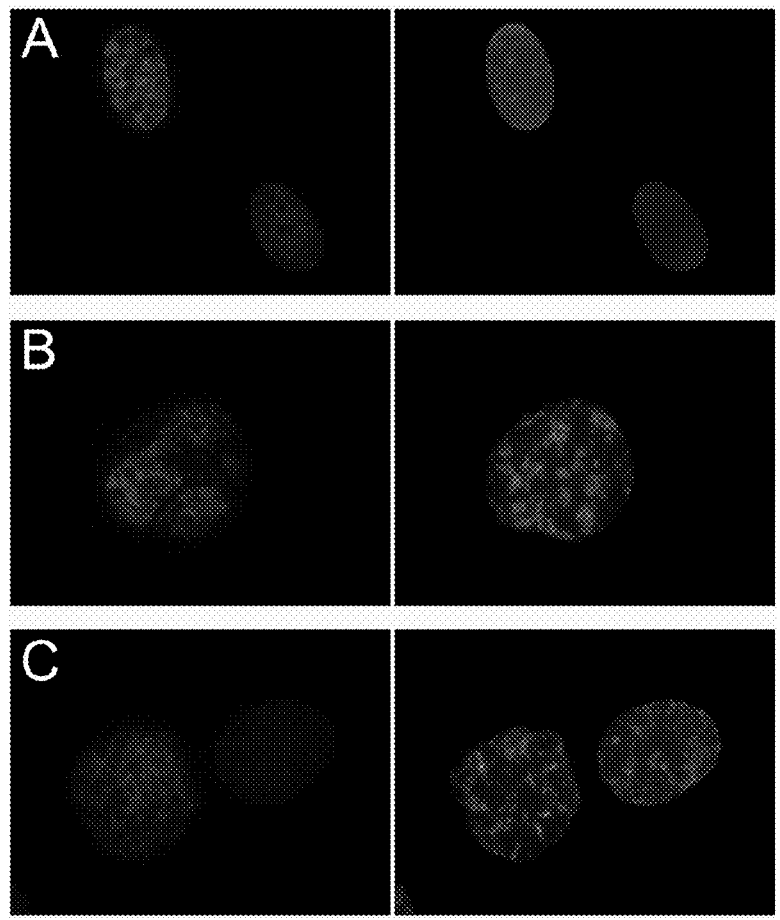
FIG. 8 (panels A-C) shows the nuclear morphology of normal fibroblasts (GM08398) expressing GFP-lamin A (panel A), GFP-progerin (panel B), and GFP-lamin A L647R (panel C). DAPI staining of nuclei is shown on the left and GFP signal on the right. The GFP constructs were expressed from the pRevTRE retroviral TET-OFF® expression vector for three days by removing tetracycline from the growth medium followed by fixing the cells with 4% paraformaldehyde and mounting with PROLONG® Gold antifade mounting reagent with DAPI.
Figure 9:
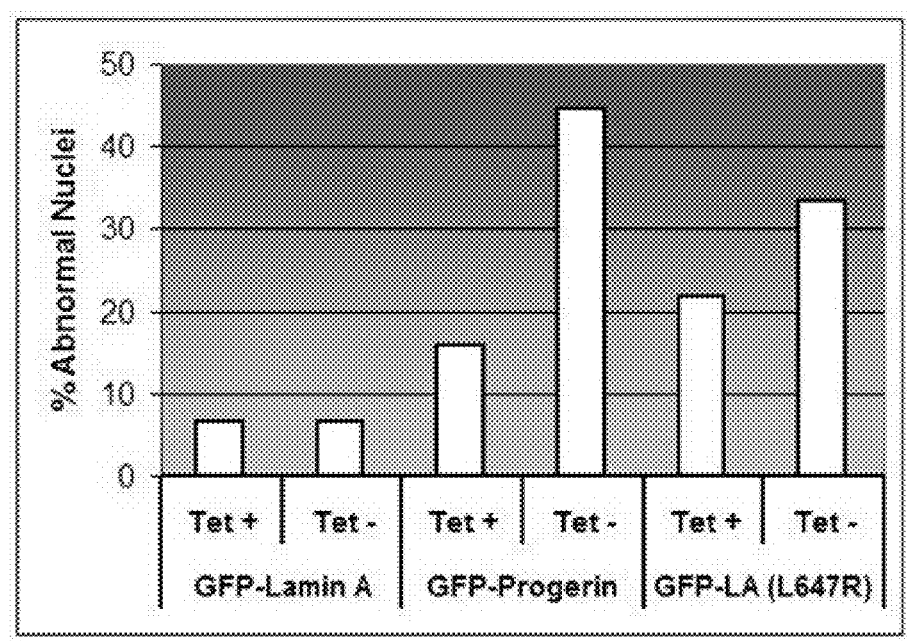
FIG. 9 illustrates the effect of expressing the cleavage minus mutant (GFP-lamin A L647R) on nuclear morphology. GFP-lamin A, GFP-progerin, and GFP-lamin A L647R were expressed in the normal fibroblast line, GM08398, for three days followed by fixing the cells with 4% paraformaldehyde and mounting with ProLong Gold with DAPI. Abnormal nuclear morphology was assessed as nuclei with multiple blebs. The elevated proportion of abnormal nuclei in the presence of tetracycline (+Tet) in the GFP-progerin and GFP-LA L647R is due to the leaky expression of these proteins in the concentration of tetracycline used to prevent expression.

A GFP-tagged cleavage-minus mutant lamin A (L647R) displayed a localization pattern nearly identical to the localization of GFP-tagged progerin when expressed in normal fibroblasts (FIG. 8). Its expression caused a significant increase in abnormal nuclear morphology, similar to the effect of the GFP-progerin construct (Example 1) (FIG. 9). This result demonstrates that incomplete processing of lamin A such that it retains the farnesyl group can cause morphological changes in cells similar to those caused by progerin expression.

Example 3

Farnesyltransferase Inhibitor Affects HGPS Nuclear Abnormalities

This example demonstrates that treatment of cells expressing progerin with a farnesyltransferase inhibitor reverses cellular morphology defects. The FTI used in this example, PD169451, was a gift from Pfizer.

Effect of FTI, PD169451, on Transiently Expressed GFP-Lamin a and GFP-Progerin

Normal and HGPS fibroblasts were plated on coverslips in 6 well plates 24 hours prior to transfection. Normal fibroblasts were transiently transfected with the GFP-lamin A or GFP-progerin expression constructs using FUGENE®6 transfection reagent (Roche). The following day, the medium was replaced with growth medium containing 0 nM, 100 nM, 500 nM or 1 mM of the FTI, PD169451. Forty-eight hours later the cells were washed two times with PBS (pH 7.2) and fixed for 20 min at 4° C. with 4% paraformaldehyde in PBS containing 62.5 µg/ml LPC palmitoyl and 1 U/ml rhodamine phalloidin (Molecular Probes) to stain the cytoskeleton. Following three washes with PBS, 10 µl of ProLong Gold mounting medium with DAPI (Molecular Probes) was applied and the coverslips, which were inverted onto a glass microscope slide.

Effect of FTI, PD169451, on the Nuclear Morphology of Normal and HGPS Fibroblasts Normal and HGPS fibroblasts were maintained in T75 tissue culture flasks with 0 nM, 10 nM, and 100 nM concentrations of the FTI, PD169451, added to the growth medium. The medium was changed every 2 days and the cells were split when they were approximately 80% confluent. Three days prior to each time point, a flask was trypsinized and cells were placed in chambered microscope slides (BD Biosciences) and maintained in the appropriate FTI concentration. Seventy-two hours later the cells were washed two times with PBS (pH 7.2) and fixed for 20 minutes at 4° C. with 4% paraformaldehyde in PBS containing 62.5 μg/ml LPC palmitoyl and 1 U/ml rhodamine phalloidin (Molecular Probes) to stain the cytoskeleton. Following three washes with PBS, 10 μl of ProLong Gold mounting medium with DAPI (Molecular Probes) was applied and the cells were overlaid with a coverslip.

Results and Discussion

Figure 7D:
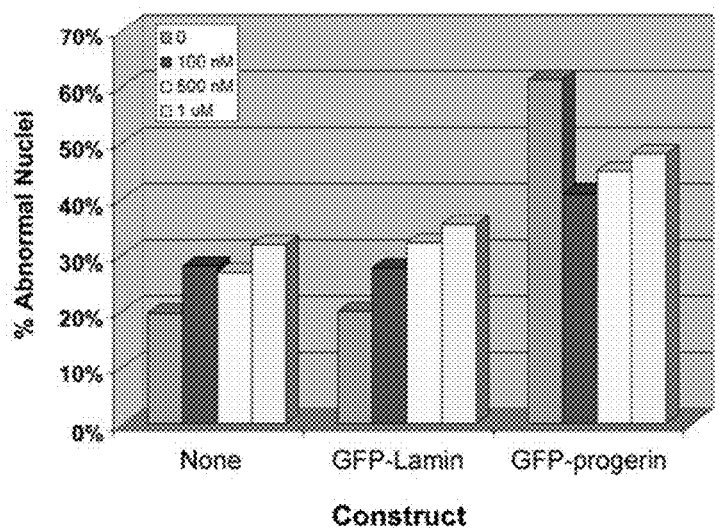
Figure 7E:
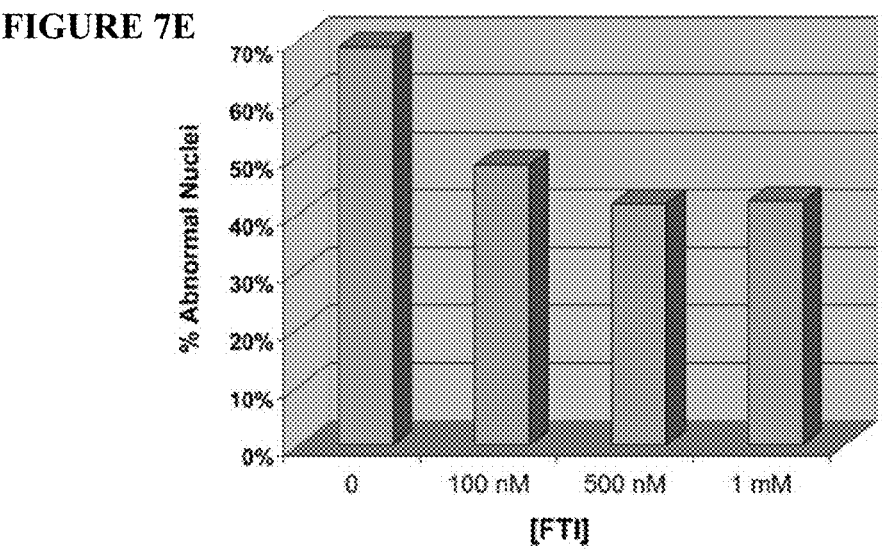

The effects of several concentrations of the specific farnesyltransferase inhibitor Pfizer PD 169451 on nuclear morphology and localization of lamin A and progerin were examined. Exposure of 100 nM FTI for 72 hours had a significant effect on the localization of transiently expressed GFP-lamin A and GFP-progerin (FIGS. 7A and 7B respectively). Lamin A and progerin were localized in very similar fashion to intranuclear filaments when exposed to the FTI rather than localizing to the nuclear periphery (compare FIGS. 7A and 7B with FIGS. 6A and 6B). In addition, short-term exposure to the FTI had a significant effect on the nuclear morphology of fibroblasts expressing GFP-progerin. These fibroblasts had a 33% decrease in the percentage of cells with abnormal nuclear morphology (FIG. 7D). To verify this result in HGPS fibroblasts, the AG11498 line was exposed to various FTI concentrations for three days. Treating these HGPS cells resulted in as much as a 40% drop in the percent of cells with abnormal nuclear morphology (FIG. 7E).

Figure 10:
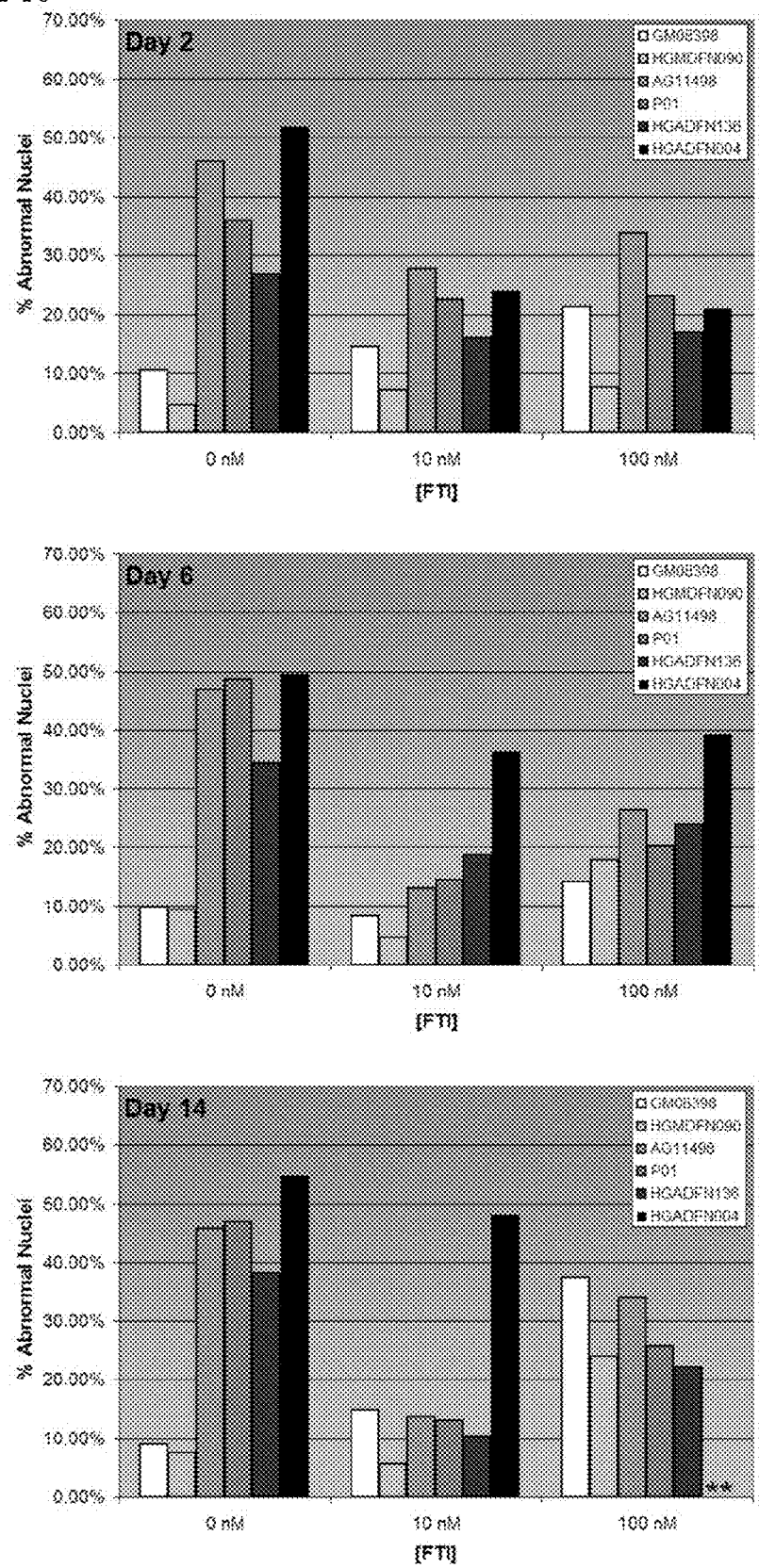
FIG. 10 illustrates the effect of long-term exposure to low doses of FTI (PD169451) on the nuclear morphology of normal (GM08398 and HGMDFN090) and HGPS (AG11498, P01, HGADFN136 and HGADFN004) fibroblasts. Fibroblasts were maintained in medium with 0 nM, 10 nM or 100 nM FTI. Cultures were plated in chambered microscope slides 24 hours prior to fixing with 4% paraformaldehyde for nuclear morphology studies. **—Too few cells to count. The HGADFN004 line failed to grow in 100 nM FTI to the 14 day time point. All cell lines were passage 6 at the beginning of the analysis except for HGADFN004, which was at passage 12.

A longer duration analysis on the effects of FTI on the nuclear morphology of normal and HGPS fibroblasts revealed that a sustained low dose of 10 nM substantially reduced the percentage of cells displaying abnormal nuclear morphology (FIG. 10). High doses of the FTI, greater than 200 nM, caused cells to stop dividing after a week to 10 days, and caused an increase in abnormal nuclear morphology in normal fibroblasts. However, 10 nM FTI did not substantially alter the nuclear morphology of normal cells and significantly lowered the percentage of abnormal nuclei in HGPS fibroblasts and in normal fibroblasts expressing GFP-progerin. Four HGPS cell lines were maintained in growth media containing 10 nM or 100 nM FTI. After two days exposure to 10 nM FTI the four HGPS cell lines demonstrated approximately a 40% reduction in the percent of cells with abnormal nuclei. At six days, the HGPS lines displayed a 72%, 70%, 45%, and 27% reduction in abnormal nuclei after six days of 10 nM FTI. After 14 days, three HGPS lines each had at least a 70% decrease in abnormal nuclei and one HGPS cell line (HGADFN004) had a 12% drop in abnormal morphology. This cell line failed to grow at the 14 day time point when exposed to 100 nM FTI. Exposure to the FTI causes some abnormal nuclear morphology in normal fibroblasts in a dose dependent manner.

Because the progerin protein maintains the farnesyl group, FTIs might improve the nuclear morphology of HGPS fibroblasts and normal fibroblasts expressing progerin by sequestering the mutant protein into the intranuclear filaments. These results showed a significant reduction in the abnormal nuclear phenotype in cells treated with an FTI. The FTI used in these experiments, PD169451, is an isoprene competitor which is specific for farnesyltransferase and does not inhibit the related geranylgeranyl transferase I. FTIs have been investigated as anticancer agents because farnesylation of Ras is necessary for Ras signaling and biological activity. Other FTIs have been used in clinical studies and are well tolerated by patients. The improvement in the morphology of the HGPS cells when exposed to low doses of the FTI indicates that these agents may be useful in treating the disease.

The effect of these drugs in animal models of HGPS may be analyzed to determine if there is improvement in the overall phenotype of the animals. The adverse effects of higher concentrations of the FTI on nuclear morphology and cell growth and the reduced effect on a higher passage HGPS line may indicate that there is a therapeutic window for effective concentrations of the drug and time of treatment for the patient.

Example 4

Effects of FTI Treatment on Expression of L647R Cleavage Mutant

The effects of exposure to the FTI PD169451 on cells expressing the lamin A L647R cleavage mutant are being tested. Based on the results observed with progerin (Example 3), it is believed that the FTI will cause the GFP-tagged L647R mutant to localize to intranuclear filaments, as observed when GFP-lamin A and GFP-progerin are expressed in cells exposed to the FTI. This result is expected because lamin A (and its mutant forms) must be farnesylated in order to be localized to the nuclear lamina. The FTI causes these forms of lamin A to accumulate in the interior of the nucleus. It is also predicted that the increase in abnormal nuclear morphology observed when the GFP-L647R mutant is expressed in normal fibroblasts will be alleviated by FTI treatment, as observed herein for normal fibroblasts expressing GFP-progerin when treated with the FTI.

By way of example, GFP-lamin A and GFP-progerin were expressed from TET-OFF® retroviral expression vector constructs that allowed for sustained expression and modulation of expression to address the possibility of results due to overexpression of the fusion proteins when the proteins were transiently expressed. In addition, a cleavage minus mutant, GFP-LA(L647R), was included to examine the effect of retaining the farnesyl group without the 50 amino acid deletion found in progerin.

When no tetracycline was present, the GFP fusions were expressed at relatively high levels as measured by Western blot (FIG. 11D).

Addition of 0.05 mg/ml tetracycline allowed for reduced expression of the GFP fusions such that near-endogenous levels were obtained, while 8 mg/ml tetracycline reduced, but did not altogether prevent, expression from these constructs (FIG. 11D). When GFP-progerin was stably expressed in normal fibroblasts (0.05 mg/ml tetracycline) at levels similar to progerin levels in HGPS fibroblasts, 10 nM FTI substantially reduced the percent abnormal nuclei by 71% (p<0.0001) (FIG. 11B).

When GFP-tagged L647R mutant was expressed at intermediate levels (0.05 mg/ml tetracycline), the increase in abnormal nuclear morphology was reduced 67% by exposure to 10 nM FTI (p<0.0001) (FIG. 11B). The improvement in abnormal nuclear morphology with intermediate expression levels of GFP-progerin and GFP-LA(L647R) was actually less profound at the higher concentrations of the FTI (100 nM) in comparison to the decrease observed for 10 nM (FIG. 11B). Treatment with 10 nM FTI could not overcome the effects of very high expression levels of the GFP-progerin or GFP-LA(L647R) that were obtained when no tetracycline was present to repress expression (FIG. 11A). However, the cleavage minus mutant may be more tractable to FTI treatment at the highest expression level, especially when exposed to 100 nM FTI, perhaps due to slightly lower expression levels. Some leaky expression was observed even at 8 mg/ml tetracycline, and these low levels did affect nuclear morphology, causing a moderate increase in the percent abnormal nuclei in the GFP-progerin and GFP-LA(L647R) cells (FIG. 11C). Thus, it is unlikely that the effects seen with the progerin constructs are due solely to protein over expression.

As with transient expression, stable expression of GFP-lamin A did not have a significant effect on nuclear morphology, and the GFP signal was evenly distributed at the nuclear periphery (FIG. 12A).

When GFP-progerin was expressed in normal fibroblasts at levels near what is observed in HGPS patients, nuclear aggregates at the periphery of the nucleus and intranuclear structures were observed, along with a substantial increase in abnormal nuclear morphology including folding and blebbing of the nuclear membrane (FIG. 12D). In addition, chromatin staining by DAPI was altered with a loss of staining often observed at the nuclear periphery and in regions adjacent to the progerin aggregates. Expression of intermediate levels of the cleavage minus mutant, GFP-LA(L647R), had very similar effects on localization of the GFP signal and on nuclear morphology as the GFP-progerin (FIG. 12G). Also, as observed in the transient expression studies, the FTI caused the GFP-lamin A and GFP-progerin to localize to intranuclear filaments when expressed in cells exposed to the FTI at 100 nM concentrations. Localization of GFP-tagged L647R mutant was also redistributed to intranuclear filaments when exposed to 100 nM FTI (FIG. 12I). However, 10 nM FTI did not lead to this drastic reorganization of GFP signal for any of the fusion proteins. Rather, alterations in GFP localization at this FTI concentration were less noticeable (FIGS. 12B, E and H).

Material included in this example was also published as Glynn & Glover, *Hum Mol Genet* 14: 2959-2569, 2005, Sep. 6, 2005, which is incorporated herein by reference in its entirety.

Example 5

Testing FTIs in HGPS, Experimental Protocols

This example describes production of a series of expression constructs for lamin A, progerin, and derivative proteins having mutations in the CAAX box (SEQ ID NO: 31). Methods are provided for analyzing such expression constructs in vivo. These methods are examples of analyses which can be used for determining the effectiveness of farnesyltransferase inhibitors (FTIs), potential FTIs, and other drugs and compounds, for reversing or reducing cellular defects caused by accumulation of progerin or other farnesylated proteins.

Mutant Construction

Figure 11:
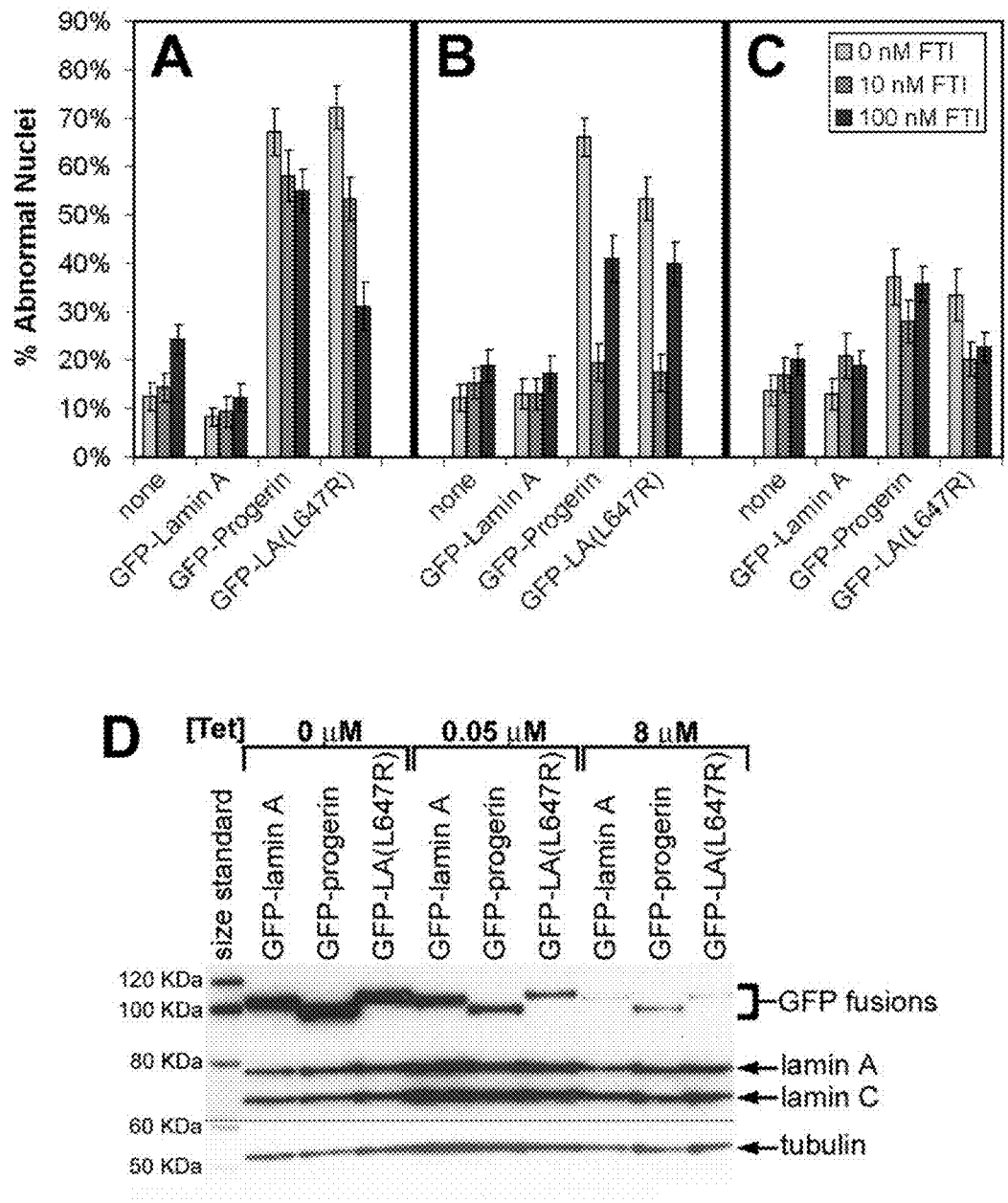
FIG. 11 (panels A-D) illustrates the effect of the FTI, PD169451, on the nuclear morphology of normal fibroblasts (GM08398) stably expressing GFP-lamin A, GFP-progerin and GFP-LA(L647R) using a retroviral TET-OFF® expression vector system (Clontech). Fibroblasts were maintained in medium with 0 nM, 10 nM or 100 nM FTI for 6 days.

A set of lamin A CAAX (SEQ ID NO: 31) mutants was generated, including CSIM (SEQ ID NO: 32) to CSIL (SEQ ID NO: 34) and to SSIM (SEQ ID NO: 33) mutants in constructs expressing wildtype or del150 lamin A proteins (Map 1 of FIG. 11). These expression constructs were made according to protocol using the QUIKCHANGE®II XL Site-Directed Mutagenesis Kit (Stratagene, LaJolla, Calif.). Primers were designed using QUIKCHANGE® site directed mutagenesis Primer Design (Stratagene), synthesized and purified by polyacrylamide gel electrophoresis at Integrated DNA Technologies, Inc. (Coralville, Iowa).

Primer sequences for the cDNA constructs were as follows: SSIM_Sense (SEQ ID NO: 11); SSIM_Anti-sense (SEQ ID NO: 12); CSIL_Sense (SEQ ID NO: 13); and CSIL_Anti-sense (SEQ ID NO: 14). Primer sequences for the minigene constructs were as follows: SSIM_Sense (SEQ ID NO: 15); SSIM_Anti-sense (SEQ ID NO: 16); CSIL_Sense (SEQ ID NO: 17); and CSIL_Anti-sense (SEQ ID NO: 18).

The "del150" lamin A framework provides a protein that has deleted from it the same 50-amino acids that are deleted in the HGPS protein. Map 1 of FIG. 13 provides an overview of these constructs. Specific examples of entire coding sequence (SEQ ID NOs: 19, 21, 23, 25, 27, and 29) for specific lamin A proteins (SEQ ID NOs: 20, 22, 24, 26, 28, and 30) are shown herein, which correspond respectively to constructs pEGFP_LA_myc_wildtype CSIM (the "normal" lamin A), pEGFP_LA_myc_wildtype CSIL, pEGFP_LA_myc_wildtype SSIM, pEGFP_LA_myc_del150 CSIM, pEGFP_LA_myc_del150 CSIL, and pEGFP_LA_myc_del150 SSIM.

Cell Culture: For immunofluorescence, HeLa cells were plated in chamber slides at 25,000 cells per chamber and cultured in DMEM containing 10% FBS, penicillin-streptomycin, and L-glutamine until 90-95% confluent prior to transfection.

Transfection: The following constructs were transfected by lipofection into the HeLa cells using the LIPOFECTAMINE® 2000 transfection reagent (Invitrogen, Carlsbad, Calif.) transfection procedure for DNA:
  pEGFP_LA_myc_del150 CSIL cDNA;
  pEGFP_LA_myc_del150 SSIM cDNA;
  pEGFP_LA_myc_wildtype CSIL cDNA;
  pEGFP_LA_myc_wildtype SSIM cDNA;
  pEGFP_LA_myc_wildtype CSIM cDNA (−control);
  pEGFP_LA_myc_del150 CSIM cDNA (+control); and
  mock transfection vector only (CMV driven EGFP vector with no insert).

Optionally, for each transfection, Western analysis can be performed to determine levels of progerin, prelamin, and lamin A. Using the myc-epitope tag engineered into these constructs, endogenous protein can be differentiated from the protein produced from the transfected construct.

Transfection efficiency was determined by the visual inspection of EGFP signal versus the DAPI staining of nuclei. Transfection efficiency for cells on all slides was estimated to be 30-40%.

Fluorescence and Electron Microscopy: At different time points (e.g., 48 and 72 hours after transfection), cells grown on coverslips were washed with PBS and fixed with 3.7% formaldehyde in PBS for 10 minutes at room temperature. After fixation, cells were washed three times with PBS, then permeabilized with 0.5% Triton X-100 in PBS for 5 minutes at room temperature, then rinsed with PBS. Cells were then overlaid with primary antibody, a rabbit anti-prelamin A from Dr. Michael Sinensky (1:5000 in PBS with 10% FBS; *Cancer Research* 54: 3229-3232; 1994), and incubated at room temperature for 1-2 hours. After removal of the primary antibodies, samples were washed once with PBS and incubated for 30 minutes in the dark at room temperature with a mixture of affinity-purified rhodamine-conjugated goat anti-rabbit IgG (2 μg/ml; Alexa fluor 594(red); Molecular Probes, Eugene, Oreg.), washed three times with PBS, and dehydrated in increasing concentrations of ethanol baths (70, 90, 100%) for two minutes per solution. 20 μl of a 50:50 Vectashield: Vectashield with DAPI (Vector Laboratories, Burlingame, Calif.) mixture was placed on the center of each pad and a coverslip was placed on top. Slides were then examined on a Zeiss Axioplan fluorescence microscope. LMNA was viewed using natural EGFP expression and prelamin A with the Sinensky Ab and Alexa Fluor594.

Results and Discussion

After 48 hours of incubation, the HeLa cells transfected with the pEGFP_LA_myc_wildtype CSIM cDNA construct (the negative control) appeared normal with the nuclear rim of transfected cells expressing the green EGFP marker for lamin A. These nuclei appeared to have normal ovoid and elliptical morphologies by both the DAPI and EGFP staining. In contrast, the positive control (the pEGFP_LA_myc_del150 CSIM cDNA progerin construct) displayed dramatic nuclear blebbing and lobulations by both DAPI and EGFP staining, identical to the blebbing seen in the nuclei of patients with HGPS.

The mutant pEGFP_LA_myc_wildtype SSIM cDNA construct demonstrated normal nuclear morphology, as would be expected. However, in this case, all of the EGFP staining appeared as aggregates within the nucleoplasm, with no EGFP at the nuclear rim, representing the new localization of the lamin A when it is unable to be farnesylated and directed to the nuclear membrane. Similarly, these nucleoplasmic aggregates were seen in the mutant pEGFP_LA_myc_del150 SSIM cDNA progerin construct. In this case however, there was no nuclear blebbing or lobulations as would be expected with the progerin construct.

The pEGFP_LA_myc_wildtype CSIL cDNA construct provided more of an intermediate picture. All the cells maintained their ovoid, elliptical shape in terms of morphology. Lamin A localization as determined by EGFP expression was a mix between many cells with normal nuclear membrane staining and many others with staining occurring only in the nucleoplasmic aggregates as seen in the SSIM mutants.

Likewise, the pEGFP_LA_myc_del150 CSIL cDNA construct also displayed a mixed phenotype, with a moderate amount of blebbing occurring in some cells mixed with many completely normal looking cells. Similarly, approximately half of the cells appeared to have normal lamin A EGFP staining at the nuclear rim, while the other half only expressed lamin A in nucleoplasmic aggregates.

After incubating transfected cells for 72 hours, all of the above results were unchanged except those concerning the CSIL mutants. In the case of the pEGFP_LA_myc_wildtype CSIL cDNA construct, there was a much greater percentage of cells appearing to express lamin A only in the nucleoplasm, and far fewer cells appearing like normal wildtype cells with lamin A only at the nuclear rim. The pEGFP_LA_myc_del150 CSIL cDNA progerin construct also appeared more like the SSIM del150 mutant, with far fewer blebbed cells and greater percentage of cells with normal ovoid, elliptical shapes and lamin A EGFP expression localized only in the nucleoplasm.

Example 6

Minigene Constructs for Lamin a Mutants

Additional constructs can be made, in which the intron between the LMNA exon 11 and 12 is included. A progerin protein can be produced from such constructs if a mutation that activates the cryptic splice site found in HGPS is included. These constructs are referred to as "minigene" constructs. An overview of a representative minigene construct is shown in Map 2 of FIG. 13.

The following constructs are made and used to transfect cells as described in Example 5:
  pEGFP_LA__75_myc_del150 CSIL minigene;
  pEGFP_LA__75_myc_del150 SSIM minigene;
  pEGFP_LA__77_myc_wt CSIL minigene;
  pEGFP_LA__77_myc_wt SSIM minigene;
  pEGFP_LA_myc_wt CSIM minigene (−control);
  pEGFP_LA_myc_del150 CSIM minigene (+control); and
  mock transfection vector only (CMV driven EGFP vector with no insert).

Cells transfected with minigene constructs are subjected to analysis as described in Example 5. These minigene constructs will be useful to determine if the efficiency of splicing may affect results such as those noted in Example 5.

Also contemplated are minigene constructs in which the expression of the lamin A/progerin/mutation protein is under inducible control. By way of example, tetracycline inducible constructs are contemplated (see, for instance, Map 3 of FIG. 13).

Example 7

Treatment with FTIs

Constructs such as those described in Examples 5 and 6 can be used in cell-based and animal expression systems to further characterize known FTIs and potential farnesyltransferase inhibitory compounds, in particular as regards the effectiveness of such compounds to ameliorate cellular defects associated with constitutive farnesylation of lamin A. By way of example, FTIs are reconstituted in DMSO and stored at −20° C. until used. The following concentrations of two specific FTIs will be used to determine their ability to prevent or reduce nuclear blebbing in the pEGFP_myc_del150 (CSIM) progerin construct and pEGFP_myc_wt (CSIM) LMNA construct:

| R115777 | SCH66336 |
| --- | --- |
| 50 nM (.05 µM) | 50 nM (.05 µM) |
| 100 nM (.1 µM) | 100 nM (.1 µM) |
| 200 nM (.2 µM) | 200 nM (.2 µM) |
| 500 nM (.5 µM) | 500 nM (.5 µM) |
| 1000 nM (1 µM) | 1000 nM (1 µM) |
| 2000 nM (2 µM) | 2000 nM (2 µM) |
| 5000 nM (5 µM) | 5000 nM (5 µM) |
| 10000 nM (10 µM) | 10000 nM (10 µM) |

Cells are cultured in media containing one of the indicated levels of FTI for 4-5 days or until 90-95% confluent prior to transfection. Transfected cell samples are examined by Western blot analysis to determine endogenous and transfected levels of progerin, prelamin, and lamin A.

Morphometric Analysis

To determine the ability of FTIs to prevent nuclear blebbing, 200 nuclei from both treated and untreated cell cultures transfected with the pEGFP_myc_del150 (CSIM) progerin construct or the pEGFP_myc_wt (CSIM) LMNA construct are scored either as lobulated, if they contain more than two lobulations, or not lobulated. These determinations are made by using a double-blind approach, followed by averaging the two data sets. Degree of farnesylation inhibition is determined by the percentage of cells demonstrating the presence of prelamin A.

Contour analysis as in Goldman et al. (*Proc. Natl. Acad. Sci. U.S.A.* 8963-8968, 2004) can be used to accurately quantitate nuclear morphology irregularities. To analyze the changes in nuclear shape, the perimeter and the area of nuclei is measured in cells at different passages. This measurement will be carried out on the midsection of the nucleus by using the overlay/measure function in the LSM software (Zeiss). To determine the extent of nuclear lobulation, 50-200 randomly selected nuclei are measured per passage and the nuclear roundness or contour ratio ($4\times area/perimeter^2$) is calculated. The contour ratio for a circle is one. As the nucleus becomes more lobulated, this ratio approaches zero. To calculate the perimeter length and area, the outline of nuclei is traced with a closed loop drawing tool using images captured from cells prepared for immunofluorescence with LA Ab (Anti-lamin A/C Monoclonal Antibody, Unconjugated, Clone JoL2, MAB3211; Chemicon, Temecula, Calif.). Lamin fluorescence that is associated with the edge of the lobulations and deep invaginations that typify the surface of later-passage HGPS cells will be included. Significance of the resultant observations can be measured using, for instance, a two-tailed Student t test.

Example 8

Animals Engineered to Express Lamin A/Progerin or Mutants Thereof

Mutant or transgenic organisms that under-express or over-express lamin A protein are useful for research and characterization, for instance, the characterization of FTIs and potential inhibitory molecules. They also allow insight into the physiological and/or pathological role of lamin A in a healthy and/or pathological organism, for instance in characterization of aging and aging-related diseases and conditions, including progeria and atherosclerosis. These mutants are "genetically engineered," meaning that information in the form of nucleotides has been transferred into the mutant's genome at a location, or in a combination, in which it would not normally exist. Nucleotides transferred in this way are said to be "non-native." For example, a non-LMNA promoter inserted upstream of a native LMNA encoding sequence would be non-native. An extra copy of an LMNA gene on a plasmid, transformed into a cell, would be non-native.

Mutants may be, for example, produced from mammals, such as mice, that either over-express lamin A or under-express lamin A, or that do not express lamin A at all, or that express a mutant form of lamin A (such as the splice variant described herein), that express one or more of these proteins under control of an inducible promoter, and so forth. Over-expression mutants can be made by increasing the number of LMNA genes in the organism, or by introducing an LMNA gene into the organism under the control of a constitutive or inducible or viral promoter such as the mouse mammary tumor virus (MMTV) promoter or the whey acidic protein (WAP) promoter or the metallothionein promoter. Mutants that under-express lamin A may be made by using an inducible or repressible promoter, or by deleting the LMNA gene, or by destroying or limiting the function of the LMNA gene, for instance by disrupting the gene by transposon insertion.

A gene is "functionally deleted" when genetic engineering has been used to negate or reduce gene expression to negligible levels. When a mutant is referred to in this application as having the LMNA gene altered or functionally deleted, this refers to the LMNA gene and to any ortholog of this gene. When a mutant is referred to as having "more than the normal copy number" of a gene, this means that it has more than the usual number of genes found in the wild-type organism, e.g., in the diploid mouse or human.

A mutant mouse or other animal over-expressing normal or mutant lamin A may be made by constructing a plasmid having an LMNA encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

In particular, one example transgenic animal is a mouse model of HGPS, duplicating one of the G608G mutations. The mouse sequence is perfectly identical at this region of the coding sequence, so this would produce the same kind of consequence for lamin A as in the human.

In addition to knock-out systems, it is also beneficial to generate "knock-ins" that have lost expression of the wild-type protein but have gained expression of a different, usually mutant form of the same protein.

By way of example, the dominant mutant lamin A protein (progerin) provided herein, or any of the other mutant lamin A, progerin, or progerin-like proteins described herein, can be expressed in a knockout background, such as a mutant mouse that has been rendered defective or selectively defective (e.g., inducibly knocked-out) for LMNA expression, in order to provide model systems for studying the effects of treatment with FTIs or potential farnesyltransferase inhibitory compounds. In particular embodiments, the resultant knock-in organisms provide systems for studying aging, arteriosclerosis, and/or HGPS-like conditions.

Those of ordinary skill in the relevant art know methods of producing knock-in organisms. See, for instance, Rane et al. (*Mol. Cell Biol.*, 22: 644-656, 2002); Sotillo et al. (*EMBO J.*, 20: 6637-6647, 2001); Luo et al. (*Oncogene*, 20: 320-328, 2001); Tomasson et al. (*Blood*, 93: 1707-1714, 1999); Voncken et al. (*Blood*, 86: 4603-4611, 1995); Andrae et al. (*Mech. Dev.*, 107: 181-185, 2001); Reinertsen et al. (*Gene Expr.*, 6: 301-314, 1997); Huang et al. (*Mol. Med.*, 5: 129-137, 1999) by way of example.

Example 9

Mouse Systems for Testing FTIs

Mice from positive progerin-expressing lines, or lines expressing other abnormal lamin proteins, can be treated with differing doses of FTIs and compared with controls for the prevention or amelioration of any phenotypic changes (for instance, growth changes, ability to reproduce, hair loss, skin changes, vascular changes, and nuclear blebbing).

One specific dosing regimen for examining FTI effects in transgenic mice is as follows, administered (e.g., orally, such as by oral gavage) over differing time periods, for instance 10 days to 3 weeks:

| R115777 | SCH66336 |
| --- | --- |
| 10 mg/kg BID | 10 mg/kg BID |
| 25 mg/kg BID | 25 mg/kg BID |
| 50 mg/kg BID | 50 mg/kg BID |
| 100 mg/kg BID | 100 mg/kg BID |

Alternatively, an FTI can be provided in food. By way of example, an FTI (such as FTI R115777) can be provided in by way of animal (e.g., mouse) feed at doses as follows: 450 mg/kg of feed, 150 mg/kg of feed, and 0 mg/kg of feed (as a negative control). One of ordinary skill will recognize that all of these dosages are examples only, and can be varied.

Example 10

Vascular Disease Process in Hutchinson-Gilford Progeria Syndrome

HGPS skin fibroblasts displayed disruption of nuclear architecture, premature senescence, apoptosis, decreased hyaluronan secretion and decreased matrix metalloproteinase secretion. The disruption of nuclear architecture and apoptosis has been examined in vascular smooth muscle cells (VSMC) transfected with progerin. In addition, by transfecting the progeria minigene into normal VSMC and endothelial cells (EC), it was shown that these cell types produce progerin. It was hypothesized that disruption of nuclear structure and function culminates in premature cell death and cell senescence of VSMC and EC. It is believed that these features can be improved or reversed by blocking post-translational processing of lamin A using farnesyltransferase inhibition, and that elimination of progerin will restore normal function to progeria and other laminopathy cells.

LMNA is a 12 exon gene that initially produces a pre-lamin A which must be processed both outside of the nucleus via isoprenylation of a carboxy terminal CAAX motif (SEQ ID NO: 31), cleavage of the last three amino acids, and methyl esterification, and inside of the nucleus via proteolysis of its terminal 18 amino acids to become mature lamin A (Sinensky et al., *J Cell Sci* 107(Pt 1):61-7, 1994). The deletion in HGPS probably does not affect the ability of Progerin to localize to the nucleus or to dimerize (as normal lamin A does), because the components needed for nuclear localization and dimerization are not deleted. The ability to isolate progerin from cells (FIG. 15), yet detect lamins only in the nucleus via anti-lamin A using immunofluorescence (FIG. 19), supports this hypothesis.

A. Senescence and Apoptosis

Many of the features of HGPS, such as atherosclerosis and bony changes, may be at least partially attributed to premature cellular senescence or apoptosis in vivo. The data demonstrate that HGPS fibroblasts have less than half of the growth potential and show premature apoptosis as compared to normal skin fibroblasts from age-matched or older donors. These investigations have been extended to HGPS-transformed vascular cell types and senescence and apoptosis have been addressed in the principal cell types involved in abnormalities of vasculature (VSMC and EC).

Cell Culture: VSMC and EC were kindly provided by Richard Karas, MD, PhD, New England Medical Center, Boston, Mass. HGPS and normal fibroblasts cells were obtained from the Coriell Cell Repositories and the Progeria Research Foundation.

Dermal fibroblasts were maintained in MEM with Earl's Salts (Gibco, 10370-021) (EMEM), 1× Pen./Strep. (100 U/ml P, 100 µg/ml S), 2 mM L-Glutamine and 15% fetal bovine serum, under 5% $CO_2$. Cell numbers were obtained at every passage using a hemocytometer and Trypan Blue cell viability staining. VEC were grown on gelatin (Sigma #G1393) in Medium 199 in Earl BSS with 2 mM L-glutamine, 0.05-0.1 mg/mL Endothelial Cell Growth Supplement (Fisher #CB40006B)*, 0.10 mg/ml Heparin (Sigma H3149), 1× Pen/Strep, and 10% fetal bovine serum. VSMC were grown with either DMEM+10% Fetal Bovine Serum+2 mM L-glutamine (1×) and 1× Pen/Strep (as above) or Clonetics® Media Systems SmGM2 media (CC-3182).

Cell cultures were fed every 2-3 days, and split when necessary using 0.05% trypsin.

Assay for growth rate: Growth rate was assessed by measuring population doubling times. Population doublings (PD)=$\log_2(N/N_0)$, where N=final cell number and $N_0$=starting cell number. Therefore, PD=$(\log_{10}N/N_0)/0.301$ and PD time=Total incubation time/PD.

Senescence-associated β-galactosidase (SA-β Gal) and cell cycling: Pre-confluent cultured cells were fixed with 3% formaldehyde and stained with 1 mg/ml 5-bromo-4-chloro-3-indolyl β-D-galactoside (X-gal), 40 mM citric acid/sodium phosphate buffer pH 6.0, 5 mM potassium ferrocyanide, 5 mM ferricyanide, 150 mM sodium chloride and 2 mM magnesium chloride. At pH 6.0 the solution specifically stains senescent cells (cells in G1-like arrest) blue in the perinuclear region (Dimri et al., *Proc Natl Acad Sci USA*. 92:9363-9367, 1995). Exposure to 10 µCi/ml-$^3$H-thymidine followed by fixation and development for silver grains was used to assay cell cycling.

Results and Discussion

In vitro, fibroblasts normally progress to senescence, and this is considered a hallmark of "aging" in vitro. Fibroblasts from older donors senesce more quickly than those from younger donors (Martin et al., *Laboratory Investigation* 23:86-92, 1970). There are conflicting reports on the growth potential of HGPS fibroblasts (Goldstein, *J Inv. Derm.* 73:19-23, 1979). Seven different HGPS skin fibroblast lines have been cultured, and they have senesced completely, or have reached Phase 3 growth, as indicated by an increase in doubling time and changes in morphology (Hayflick, *J Am Geriatr Soc* 22(1):1-12, 1974), between passages 6 and 18 (Table 1). This is less than half of the growth potential of normal skin fibroblasts from age-matched or older donors (Schneider & Mitsui, *Proc. Nat. Acad. Sci.* 73:3584-3588, 1976) (FIG. 17). In general, the senescing HGPS cells are increased in size and show characteristic intracellular changes associated with senescence, whereas normal fibroblasts after similar passage number do not. Another hallmark of senescence is cytoplasmic staining with SA-β gal (Dimri et al., *Proc Natl Acad Sci USA*. 92:9363-9367, 1995). A higher percentage of HGPS fibroblasts stained positively for SA-βgal activity than normal fibroblasts of similar passage, while the same normal fibroblasts incorporated a much higher percentage of $^3$H-thymidine than the HGPS fibroblasts, indicating increased cell cycling.

TABLE 1*

Percentages of cycling and senescent cells

| | Normal Control | | | | HGPS | | |
|---|---|---|---|---|---|---|---|
| Passage # | % SA-β gal | % Thymidine | PD time (h) | Passage # | % SA-β gal | % Thymidine | PD time (h) |
| 12 | 6 | 80 | 44.8 | 9 | 11 | 67 | 132 |
| 10 | 20 | 90 | 58.9 | 13 | 56 | 22 | 236 |
| 16 | 0 | 85 | 54.5 | 16 | 48 | 15 | 431 |

*each line represents a separate experiment; 200 cells randomly assayed

B: Nuclear Morphology and Disease Phenotype

Immunofluorescent Staining for Lamin A and Nuclear Morphology: Cells were seeded into glass coverslips, methanol fixed, incubated in primary (mouse anti-human lamin A/C monoclonal used at 1:10, MAB3211, Chemicon) and fluorescent secondary (Alexa Fluor 488 goat anti-mouse IgG used at 1:3000, A-11001, Molecular Probes) antibodies and counter-stained with DAPI. Confocal Microscopy can also be used to better identify nuclear blebbing.

Assays for apoptosis: The occurrence of apoptosis in normal versus HGPS-transformed cultures was determined using an Annexin V binding assay (Vybrant® Apoptosis Assay Kit #2, Molecular Probes) adapted for adherent cell cultures. Alternatively, caspase analysis may be used for apoptosis analysis, using known protocols.

Results and Discussion

Alteration of lamin A produces blebbing of nuclei in cultured HGPS fibroblasts (Eriksson et al., *Nature* 423(6937): 293-298, 2003) and the data show that this nuclear blebbing increases significantly with passage number. Early passage, vigorously growing, normal fibroblasts with low levels of senescence associated β-galactosidase (SA-β gal) staining (6%; FIG. 17, Point A) had normal, round nuclei (FIG. 19A), a blebbing rate of 12% (Table 2), and virtually no apoptotic cells (FIG. 18). This rate increased to 22% blebbing at passage 12. Early passage, vigorously growing, HGPS fibroblasts with correspondingly low levels of SA-β gal staining (6%; FIG. 17, Point C) demonstrated abnormally blebbed nuclei in 11% of cells and this percentage grew to 28% at passage 12 and then 50% at passage 14, when growth curves demonstrated almost complete senescence in the HGPS fibroblasts (Table 2).

TABLE 2

Percentage of nuclei exhibiting abnormal morphology (blebbing).

| Condition | passage number | # cells counted | # blebs | % blebs |
|---|---|---|---|---|
| Normal | p9 | 113 | 14 | 12.4% |
| Normal | p12 | 102 | 22 | 21.5% |
| HGPS htert | p28 | 106 | 17 | 16.0% |
| HGPS htert | p34 | 111 | 26 | 21.6% |
| HGPS | p6 | 120 | 13 | 10.8% |
| HGPS | p12 | 125 | 35 | 28.0% |
| HGPS | p14 | 150 | 75 | 50.0% |

The percentage of cells with nuclear blebbing increased with passage number in HGPS fibroblasts (Table 2). The potential causal association of nuclear blebbing and thus nuclear membrane instability with senescence and apoptosis in HGPS-transformed vascular cells is being studied further. To understand whether blebbing precedes or coincides with these events, cultures are co-stained for senescence or apoptosis and for nuclear morphology at varying cell passages.

C: ECM and Vascular Disease in HGPS

There is considerable indication, both in vivo and in vitro, that HGPS is a disease heavily involving abnormalities in the extracellular matrix, with increased collagen and elastin secretion, disorganized dermal collagen, and decreased decorin over normal controls (reviewed in Davidson et al., *Ciba-Found-Symp.* 192:81-99, 1995). Extracellular matrix molecules have both structural and cell signaling functions in skin, bone, and the cardiovascular system all severely affected in HGPS.

Reduction in hyaluronic acid (HA)-dependent pericellular matrices (PCM) (HA-PCM) may be involved in prevention of cellular senescence by acting as a protective sink for reactive oxygen species. Reactive oxygen species are produced as a normal consequence of the aerobic cellular metabolism. However, oxidative stress induces senescence and apoptosis and is implicated in etiology of a long list of diseases, including HGPS (Yan et al., *Biochemical and Biophysical Research Commun.* 257:163-167, 1999) and atherosclerosis (reviewed in Napoli et al., *J. Cell. Biochem.* 82:674-682, 2001), as well as the process of normal aging (Floyd et al., *Exp. Gerontol.* 36:619-640, 2001). Abnormalities in the extracellular matrix (ECM) may be key components to disease process in HGPS. Hyaluronan-cell interactions promote cell growth and survival signaling pathways. Published microarray analyses (Csoka et al., *Aging Cell* 3:235-43, 2004) of HGPS fibroblasts and our protein data show dramatic decreases in stromelysin (MMP-3) over normal control fibroblasts.

MMP's are key components of ECM restructuring for angiogenesis. By measuring the size of HA-PCM and MMP-3 in VSMC and EC, a correlation between premature cellular senescence and decreased matrix assembly in HGPS cultures can be substantiated.

HA-PCM assay: HA-PCM size was analyzed using a well-established particle exclusion assay (Knudson & Toole, *Dev Biol* 112(2):308-318, 1985). Briefly, a suspension of formalin-fixed erythrocytes (0.8 ml of $10^8$ cells/ml in 0.1% BSA in PBS) was added to a 35 mm dish of sub-confluent fibroblasts, settled, and photographed using a 4.3 megapixel digital camera (VersaCam Digital Imaging Outfit, Chestnut Hill, Mass.). Morphometric analysis of the HA-PCMs was determined using Scion Image Beta 4.0.2 software (Scion Corp., Frederick, Md.) for analysis of cell perimeter and matrix perimeter.

MMP-3 Analysis: MMP-3 can be assayed from confluent culture conditioned media using a standard ELISA kit (Amersham MMP3 ELISA kit (RPN2613)).

Results and Discussion

Hyaluronan production by normal and HGPS fibroblasts was measured. Hyaluronan content in pre-senescent HGPS and age-matched normal control fibroblasts was analyzed using fluorophore-associated carbohydrate electrophoresis analysis, revealing a 70% decrease in both the cell layer and culture medium over age matched control cultures.

TABLE 3

Hyaluronan Content in Fibroblast Cultures (ng/ml)*

|  | Cell Layer | Media Layer |
|---|---|---|
| Normal Pre-senescent | 1005 | 572 |
| HGPS Senescent | 136 | 343 |

*age and passage-matched (n = 2); ELISA-like assay

Dermal fibroblasts, VSMC and EC exhibit highly hydrated HA-PCMs that can be visualized indirectly by their ability to exclude particles (see methods section). Preliminary data suggested that the HA-PCM thickness of senescent HGPS fibroblasts was 12-fold decreased over age matched pre-senescent HGPS fibroblasts and 22-fold decreased over normal dermal fibroblasts (Table 4).

TABLE 4

Mean HA-PCM radius in cultured fibroblasts (μm)*

| Normal Pre-senescent | 6.7 |
|---|---|
| Normal Senescent | 1.5 |
| Progeria Pre-senescent | 3.7 |
| Progeria Senescent | 0.3 |

*$1 \times 10^4$ cells were plated per 35 mm dish, and HA-PCM radii were measured on 25 cells randomly chosen prior to addition of fixed red blood cells.

The data substantiate a correlation between premature cellular senescence and decreased matrix assembly in HGPS fibroblast cultures. Large polymeric hyaluronan protects against oxidative stress by absorbing free radicals and inhibiting pro-inflammatory cytokine formation (reviewed in Neumann et al., *FEBS Letters* 453:283-7, 1999). This evidence suggests that changes in hyaluronan (previously named hyaluronic acid or hyaluronate) precede onset of standard senescent characteristics in HGPS fibroblasts but resemble changes that also occur during senescence of normal fibroblasts. These results are of broad interest because hyaluronan is involved in the development of atherosclerotic lesions and has also been found to play a role in cell survival signaling cascades.

Matrix Metalloproteinase-3 (MMP-3) has been associated with cellular senescence (Parrinello et al., *J. Cell Sci.* 118: 485-496, 2005), atherosclerotic plaque formation (Doherty et al., *Mayo Clin. Sci.* 79:197-210, 2004), and HGPS (Csoka et al., *Aging Cell* 3:235-243, 2004; Ly et al., *Science* 287:2486-2492, 2000). A complete absence of MMP-3 was observed in HGPS dermal fibroblast cultures, as compared to normal control dermal fibroblast cultures (FIG. 20). This molecule therefore serves as a biomarker of cellular disease in HGPS, which would be normalized with effective treatment of disease process, and helps to elucidate the mechanism of disease in HGPS.

D: Vascular Changes and HGPS

Atherosclerosis in HGPS is a diffuse process, involving the large vessels, the coronary arteries, and distal vasculature. To date there have been fewer than 20 autopsies described on children with HGPS (reviewed in Stehbens et al., *Cardiovasc Pathol* 10(3):133-136, 2001). These studies note focal atherosclerotic plaques throughout large and small arteries, including all coronary artery branches, interstitial fibrosis and stenosis. Plaques are markedly calcified with cholesterol crystals evident. Microscopy reveals thickened and almost acellular hyaline fibrosis. Notably, two autopsies report a paucity of medial smooth muscle cells, with acellular fibrous tissue predominating in the media. Intimal and medial collagen have been noted as disorganized and of small diameter. However, a major problem with studying autopsy specimens is that we are observing the end stage of a complicated process (Zhang et al., *Am J Pathol.* 143:496-506, 1993).

Calcification of both vascular intima and media are early events in the development of atherosclerotic plaques in aging individuals and those with diabetes (Cooper et al., *Am J Hypertens.* 14:475-86, 2001). Apoptosis occurs in vascular smooth muscle cells (VSMC) prior to the development of calcification (Proudfoot et al., *Circulation* 106:3044-50, 2002), and may even be required for calcification to occur. Vascular calcification is implicated in both pathological and in vitro studies as a requisite event in plaque formation. Therefore apoptosis may be a key element to development of disease in HGPS. Premature apoptosis occurs in HGPS fibroblasts (FIG. 18).

E: Creating HGPS in Vascular Cells:

One way to begin understanding the initial phases of atherosclerosis in HGPS is to study the VSMC and EC at initial phases of disease. This can be achieved by introducing the HGPS gene, or constructs expressing similar mutant forms of lamin A, into normal VSMC and EC. If progeric VSMCs have limited capacity for proliferation, as do fibroblasts (FIG. 15), then the clonal and proliferative requirements of VSMC in plaque initiation may lead to early senescence or apoptosis of VSMC and eventually result in the lack of VSMC seen at autopsy.

Constructs were created that allowed VSMC and EC to demonstrate natural splicing capabilities, thus demonstrating that these cell types do express progerin in vivo.

Recombinant DNA constructs using site directed mutagenesis: Briefly, RT-PCR products of LMNA were generated using RNA from normal dermal fibroblasts and the GC-rich protocol for SUPERSCRIPT® reverse transcriptase First-Strand Synthesis System for RT-PCR (Invitrogen) with Platinum Taq High Fidelity and PCRx Enhancer System (Invitrogen). The LMNA cDNA was then cloned using a pCR2.1-TOPO cloning vector (Invitrogen) and One Shot TOP10 Chemically Competent *E. coli* (Invitrogen).

Normal Lamin A: The normal lamin A cDNA was cloned via RT-PCR from RNA extracted from normal human dermal fibroblast line GM00969D (Coriell Repositories). The cDNA was inserted into the pEGFP-C mammalian expression vector (Clontech) at the EcoRI site (FIG. 14).

Progerin: The mutant HGPS splice variant of lamin A was created from the normal lamin A construct via site directed mutagenesis (Stratagene). Bases 1818 through 1968 were deleted from exon 11 producing a cDNA that codes for the mutant protein "progerin" with a GFP fused to its N terminus (FIG. 14).

Minigene: A third construct was created, which contained the intron between exon 11 and 12 as well as the c-to-t point mutation in codon 608 in exon 11 (G608G) responsible for HGPS. The presence of this intron allows a cell expressing the construct to recognize the cryptic splice site caused by the point mutation, and splice both the normal and abnormal lamin A products (FIG. 14).

Quantitative PCR: Total RNA was extracted from cells harvested via trypsinization using the RNEASY® Mini RNA isolation Kit (Qiagen). Five hundred nanograms (500 ng) of each mRNA template was reverse-transcribed with an oligo (dT) primer using the SUPERSCRIPT II® reverse transcriptase first strand cDNA synthesis kit (Invitrogen). Quantitative PCR was then carried out on a Stratagene MX 4000 apparatus using the QUANTITECT® SYBR Green PCR analysis kit from Qiagen with the following primers: Forward (SEQ ID NO: 9) and Reverse (SEQ ID NO: 10).

Vascular cells (EC, FIG. 16A; coronary artery SMC, FIG. 16B; radial artery SMC, FIG. 16C) were electroporated and exposed to either a progerin minigene or LMNA-lamin A minigene. These cell types were demonstrated to splice the minigene; the amplified, processed transcript (489 base pairs) is indicated with an arrow.

Protein Electrophoresis and Western Blotting: Protein isolated from cultures are probed using primary mouse anti-human lamin A/C monoclonal used at 1:200, MAB3211, Chemicon, followed by secondary antibody (sheep anti-mouse Fab IgG-HRP conjugate, 1:3000, Amersham) and visualized for band intensity using the Eagle Eye II Still Video System (Stratagene).

Example 11

Inhibiting Farnesylation of Progerin Prevents the Characteristic Nuclear Blebbing of Hutchinson-Gilford Progeria Syndrome It was hypothesized that retention of the farnesyl group causes progerin to become permanently anchored in the nuclear membrane, disrupting proper nuclear scaffolding and causing the characteristic nuclear blebbing seen in HGPS cells. Progerin's central rod domain then allows dimerization with mature, nonfarnesylated lamin A and assembly into a multiprotein complex, resulting in dominant negative disruption of the nuclear scaffolding and underlying heterochromatin, and leading to the characteristic nuclear blebbing seen in HGPS (Goldman et al., *Proc. Natl. Acad. Sci. USA* 101:8963-8968, 2004). It was further hypothesized that farnesyltransferase inhibitors (FTIs) would inhibit the formation of progerin, and that decreasing the amount of this aberrant protein could potentially improve disease status in HGPS and other laminopathies.

In this study, the ability of both genetic mutation and pharmacological treatment to prevent the dysmorphic nuclear phenotype seen in HGPS was examined. The terminal CSIM sequence (SEQ ID NO: 32) in progerin was mutated to SSIM (SEQ ID NO: 33), a sequence that cannot be farnesylated.

Material included in this example was also published as Capell et al., *Proc. Nat. Acad. Sci.* 102:12879-12884, Sep. 6, 2005, which is incorporated herein by reference in its entirety.

Materials and Methods

Constructs and Mutagenesis. The pEGFP-myc-LA vector (referred to here as wild-type lamin A-CSIM) and the LAΔ50 (referred to here as progerin-CSIM) vector were created as previously described (Goldman et al., *Proc. Natl. Acad. Sci. USA* 101:8963-8968, 2004) and encode green fluorescent protein (GFP)-tagged lamin A fusion proteins. The wild-type lamin A-CSIL, progerin-CSIL, wild-type lamin A-SSIM, and progerin-SSIM mutations were created by site-directed mutagenesis using the following oligos: for CSIL (SEQ ID NO: 13) and for SSIM (SEQ ID NO: 11) (QUIKCHANGE® II XL Site-Directed Mutagenesis Kit, Stratagene).

Cell Culture. Cell lines used were the normal human fibroblast line, AG06299, and HGPS fibroblast lines: AG06917, AG11513, and AG11498 (obtained from the NIA Aging Cell Culture Repository, Coriell Institute for Medical Research, Camden, N.J.). Fibroblasts were cultured in minimal essential medium (MEM; Invitrogen/Gibco) supplemented with 15% FBS (HiClone), 2 mM L-glutamine, penicillin (50 U/ml) and streptomycin (50 mg/ml). HeLa and HEK-293 cell lines were cultured in DMEM (Invitrogen/Gibco) supplemented with 10% fetal bovine serum and antibiotics.

Transient Transfections. Approximately 25,000 cells were plated per chamber of 4-chamber slides (Lab-Tek, Nalge Nunc International, #154526). After twenty-four hours, HeLa and HEK-293 cell lines were transiently transfected with 0.8 μg of each construct using LIPOFECTAMINE®2000 transfection reagent (Invitrogen) under standard conditions.

FTI Treatment. At the time of transient transfection, HeLa cells were treated with one dose of 0, 0.5, 1.0, or 2.0 μM of the selective FTI lonafarnib [Sarasar, SCH66336, (Schering-Plough)]. HEK-293 cells were treated with one dose of 0, 1, 2, 5, or 10 μM of the selective FTI L-744832 (Biomol). In addition, NIH-3T3 cells were treated with 5 μM of FTI-2153, which is highly selective for FTase, or GGTI-2166, which is highly selective for GGTase I (kind gifts of Said M. Sebti and Andrew D. Hamilton). These FTIs have the same mechanism of action and can be used interchangeably to inhibit protein farnesylation in vitro. However, only lonafarnib is a clinical candidate. Normal and HGPS fibroblasts were treated with one daily dose of 0, 0.5, 1.0, or 2.0 μM of lonafarnib for 3 days.

GFP Localization and Fluorescence Microscopy. Forty-eight hours following transient transfection, the HeLa and HEK-293 cells were visualized for GFP localization using an LSM510 confocal microscope (Zeiss). Following three-day treatment with lonafarnib, HGPS fibroblasts were washed two times with phosphate-buffered saline (PBS) (pH 7.2) and fixed for 10 minutes at room temperature with 1% paraformaldehyde in PBS. Following three washes with PBS, the cells were permeabilized for 5 minutes at room temperature with 0.5% Triton X-100 in PBS and blocked with 5% horse serum for 30 minutes at room temperature. Cells were then incubated for one hour at room temperature with the primary antibody diluted in blocking solution, a polyclonal mouse anti-human lamin A/C at 1:10 (mAb3211, Chemicon). Three more washes with PBS were then followed by incubation with the secondary antibody, Alexa 488-conjugated donkey anti-mouse IgG (Molecular Probes), for 45 minutes and three additional PBS washes. Slides were then mounted with mounting medium containing DAPI (Vector Laboratories).

Mobility Shift Experiments. NIH-3T3 cells, grown in DMEM-H (Gibco/Invitrogen) supplemented with 10% GCS at 37° C. in 10% $CO_2$, were transiently transfected with either empty vector, progerin-CSIM or progerin-SSIM using LIPOFECTAMINE®-Plus transfection reagent (Invitrogen) according to the manufacturer's instructions. Transfected cells were treated for 48 hours with vehicle (DMSO) or inhibitors of prenylation (5 μM FTI-2153, 5 μM GGTI-2166 or both). Cells were lysed directly in 2× Laemmli loading buffer and total cell lysates were resolved on 8% SDS PAGE. Proteins were transferred to Immobilon PVDF (Millipore), blotted with anti-GFP mAb (clone B34, Covance) and visualized using SUPERSIGNAL™ enhanced chemiluminescence (Pierce).

Morphometric Analysis. To examine the overall percentage of blebbed cells in cells with different amounts and lengths of FTI treatment, 200 nuclei were classified as either blebbed, if they contained two or more lobulations, or not blebbed, as previously described (Goldman et al., *Proc. Natl. Acad. Sci. USA* 101:8963-8968, 2004). These classifications were done by three independent observers, all blinded to the specifics of the cells being examined, followed by averaging three independent data sets. Armitage's trend test (Armitage, *Biometrics* 11:375-386, 1955) was used to test for a dose-dependent response for each cell type.

Results

While both B-type lamins and lamin A are farnesylated and carboxymethylated, unique to lamin A is a second cleavage step that occurs inside the cell nucleus causing the removal of an additional 15 C-terminal amino acids from the mature protein, including the farnesylated cysteine. This final cleavage step, and the resulting loss of the farnesyl anchor, is believed to release prelamin A from the nuclear membrane and allow it to be inserted into the nuclear lamina. In HGPS, although preprogerin can be farnesylated, its internal deletion of amino acids 606-656 removes the endoprotease recognition site necessary for executing the final cleavage step (FIG. 21).

We sought to examine the ability of CAAX box (SEQ ID NO: 31) mutants or FTIs to block the nuclear blebbing that is the cellular hallmark of the HGPS phenotype. To examine the effects of inhibiting all prenylation, missense mutations of the cysteine residue of the CSIM motifs (SEQ ID NO: 32) of wild-type lamin A and progerin were generated (designated SSIM). These constructs, marked for visualization by an amino-terminal GFP fusion, were transfected into HeLa cells and imaged after 48 hours. Without prenylation, all of the prelamin A was relocated from its normal location at the nuclear periphery into nucleoplasmic aggregates, and there was no progerin-induced nuclear blebbing (FIG. 22). Observations by confocal microscopy suggested that these nucleoplasmic aggregates were distributed throughout the nucleoplasm. Mutating the CSIM terminal sequence (SEQ ID NO: 32) to CSIL was predicted to favor geranylgeranylation by GGTase I rather than farnesylation by FTase (Cox & Der, *Curr. Opin. Pharmacol.* 2:388-393, 2002) and therefore generate an FTI-resistant form of the protein. In this case, progerin-induced nuclear blebbing persisted (FIG. 22) indicating that the persistent modification of any prenoid group promotes the progerin phenotype. Similar results for all of these constructs were obtained with HEK-293 cells and NIH-3T3 cells.

We then explored the effect of treating HeLa cells transiently transfected with wild-type lamin A-CSIM, progerin-CSIM, progerin-SSIM, and progerin-CSIL with the clinical candidate FTI lonafarnib (Ganguly et al., Curr. Med. Chem. 8:1419-1436, 2001). Following a single dose of 0, 0.5, 1.0, 2.0 µM at the time of transfection, cells were visualized 48 hours later (FIGS. 23 and 24). In the wild-type lamin A-CSIM transfected cells, cell counting demonstrated that the percentage of nuclear blebbing was unchanged despite treatment, remaining at approximately 5%, which is the typical blebbed percentage for normal wild-type cells (Goldman et al., Proc. Natl. Acad. Sci. USA 101:8963-8968, 2004). In contrast, those cells transfected with the progerin-CSIM constructs showed a dramatic dose-dependent response ($p<0.0001$), with the nuclei approaching normal blebbing percentages with a single dose of 2.0 µM of lonafarnib. The progerin-CSIL mutant, predicted to be geranylgeranylated, was completely resistant to treatment with the FTI, evidence that it is inhibition of the farnesylation of progerin, and not of any other endogenous farnesylated protein, that is responsible for the improvement in nuclear phenotype seen with FTI treatment. As expected, there was no difference seen with FTI treatment of the progerin-SSIM mutant, as prenylation had already been completely inhibited. Similar results for all of these constructs were obtained with HEK-293 and NIH-3T3 cells using the FTIs L-744832 or FTI-2153 in doses ranging from 1.0 µM to 10 µM.

Next, the effect of FTIs on nuclear blebbing was examined in cells from individuals with HGPS, in this case dermal fibroblasts. Cultured fibroblasts from three HGPS patients and one unaffected mother were treated for three days with a once daily dose of lonafarnib. In order to observe nuclear morphology at the end of treatment, nuclei were stained with an antibody for lamin A and C (FIGS. 25 and 26). On day three, all three HGPS fibroblast lines demonstrated a significant dose-dependent reduction in nuclear blebbing that was unaffected by either patient age or cell passage number ($p<0.0001$).

If treatment with FTIs is to be considered a viable option for HGPS, it is important to determine whether authentic progerin, like K-Ras and some other farnesylated proteins (Zhang et al., J. Biol. Chem. 272:10232-10239, 1997) could still be geranylgeranylated in the presence of FTIs and therefore resistant to FTI treatment. To explore this possibility, a series of experiments were performed examining the migration of progerin on a highly resolving gel when treated with either an FTI, a geranylgeranyltransferase inhibitor (GGTI), or a combination of both drugs. The appearance of a shift in mobility to a slower migrating form is a standard method of demonstrating the ability of FTIs to prevent the processing of farnesylated proteins. Treatment with GGTI alone had no effect on the mobility of progerin (FIG. 27), demonstrating that progerin is not normally geranylgeranylated. However, GGTI did completely shift the mobility of progerin-CSIL whereas FTI had no effect, confirming that this mutant was processed as expected. Importantly, progerin treated with either an FTI or with FTI+GGTI migrated identically with vehicle-treated, completely unprocessed progerin-SSIM mutant, demonstrating that the processing of progerin can be completely inhibited by FTI treatment alone, and that progerin is not alternatively geranylgeranylated when farnesylation is inhibited.

Discussion

Farnesylation, a post-translational modification involving the addition of a 15-carbon isoprene moiety, was first implicated as a potential anti-cancer target when it was discovered that the oncoprotein, Ras, which has been estimated to be involved in up to 30% of all human cancers (Bos, Cancer Res. 50:1352, 1989), required farnesylation for its function (Hancock et al., Cell 57:1167, 1989; Casey et al., Proc Natl Acad Sci U S A., 86:8323, 1989; Schafer et al., Science 245:379, 1989). With the subsequent purification of the FTase enzyme (Reiss et al., Cell 62:81-88, 1990), a vigorous research effort in the pharmaceutical industry has identified and developed a number of small molecule compounds that potently and selectively inhibit farnesyltransferase (Sebti & Der, Nat. Rev. Cancer 3:945-951, 2003). Two of these drugs (lonafarnib/SCH66336 from Schering Plough and tipifarnib/R115777 from Johnson and Johnson) have entered Phase III trials and have been well tolerated, including in trials involving children (Doll et al., Curr. Opin. Drug Discovery Dev. 7:478-486, 2004). Lonafarnib competes with protein substrates for binding to the farnesyltransferase enzyme (Bishop et al., J. Biol. Chem. 270:30611-30618, 1995).

Similar to Ras, the lamin A precursor is also farnesylated, with farnesylation serving as a required step to both insert prelamin A into the nuclear membrane as well as to allow for the two downstream cleavage steps which complete the processing of lamin A (Beck et al., J. Cell Biol. 110:1489-1499, 1990). With the knowledge that the single C to T base change seen in nearly all cases of HGPS created a cryptic splice site and thus deleted the normal second endoproteolytic cleavage site in the lamin A processing pathway, it was hypothesized that progerin was forced to retain its farnesyl group and could not therefore dissociate itself from the nuclear membrane. With other members of the nuclear lamina also potentially becoming trapped in complexes with the mislocalized progerin, a mechanistic connection between this permanently farnesylated state and the striking nuclear blebbing and disrupted nuclear architecture seen in HGPS cells was proposed, and the possibility of preventing or reversing this phenotype through farnesyltransferase inhibitors was raised (Eriksson et al., Nature 423:293-298, 2003).

It was hypothesized that FTIs would reduce the dominant negative effect of mature progerin on nuclear membrane structure. This pharmacologic effect would not, however, be specific for progerin; FTIs would also decrease levels of wild-type lamin A, increase the levels of unfarnesylated prelamin A, and no doubt affect the posttranslational processing of dozens of other farnesylated proteins. Although total cellular lamin A would be expected to decrease, it was hypothesized that the net effect could still be beneficial, as the abnormal splice that leads to progerin is produced rather inefficiently by the mutant allele, and so progerin is present in much lower quantities than wild-type lamin A. Furthermore, only a small amount of mature lamin A is necessary for proper nuclear envelope assembly (Lourim & Krohne, J. Cell Biol. 123:501-512, 1993). In support of this idea, clinical trials using FTIs demonstrate little toxicity, even when levels of unfarnesylated prelamin A are significantly raised (Taveras et al., Curr. Top. Med. Chem. 3:1103-1114, 2003). Complete absence of lamin A, however, leads to serious consequences and disease (Sullivan et al., J. Cell Biol. 147:913-920, 1999).

The possibility that progerin would be geranylgeranylated in the presence of FTIs was also explored. This outcome, if found, might limit the utility of this approach. In the presence of FTIs, both oncogenic K-Ras and N-Ras serve as alternative substrates for the related enzyme geranylgeranyltransferase I (GGTase I), thus remaining biologically active and fully capable of signal transduction and malignant transformation (Ganguly et al., *Curr. Med. Chem.* 8:1419-1436, 2001; Whyte et al., *J. Biol. Chem.* 272:14459-14464, 1997; Rowell et al., *J. Biol. Chem.* 272:14093-14097, 1997; James et al., *Proc. Natl. Acad. Sci. USA* 93:4454-4458, 1996). Thus, although H-Ras does not undergo alternative prenylation when FTase activity is blocked, FTIs are not effective inhibitors of the two Ras isoforms most commonly mutationally activated in human tumors, compromising the effectiveness of FTIs in the treatment of cancer.

Fortunately, data reported here confirm that such alternative isoprenylation does occur to any detectable degree with progerin, the processing of which is fully inhibited by FTI alone. These results indicate that farnesylated progerin is responsible for the dysmorphic nuclear morphology seen in HGPS, as inhibition of farnesylation via both genetic mutation and pharmacological intervention prevents nuclear blebbing and redistributes the mutant progerin protein from the nuclear membrane into nucleoplasmic aggregates.

Beyond the prevention of this nuclear phenotype in transfected cells caused by ectopically expressed progerin, the ability of lonafarnib to cause a significant reduction in the percentage of blebbed nuclei seen in HGPS fibroblasts, even at high passage numbers, is encouraging evidence of its therapeutic potential against endogenous progerin. Perhaps the removal of farnesylated progerin, whether through gene expression changes or through the actual mechanical stabilization of the nuclear scaffolding, would cause the cells that are most prone to damage in HGPS to be rescued. In support of this idea is recent work showing that by simply reducing levels of farnesylated prelamin A by 50%, the nuclear blebbing and progeria-like phenotype seen in ZMPSTE24-deficient mice could be eliminated (Fong et al., *Proc. Natl. Acad. Sci. USA* 101:18111-18116, 2004).

The results provided herein support the hypothesis that it is the permanently farnesylated state of progerin that allows it to exert its dominant negative effects and cause the devastating effect on nuclear structure and function. Further, it has been demonstrated herein that FTIs are capable of reversing this nuclear phenotype. Since FTIs are currently under evaluation in Phase III clinical trials as anti-cancer drugs (Sebti & Der, *Nat. Rev. Cancer* 3:945-951, 2003), there is considerable patient information on FTI activity and toxicity. Therefore, FTIs may be a feasible therapeutic approach for HGPS.

This disclosure provides evidence that a farnesyltransferase inhibitor can reverse or inhibit cellular effects caused by the expression of progerin, or caused by influence of lamin A on atherosclerosis and aging. The disclosure further provides methods and compositions that exploit this discovery in order to treat or ameliorate HGPS and other laminopathies, as well as cellular aging and atherosclerosis. It will be apparent that the precise details of the methods and compositions described may be varied or modified without departing from the spirit of the described invention. We claim all such modifications and variations that fall within the scope and spirit of description and the claims below.

The invention claimed is:

1. A method of reducing at least one clinical symptom of Hutchinson-Guilford Progeria Syndrome (HGPS) in a subject having HGPS, the method comprising administering to the subject a therapeutically effective dose of a farnesyltransferase inhibitor (FTI).

2. The method of claim 1, wherein the clinical symptom of HGPS comprises one or more of failure to thrive, maldevelopment, cardiovascular disease, abnormal bone density, distal bone resorption, osteoporosis, or decreased adipose tissue.

3. The method of claim 2, wherein the clinical symptom is a cardiovascular disease comprising one or more of atherosclerosis, atherosclerotic plaques in large or small arteries, interstitial fibrosis, stenosis, or paucity of medial smooth muscle cells.

4. The method of claim 1, wherein the method prevents progression or retards progression of HGPS in the subject.

5. The method of claim 1, wherein the FTI is PD169541, R115777, SCH66336, L-744832, FTI-2153 or a derivative thereof that maintains farnesyltransferase inhibitory activity.

6. The method of claim 1, further comprising administering a second therapeutic compound to the subject.

7. The method of claim 6, wherein the second therapeutic compound is not a farnesyltransferase inhibitor (FTI).

8. The method of claim 1, wherein the therapeutically effective amount of the FTI is about 0.1 nM per kilogram (kg) body weight to about 1 µM per kg body weight.

9. The method of claim 1, wherein the therapeutically effective amount of the FTI is 0.1 to 200 mg/kg body weight.

10. The method of claim 9, wherein the therapeutically effective amount of the FTI is 1.0, 10, 25, 50, or 100 mg/kg body weight.

11. The method of claim 1, wherein the FTI is lonafarnib (SCH66336).

12. The method of claim 11, wherein the therapeutically effective amount of SCH66336 is at least 115 mg/m$^2$ BID.

13. The method of claim 1, wherein the therapeutically effective amount of the FTI is about 1 nM to about 500 nM per kg body weight.

14. The method of claim 1, wherein the therapeutically effective amount of the FTI is about 5 nM to about 50 nM per kg body weight.

* * * * *